United States Patent [19]

Mier et al.

[11] Patent Number: 5,212,050

[45] Date of Patent: May 18, 1993

[54] METHOD OF FORMING A PERMSELECTIVE LAYER

[76] Inventors: Randall M. Mier, 215 Nepean Avenue #1107, Ottawa, Ontario, Canada, K2P 0B7; Sylvia Piznik, 12 Corrinne Ct., Jackson, N.J. 08527; Imants R. Lauks, 1011 Yardley-Morrisville Rd., Yardley, Pa. 19067; Graham Davis, 15-04 Fox Run Dr., Plainsboro, N.J. 08536

[21] Appl. No.: 568,441

[22] Filed: Aug. 15, 1990

Related U.S. Application Data

[60] Division of Ser. No. 432,714, Nov. 7, 1989, which is a continuation-in-part of Ser. No. 381,223, Jul. 13, 1989, abandoned, which is a continuation-in-part of Ser. No. 270,171, Nov. 14, 1988, abandoned.

[51] Int. Cl.[5] .................................................. G03C 5/00
[52] U.S. Cl. .................................... 430/320; 430/311; 430/313; 430/325; 430/326; 430/328; 430/330; 435/288
[58] Field of Search ............... 430/320, 325, 326, 328, 430/330, 304, 313, 644, 311; 435/288

[56] References Cited

U.S. PATENT DOCUMENTS

| | | |
|---|---|---|
| 3,572,400 | 3/1971 | Casner et al. . |
| 3,890,176 | 6/1975 | Bolon ........................... 430/330 |
| 4,065,357 | 12/1977 | Groves . |
| 4,073,713 | 2/1978 | Newman . |
| 4,218,298 | 8/1980 | Shimada et al. . |
| 4,258,001 | 3/1981 | Pierce et al. . |
| 4,307,181 | 12/1981 | Ganguillet et al. .............. 430/315 |
| 4,464,460 | 8/1984 | Hiroka et al. .................. 430/313 |
| 4,481,049 | 11/1984 | Reichmenis et al. ............ 430/313 |
| 4,551,156 | 11/1985 | Li . |
| 4,562,157 | 12/1985 | Lowe et al. . |
| 4,632,901 | 12/1986 | Valkirs et al. . |
| 4,634,027 | 1/1987 | Kanarvogel . |
| 4,671,288 | 6/1987 | Gough . |
| 4,734,184 | 3/1988 | Burleigh et al. . |
| 4,759,828 | 7/1988 | Young et al. . |
| 4,781,733 | 11/1988 | Babcock et al. . |
| 4,894,339 | 1/1990 | Hanazato et al. ............... 435/288 |

FOREIGN PATENT DOCUMENTS

| | | |
|---|---|---|
| 0226470 | 6/1988 | European Pat. Off. . |
| 61-149086 | 7/1986 | Japan . |
| 61-176845 | 8/1986 | Japan . |
| 61-234349 | 10/1986 | Japan . |
| 61-283862 | 12/1986 | Japan . |
| 62-235556 | 10/1987 | Japan . |
| 62-261952 | 11/1987 | Japan . |
| 63-101743 | 5/1988 | Japan . |
| 63-223557 | 9/1988 | Japan . |

OTHER PUBLICATIONS

Weetall, H. H., Methods Enzymology, 1976 44: 134–149.
Kallury et al., Anal. Chem., 1988, 60: 169–172.
Fujihara et al., J. Electoanal. Chem., 1985, 195: 197–201.
Fujihara et al., Bull. Chim. Soc. Jpn., 1986, 59: 975–980.
Murakami et al., Anal. Letters, 1986, 19: 1973–1986.
Yao T., Analytica Chim. Acta, 1983, 148: 27–33.

*Primary Examiner*—Marion E. McCamish
*Assistant Examiner*—Christopher D. RoDee

[57] ABSTRACT

A method of forming a permselective layer on preselected areas of a substantially planar sensing device is disclosed. The claimed method includes establishing and confining a liquid film, derived from a silane compound mixed in a suitable solvent, within a predetermined area of the sensing device. The process relates to photolithographic imaging and developing methods coupled to a film-curing step that provides a patterned permselective layer having the desired semipermeable characteristics.

48 Claims, 18 Drawing Sheets

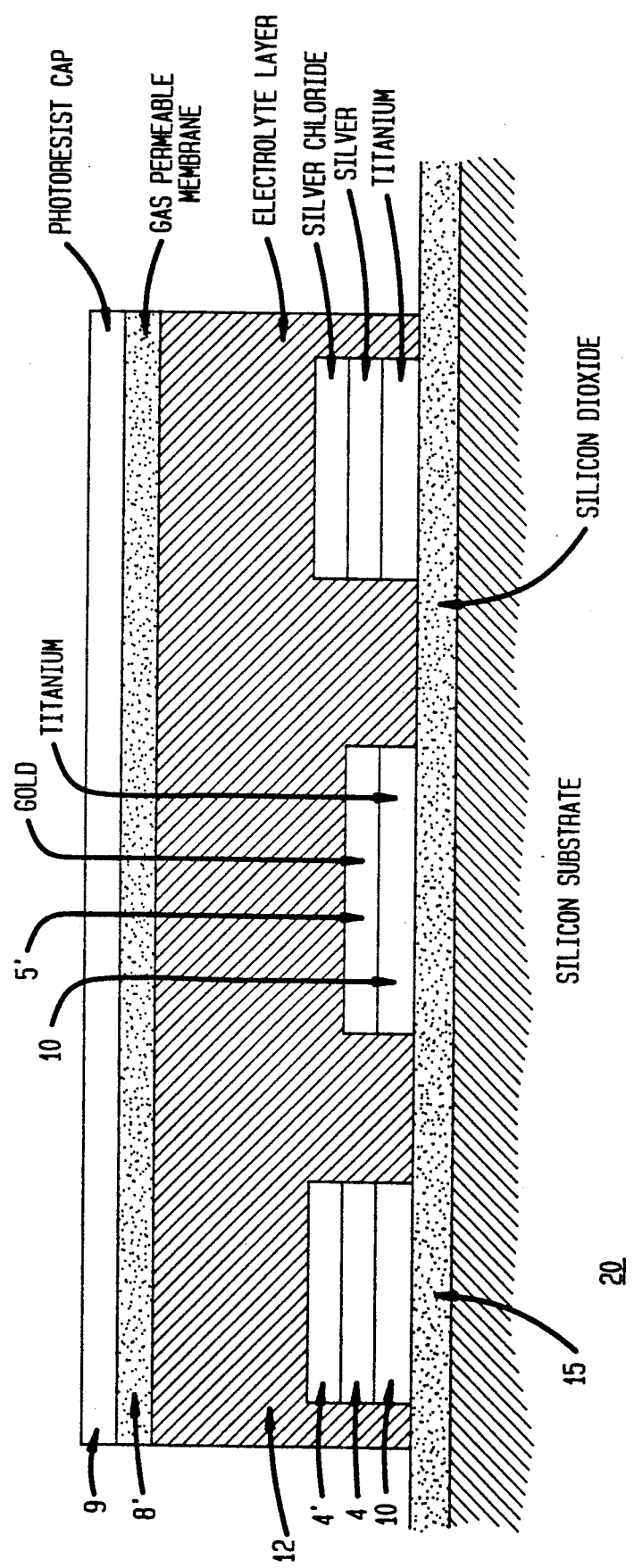

COMPUTER CONTROLLED MOVEMENT

METHOD OF FORMING A PERMSELECTIVE LAYER

CROSS-REFERENCE TO RELATED APPLICATIONS

The present application is a division of prior co-pending U.S. application Ser. No. 07/432,714, filed Nov. 7, 1989, which, in turn, is a continuation-in-part of prior co-pending U.S. application Ser. No. 07/381,223, filed Jul. 13, 1989, now abandoned, which, in turn, is a continuation-in-part of prior co-pending U.S. application Ser. No. 07/270,171, filed Nov. 14, 1988, now abandoned. The disclosures of these prior applications are incorporated by reference herein.

TABLE OF CONTENTS

1. Field of the Invention
2. Background of the Invention
   2.1. Representative Nonmicrofabricated Electrodes
   2.2. Previous Attempts at Mass Production
      2.2.1. Photopatterning Method
      2.2.2. Screen Printing Methods
      2.2.3. Ink Jet Method
      2.2.4. Microsyrinqe Methods
   2.3. Silane Reagents and Permselective Layers
   2.4. Film-Forming Latices
   2.5. Immunoassay Technology
   2.6. Colorimetric Assays
   2.7. Electrochemical Sensors and Assay
3. Summary of the Invention
4. Brief Description of the Figures
5. Detailed Description of the Invention
   5.1. Amperometric Glucose Sensor
      5.1.1. Amperometric Base Sensor
      5.1.2. Adhesion Promoter and Semipermeable Solid Film
      5.1.3. Overlaid Biolayer
      5.1.4. Analyte Attenuation (AA) Layer
      5.1.5. Finishing Steps and Additional Embodiments
      5.1.6. An Amperometric Dioxygen Sensor, Electrolyte Layer, and Alteranative Permselective Layer
      5.1.7. Performance of the Glucose Sensor
   5.2. Ligand/Ligand Receptor-Based Biosensors Adapted for Conducting Biological Assays or Chemical Testing
      5.2.1. An LLR-Based Biosensor Adapted for Immunoassays
      5.2.2. Methods for Performing Electrochemical Assay Procedures
      5 2 3. Novel Electrochemical Detection of Enzymatic Breakdown Products of BCIP and Related Analogs or Derivatives Thereof
   5.3. Blood Urea Nitrogen (BUN) Sensor
      5.3.1. BUN Base Sensor
      5.3.2. BUN Biolayer
      5 3.3. Performance of the BUN Sensor
   5.4. Automated Microdispensing System
      5.4.1. Further Compositions and Methods Useful for Microdispensing Localized Discrete Film Layers of Controllabel but Uniform Dimensions
         5.4.1.1. Volumetric Microdispensing of Fluids
         5.4.1.2. Fluid Compositions with Predetermined Surface Tension
         5.4.1.3. Methods for Tailoring the Surface Energy of a Planar Structure
   5.5. Creatinine and Creatine Sensors
   5 6. Other Characteristics
6. Examples
   6.1. Glucose Sensor
      6.1.1. Base Sensor Fabrication with Signal Line Passivation
      6.1.2 Permselective Silane Layer
      6.1.3. Photoformable Fish Gelatin as Support Matrix for Biolayer
      6.1.4. Glucose Sensor Without Signal Line Passivation and Use of Chromium-Based NPR Matrix
      6.1.5. Analyte Attenuation (AA) Layer
   6.2. Preparation of LLR-Based Biosensors and Methods for the Use Thereof
      6.2.1. Base Sensor Fabrication
      6.2.2. Post-Processing of Base Sensor
      6.2.3. Layers for the Detection and Measurement of Human IgG
      6.2.4. Analyte: Theophylline
      6.2.5. An LLR-Based Biosensor for Human IgG Equipped with Underlying Electrolyte and Gas Permeable Layers
      6.2.6. Alternative Theophylline Biosensor
      6.2.7. Assay Procedure for the Analysis of Human IgG
      6.2.8. Assay Procedure for the Analysis of Theophylline
   6.3. Uric Acid Sensor
   6.4. Co-Processed Glucose and Cholesterol Sensor
   6.5. Adenosine-5-Triphosphate Sensor
   6.6. Alternative Embodiment of an Adenosine-5-Triphosphate Sensor
   6.7. Creatinine Sensor
   6.8. Creatine Sensor
   6.9. Blood Urea Nitrogen (BUN) Sensor
   6.10. Microdispensable Membrane Formulations
      6.10.1. Potassium Ion Membrane
      6.10.2. Chloride Ion Membrane
      6.10.3. Sodium Membrane
      6.10.4. Ammonium Membrane
      6.10.5. Urease Membrane
      6.10.6. pH Membrane
      6.10.7. Calcium Ion Membrane
   6.11. Pretreatment of Water Surface and Deposition of Selected Membranes

1. FIELD OF THE INVENTION

This invention relates to wholly microfabricated biosensors, methods and materials for the mass production thereof, and their use in the determination of the presence and/or concentration of a variety of selected analyte species. In particular, the integrated biosensors of the present invention may be manufactured by a process which allows the incorporation of a variety of bioactive molecules, which bioactive molecules provide the basis of the analytical technique, through the use of materials which are compatible with the bioactive molecules and which materials have been especially adapted for that purpose. The integrated biosensors of the instant invention are also fully compatible with undiluted biological fluids and may be utilized in a wide range of medical, as well as nonmedical, applications.

More particularly, this invention relates to novel electrochemical assay procedures and to novel wholly microfabricated biosensors useful in determining the presence and/or concentration of biological species (analytes) of interest. The invention also relates to the novel use of a non-electroactive substrate (hereinafter the "substrate") that does not undergo detectable oxidation or reduction at an electrode's operating potential, but which substrate undergoes a reaction with a substrate converter which gives rise to changes in the concentration of detectable electroactive species, these changes are measured and related to the concentration of the biological species of interest. Additionally, the invention pertains to methods for the microfabrication of the biosensor.

The assay procedures and biosensor of this invention are also exemplified as being useful in affecting immunoassays. Such immunoassays are also exemplified wherein the substrate converter is an enzyme (alkaline phosphatase) that reacts with the substrate (5-bromo-4-chloro-3-indoxyl phosphate) to produce changes in the concentration of electroactive species (dioxygen and hydrogen peroxide) which are electrochemically detected with the biosensor, an immunosensor in this instance. Both sandwich and competitive assays can be effected using the procedures and biosensor of the present invention. In these assays one embodiment of the biosensor comprises a base sensor comprising a catalytic electrode and optional reference electrode, an adhesion promoter layer overlaid on the biosensor, and a bioactive layer that is covalently immobilized on the adhesion promoter layer, which bioactive layer is a receptor of the immunological analyte of interest.

2. BACKGROUND OF THE INVENTION

Great effort has been expended in the development of chemical sensors which can measure the presence and/or concentration of chemical species in blood or other biological fluids. These sensors can be macroelectrodes (nonmicrofabricated) of the everyday bench top variety for measuring the pH of samples, and they may sometimes take the form of microelectrodes suitable for implantation within the body of a subject. Such devices are presently made individually or in certain cases by a combination of hand assembly and manufacturing methods which may include the thin-film and photoresist techniques currently used to manufacture integrated circuits (See, for example, Pace, S., *Sensors and Actuators* 1982, 1, 475; Zemel, J.N., U.S. Pat. No. 4,302,530 in which is disclosed a method for fabricating a "substance-sensitive" photodefinable layer over semiconductor devices, especially ion-selective field effect transistors (ISFET)). In spite of this considerable and continuous effort, sensors based upon this ISFET technology have not become common articles of commerce. The fact is that wholly microfabricated biosensors, that is, sensors which are uniformly mass produced *solely* by thin-film techniques and the micromanufacturing methods, useful in the clinical setting and adaptable to the detection and measurement of a whole host of chemical and biological species, have not been manufactured successfully.

It is apparent that the degree of complexity involved with the mass production of commercially viable biosensors is much more formidable than even those persons of ordinary skill in the art once perceived. Of major concern is the compatibility of inherently harsh physical and chemical processes, associated with existing semiconductor manufacturing methods, with sensitive organic compounds and labile biologically active molecules which comprise part of a functioning biological sensor. An article by Eleccion (Eleccion, M. *Electronics* 1986, June 2, 26–30) describes the current state of affairs with regard to microsensors and makes brief references to active areas of research including the detection of specific ions, gases, and biological materials. Progress in the area of field effect transistors (FETs) is noted and problems and limitations with present manufacturing methods are discussed.

Numerous other review articles describe a variety of electrochemical devices including ion-selective electrodes (ISEs) and ISFETs which incorporate enzymes or immunoactive species (See, for example, Pinkerton, T.C. and Lawson, B.L. *Clin. Chem.* 1982, 28(9), 1946–1955; Lowe, C.R. *Trends in Biotech.* 1984, 2(3), 59–65; Koryta, J. *Electrochim. Acta* 1986, 31(5), 515–520; DeYoung, H.G. *High Tech.* 1983, Nov., 41–50; Davis, G. *Biosensors* 1986, 2, 101–124 and references cited therein). Also, the general principles of operation of enzyme-based sensors have been reviewed (See, Carr, P.W. and Bowers, L.D. *Immobilized Enzymes in Analytical and Clinical Chemistry*, Wiley-Interscience (1980). Various mathematical models of operation have been examined, including the external mass-transfer model by Racine, P. and Mindt, W. *Experientia Suppl.* 1971, 18, 525. Significant problems and limitations in the fabrication of these devices remain unconquered, however, especially with regard to the fabrication of sensors intended for the analysis of nonionic species. The mass production of biosensors based upon ionselective electrodes (ISEs) would be particularly useful as these sensors can be adapted easily for the analysis both of ionic as well as uncharged analyte species.

It is also important to note that in current clinical settings medical practitioners commonly request that analyses of one or more components of a complex biological fluid such as whole blood. Currently, such analyses require a certain amount of processing of the whole blood, such as filtration and centrifugation, to avoid contamination of the instruments or to simplify subsequent measurements. Frequently, blood samples are sent to a remote central facility where the analyses are performed. Patients are thus deprived of valuable information which, in most cases, is not available for hours, sometimes days. Clearly, substantial advantages can be envisaged if analyses on undiluted samples can be carried out and if instruments or sensors can be produced which can perform real-time measurements.

2.1. Representative Nonmicrofabricated Electrodes

It should be pointed out that many glucose sensors have been constructed using nonmicrofabricated or "macro" electrodes (See, for example, Fischer, U. and Abel, P., *Transactions of the American Society of Artificial Internal Organs* 1982, 28, 245–248; Rehwald, W., *Pflugers Archiv* 1984, 400, 348–402; Gough, D.A., U.S. Pat. No. 4,484,987; Abe, H. et al., U.S. Pat. No. 4,515,584; Lunkska, E., U.S. Pat. No. 4,679,562; and Skelly, P., UK Patent Application 2,194,843). However, no aspect of thin-film processing is described in the manufacturing processes disclosed by the references cited above.

The combination of a layer containing the enzyme urease and an ammonium ion-selective electrode or an ammonia gas sensing electrode is known in the art. A recent example of such a diagnostic system is described by Conover, G., et al. in U.S. Pat. No. 4,713,165. In this system, a nitrocellulose membrane is immersed in a solution of the enzyme urease which is absorbed into the membrane. This enzyme-containing membrane, in its dessicated state, is then mounted onto the surface of an ammonium ISE. The resulting macroelectrode device is used to perform a blood urea nitrogen (BUN) measurement in biological fluids, such as serum, plasma, blood, and the like.

Another illustrative example of the earlier approaches to the manufacture of urea sensors is described by Williams in U.S. Pat. No. 3,776,819. Similar to the previous reference, a urease layer is coated over a cation-sensitive electrode, which layer may comprise urease and gelatin, fibrin, or filter paper pulp. An outer semipermeable membrane made from collodion (a cellulosic material) or cellophane is common, also.

2.2. Previous Attempts at Mass Production

While the unit cell of a base sensor, typically an electrode, can be duplicated on a planar surface such as a silicon wafer (See, Bergveld, P., *IEEE Transactions of Biomedical Engineering BME* 1972, 19, 342–51), a viable method for the deposition of a complex set of layers which confers selectivity and sensitivity to the base sensor has not been demonstrated or shown to be fully compatible with reported integrated circuit processing techniques. Such complex layers would contain relatively labile biological molecules such as ionophores, enzymes, antibodies, antigens or fragments thereof and are, in general, weak and sensitive to mechanical agitation. Although such layers may be applied onto a wafer, preventing their inactivation and/or destruction due to further processing steps is not readily achieved because such processing commonly includes exposing the wafer to organic chemicals, strong acids and bases, heat, or subjecting the wafer to mechanical agitation, dicing, or scribing, usually accompanied by wash steps which employ low-pressure water-jets.

To prevent the destruction of these fragile layers, it has been a common practice in the prior art to dice or cut the semiconductor wafer into individual base sensors before the biolayers are established. Any additional packaging (e.g., wire bonding the sensor to a connector, encapsulating the device to provide adequate passivation) is also performed prior to applying the biologically active layers. Such complete devices are, therefore, produced only partially in a manner which is compatible with automated mass production methods. For example, the enzyme urease has been deposited onto the gate of a *single pre-encapsulated* ion-selective field effect transistor (ISFET) (Karube, I. et al., *Analytica Chimica Acta* 1986, 185, 195–200).

European Patent Application No. 0 012 035 provides ample discussion regarding the deficiencies of current FET devices, foremost of which is their limited applicability to the analysis of nonionic species. In an attempt to combine electrochemistry and semiconductor technology, miniaturized multiple sensors are fabricated on a single chip. The utility of this reference is limited, however, because the disclosure only speaks in general terms and contains no enabling description of the critical biolayers and protective barriers which are critical to the successful microfabrication of functional biosensors. In fact, only materials such as cellulose and a poly(vinyl chloride) (PVC) layer containing valinomycin (sensitive to potassium ions) or nonactin (sensitive to ammonium ions) are specifically disclosed, and the deficiencies of these materials have been known in the biosensor art for sometime. Representative articles on the subject of PVC membranes and the like for use in ISEs abound and include: Davies, D.G et al. *Analyst* 1988, 113, 497–500; Morf, W.E. *Studies in Analytical Chemistry*, Punger, E. et al. (Eds.), Elsevier, Amsterdam (1981) p. 264; Ammann, D. *Ion-Selective Microelectrodes*, Springer (1986); Oesch, U. et al. *Clin. Chem.* 1986, 32. 1448; Oggenfuss, P. et al. *Analytica Chim.* Acta 1986, 180, 299; Thomas J.D.R. *Ibid.* 1986, 289; and Thomas, J.D.R. *J. Chem. Soc. Faraday Trans. I* 1986, 82, 1135.

Also, certain Japanese publications merit some discussion. Japanese Application No. 61-234349 describes a FET semiconductor biosensor coated with a solution of enzyme and a crosslinking agent to provide a crosslinked layer over the entire semiconductor. Separate applications of commonly used photoresist materials are then required to protect desired areas from a subsequent treatment of protease. Reliance on enzymatic digestion of undesired protein layers is expected to give unreliable and unsuitable dimensional control. Precise dimensional control is an important consideration in the mass production of microstructures. Japanese Application No. 61-283862 discloses a procedure for fixing an enzyme membrane by applying a polymer solution containing an enzyme on a solid surface, drying, applying a crosslinking agent to the resulting film through a mask, and removing noncrosslinked portions of said film. Again, such a technique fails to take advantage of standard photoresist technology and can only lead to a poorly resolved pattern. Another reference, Japanese Application No. 61-254845 employs the typical approach of immersing sensor elements in enzyme-containing solutions and then selectively inactivating the membranes.

2.2.1. PHOTOPATTERNING METHODS

The use of photosensitive synthetic polymers to provide patterned membranes is known. For instance, glucose oxidase has been mixed with a photosensitive synthetic polymer mixture consisting of poly(vinyl pyrrolidone) (PVP) and 2,5-bis(4'-azo-2'-sulfobenzal)cyclopentanone (BASC) (See, Hanazato, Y. et al. *Anal. Chim. Acta* 1987, 193, 87; Hanazato, Y. et al. in European Patent Application No. 0 228 259). The resulting mixture was then used to establish a patterned membrane on a single ISFET device. Equal parts of glucose oxidase and bovine serum albumin (BSA) were used in the mixture which was irradiated and developed using aqueous 1–3% glutaraldehyde. In this system, in which the matrix is a synthetic photosensitive polymer, the authors discuss a number of unsolved problems including saturation of the sensor response at concentrations of glucose above about 3 mM and poor long term stability probably caused by enzyme leakage or degradation in the matrix.

A system similar to that described above has been devised for applying the enzymes glucose oxidase and urease onto adjacent ISFET gates using a photosensitive synthetic polymer consisting of poly(vinyl alcohol) (PVA) and styrylpyridinium or stilbazolium salt (See, Takatsu, I. and Moriizumi, T. in *Sensors and Actuators* 1987, 11, 309; Ichimura, K. U.S. Pat. No. 4,272,620). Also, Moriizumi, T. and Miyahara, Y. in *Sensors and Actuators* 1985, 7, 1 and in an article published in *Proceedings, Int'l. Conf. on Solid-State Sensors and Actuators,* 1985, 148, describe the use of these photosensitive PVA membranes in methods which include spin-coating and injection into micro pools using a microsyringe. The poor long-term stability of the ISFET devices obtained with the spin-coated photopatterned PVA membranes was again acknowledged. The long-term sensitivity of the micro injected layers tended to be greater due partly to the greater thickness of these layers and the correspondingly greater number of enzyme molecules remaining therein. However, in order to form the micro pools, into which the PVA mixtures are injected, a second photosensitive synthetic dry film must first be laminated onto the ISFET, irradiated, and developed to give the framed structures.

Other references exist which deal with the immobilization of urease onto electrochemical devices for performing a diagnostic test. A few of these methods involve pseudo-photolithographic procedures by which the enzyme is incorporated prior to or after the formation of the polymer layer (See, for example, Moriizumi, T. et al. in *Sensors and Actuators* 1986, 9, 373; Kimura, J. et al in *Proceedings, Int'l. Conf. on Solid-State Sensors and Actuators*, 1985, 152; and Japanese Patent Nos. 56-115950 and 62-263457). These methods as described still fall far short of a viable microfabrication process.

Published Japanese Patent Application No. 62-235556 discloses a single sensor having three anodes and a common cathode. The sensor is made with the aid of of azo-group-containing PVA, as the photo-bridged polymer. Glucose oxidase, galactose oxidase, L-amino acid oxidase and alcohol oxidase are among the enzymes claimed to be immoblized. No description is included which suggests the use of any material other than synthetic photosensitive polymers as the immobilization matrix. Furthermore, any teaching with respect to the manufacture of hundreds of identical reliable biosensors on a single wafer is not apparent.

2.2.2. SCREEN PRINTING METHODS

Screen printing of chemically sensitive materials as a step in a process for the mass production of chemical sensors has focused mainly on the deposited inorganic ceramic materials contained in certain organic binders. For example, Oyabu, T. et al., in *J. Appl. Phys.* 1982, 53(11), 7125, describe the preparation of thick film gas sensors using a tin oxide paste and a screen printing method. The process includes a high temperature calcination step which is obviously not compatible with relatively fragile liquid membrane electrodes or enzyme-based sensors. Also, Cauhape, J.S. and co-workers, in *Sensors and Actuators* 1988, 15, 399, discuss the effect of mineral binders on the properties of screen-printed layers of semiconductor oxides. U.S. Pat. No. 4,216,245, granted to Johnson, L.C., discloses a method for making printed reagent test devices using an offset or silk-screen dot printing method.

2.2.3. INK JET METHODS

Published Japanese Patent Application No. 62-223557 discloses a means for manufacturing an array of different enzyme layers on an integrted ISFET device. A hydrophilic porous film is established over the gate on the ISFET and then an ink jet nozzle is used to deposit enzyme onto the film. This process utilizes spray type technology with the fluid drop being first electrically charged and then fired from the nozzle. In this system the nozzle, fluid drop, and substrate surface are never in a contiguous physical contact. The diameter of the drops range from 20 to 100 micrometers. Also, published Japanese Patent Application No. 59-24244 discloses a similar membrane deposition process based on ink jet nozzle technology.

2.2.4. MICROSYRINGE METHODS

As already mentioned briefly, above, Moriizumi and Miyahara have employed microsyringe methods to inject synthetic polymer/enzyme mixtures into the gate regions of ISFET devices. These previously described techniques rely on ditches or pools to confine the dispensed fluid within the area of interest. In the article by Kimura and co-workers (*Proceedings, Int'l Conf. on Solid-State Sensors and Actuators*, 1985, 152, above), ISFET devices are described in which various membrane compositions are deposited with the aid of a microsyringe. Again, a thick film resist polymer must be employed to delineate the area about the gate region of the ISFET device. In this manner, four types of membranes are applied and made separate from one another. No consideration is given to the volumetric profile of the drop (although a droplet value of 0.03 $\mu L$ is given), its surface tension or the free energy of the surface of the device. Also, it is interesting to note that the injected enzyme (e.g., urease or glucose oxidase) solutions, which include a small amount of BSA, are immobilized within the gate region by the subsequent addition of a suitable amount of conventional glutaraldehyde solution.

U.S. Pat. No. 4,549,951 granted to Knudson, M.B. et al. discusses the criticality of the shape and dimension of the ionophore layer but offers no insight for controlling these parameters. This reference teaches the use of a moat, carved around the perimeter of the electrode, to confine the membrane to that area. Some ion-sensitive membrane formulations are described.

Miyagi, H. et al., in articles which appeared in *Technology Research Report of the Institute of Electronics and Communication Engineers of Japan* 1986, 85(304), 31 and 1985 *Pittsburgh Conference*, 1058, describe two membrane deposition methods for ISFET devices: a screen printing method and a microsyringe method. The first employed a fine silica powder additive as a viscosity controlling agent and the second technique once again required a framed structure to hold in the membrane casting solution which was "poured into the frame with a microsyringe."

In a somewhat related method, Bousse, L.J. et.al., in the *Proceedings of the Second Int'l Meeting on Chemical Sensors* 1986, 499, describe a lamination process in which a glass wafer is joined to a silicon wafer by anodic bonding. The bonding is carried out such that a chamber is formed between the two wafers, the floor of which holds an electrochemical transducer. A laser is then used to drill holes through the ceiling of the chamber. Liquid membrane material is then introduced into the chamber, over the transducer, by applying a coat of the liquid membrane, placing the laminated wafer into a partially evacuated bell jar, and then venting the assembly to the atmosphere (thus forcing the liquid membrane material into the evacuated chamber).

It should be apparent that existing techniques for the uniform microfabrication of an array of chemical sensors are wholly inadequate and provide devices with specifications which are decidedly unsatisfactory. Furthermore, what methods exist have been developed mostly for application with ISFET devices. Unfortunately, ISFET and CHEMFET devices will always be plagued with disadvantages which are present intrinsically, such as their limitation to the detection of charged species only (See, for example, the review article by Flanagan, M.T. et al. in *Anal. Chim. Acta* 1988, 213, 23). The manufacture of miniaturized amperometric devices is even less established.

2 3. Silane Reagents and Permselective Layers

The use of silane coupling reagents, especially those of the formula $R'Si(OR)_3$ in which $R'$ is typically an aliphatic group with a terminal amine and R is a lower alkyl group, to attach a macromolecule covalently to a solid support has been known for some time. For example, an article by Weetall, H.H. in *Methods in Enzymology* 1976, 44, 134-139, recommends heating the silane coupling agent to 115° C. to promote the condensation of the agent with hydroxyl groups present on the surface of the solid support. A chemically modified platinum electrode has been described in which γ-aminopropyltriethoxysilane and glutaraldehyde were used in a step-wise process to attach and to co-crosslink bovine serum albumin (BSA) and glucose oxidase (GOX) to the platinum surface (Yao, T. *Analytica Chim. Acta* 1983, 148, 27-33). These references do not contain any teaching that silane coupling reagents can be used for any other function besides promoting adhesion of overlaid materials or acting as a covalent anchoring agent.

Fujihara and co-workers, in *J. Electroanalytical Chem.* 1985, 195, 197-201, describes the use of a toluene solution of n-dodecyltriethoxysilane as a means for blocking the active sites of a catalytic gold electrode surface toward the reduction of hydrogen peroxide. The preparation of a permselective layer of variable thickness and its use to screen out undesired electroactive species while maintaining the high catalytic activity of the electrode surface are not disclosed or suggested.

Two published Japanese Patent Applications refer to the establishment of selective layers on non-microfabricated electrodes. Japanese Application No. 62-261952 describes the use of certain silane compounds, for the formation of a silicon layer which excludes the passage of uric and ascorbic acids but allows the permeation of hydrogen peroxide. Application No. JP 63-101743, pertains to a hydrogen peroxide permselective film which is derived from a high polymer film of poly(allylamine) crosslinked by the action of a suitable chemical agent. None of the references cited above discloses patterned permselective silane layers established on microfabricated devices.

2.4. Film-Forming Latices

Particle latex materials and the distinct "film-forming" latices are old materials. Methods for producing film-forming latices by emulsion polymerization, their properties, and some of their uses have been reviewed (See, for example, Wagner and Fisher *Kolloid Z* 1936, 77, 12; Vanderhoff, J.W. and Hwa, J.C. *Polymer Symposia* Wiley-Interscience, New York (1969)). Additional references include: Whitley, G.S. and Katz, M.K. *Indust. Eng. Chem.* 1933, 25, 1204-1211 and 1338-1348: Matsumoto, T. *Emulsions and Emulsion Technology Vol. II*, Lissant, K.J. (Ed.), Marcel Dekker, New York (1974) Chapter 9; *Encyclopedia of Polymer Science and Technology Vol. 5*, John Wiley & Sons, New York (1966) pp. 802-859; Dillon, R.E. et al. *J. Colloid Sci.* 1951, 6, 108-117; and Sheetz, D.P. *J. Appl. Polym. Sci.* 1965, 9, 3759-3773.

A film-forming latex, ELVACE, containing a potassium chloride reference solution, has been applied over a reference microelectrode for an ISFET device (See, Sinsabaugh, S.L. et. al. *Proceedings, Symposium on Electrochemical Sensors for Biomedical Applications, Vol. 86-14*, Conan, K.N.L; (Ed.), The Electrochemical Society, Pennington, N.J. (1986), pp. 66-73). This reference contains no teaching or suggestion that film-forming latices can be used as a medium containing anything other than an inorganic salt.

In summary, attempts by previous workers to manufacture viable biosensors with all the characteristics and specifications desirable in a reliable mass-produced microfabricated device have met with limited success. One of the more important aspects of wafer level processing, that of dimensional control both in the horizontal and vertical directions of a plurality of layered structures, which dimensional control in turn affects, inter alia, the uniformity of sensor performance, is irrevocably compromised when dicing and packaging occur prior to deposition of the biolayers. Manual handling is often necessitated by the fragility of the immobilizing or supporting layers and the labile nature of the bioactive molecules contained therein. Previous workers have had to resort to such methods, however. A flexible wafer level manufacturing process which utilizes superior materials and which makes possible the accommodation of such sensitive bioactive molecules in a biosensor which can be tailored to a variety of clinical applications would be of major significance.

2.5. Immunoassay Technology

Immunoassays are sensitive diagnostic tools for the in vitro detection of a variety of antigens or antibodies and their association with diseases or other significant physiological conditions. In the early stages of developing immunoassay technology, a polyclonal antibody preparation bound to a solid phase was used in heterogeneous assays whereby a solution of labeled antigen was allowed to compete directly with antigen in a sample to determine the extent of bound labeled antigen or to detect the extent of antigen present in the liquid phase. This method provided a way for measuring the presence and quantity of antigen in the sample being analyzed.

Developments in immunoassay technology then led to non-competitive immunometric assays wherein a polyclonal antibody preparation bound to a solid phase was also employed. In these assays, a sample containing the target antigen was contacted with the solid phase to provide for antigen/antibody binding. Subsequent to an incubation period, the sample was removed from the solid phase and then the solid base was washed to remove any unbound antigen. A solution containing labeled polyclonal antibodies (e.g. with a radionucleotide, enzyme, or fluorescent moiety) was then contacted with the solid phase. Unbound labeled antibody in the liquid phase was separated from the solid phase and bound labeled antibody (antibody:antigen:labeled antibody sandwich) on the solid phase was measured to determine the presence and/or concentration of antigen in the sample.

More rapid immunoassay procedures have also been developed. In these assays at least one of the two washing steps may be eliminated and incubation periods required to reach equilibrium may be shortened.

In the prior described processes the bound antibody is generally affixed to beads or small particles. The antibody can also be coated onto a surface. During the assay an incubation period is generally required of both the solid phase and labeled antibodies. A prolonged incubation period is particularly troublesome if results are needed quickly. Additionally, the long incubation periods and multiple washings have significantly limited the use of the assays to clinical laboratories, which have highly trained personnel and sophisticated equipment to undertake the assay. Consequently, there is presently a need for simpler and more rapid immunoassay protocols, and simpler apparatuses for use in emergency rooms, physicians' offices and even for in-home health care services.

2.6. Colorimetric Assays

Most existing assay protocols, including ELISA and enzymatic assays, provide for colorimetric detection. Generally these methods use a substrate which, itself, becomes a chromophore or which generates a chromophore, the chromophore is then detected spectrophotometrically. However, the spectrophotometric detection may have drawbacks because some measurements take an excessively long time or the sample mixtures are turbid. Some chromophores are also extremely unstable, thus, assay procedures involving nonchromogenic species may be useful.

Indoxyls and some of their derivatives have been employed as substrates in spectrophotometric assays. S. Cotson and S.J. Holt (*Proc. Roy. Soc. B* .1958, 148, 506) investigated their utilization in the production of tissue stains to identify alkaline phosphatase activity. P.L. Ely and L.K. Ashman (*Methods Enzymol.* 1986, 121, 497) studied the use of bromo-chloro indoxyl phosphate as a substrate for determining the specificity of monoclonal antibodies to protein mixtures in alkaline-phosphatase-conjugated antiimmunoglobulin with immunoblots. J.J. Leary, D.J. Brigati and D.C. Ward (*Proc. Natl. Acad. Sci. USA* 1983, 80(13), 4045) utilized bromo-chloro-indoxyl phosphate for visualizing biotin-labeled DNA probes hybridized to DNA or RNA immobilized onto nitrocellulose i.e., bioblots. S.J. Holt and P.W. Sadler (*Proc. Roy. Soc. B* 1958, 148, 481) described the application of the conversion of indoxyl or a substituted indoxyl into the corresponding indigoid dye to cytochemical staining methods for the localization of cellular enzymes.

The kinetics of aerial oxidation of indoxyl and some of its halogen derivatives were studied by S. Cotson and S.J. Holt (Ibid. 1958, 148, 506) as part of &heir histochemical staining studies for work on enzymes. Their observations agree with the generally accepted view that such aerial oxidation reactions, involving free radicals, invariably result in the formation of organic peroxides or hydrogen peroxide, Waters, W.A., *The Chemistry of Free Radicals*, Oxford University Press, (1946). The aerial oxidation of indoxyls was studied utilizing spectrophotometric methods. All of the above references, exploited the chromogenic properties of indigoid compounds derived from indoxyls.

Examples of other chromogenic applications of the oxidative conversion of indoxyl compounds to indigoid dye have included: an indigogenic reaction for alkaline and acid phosphatase histochemical demonstration in disk electrophoresis (E. Epstein, P.L. Wolf, I.P. Horwitz, and B. Zak in *Am. J. Clin. Pathol.* 1967, 48(5), 530); the comparison of simultaneous azo-dye coupling methods and an indigogenic reaction for alkaline phosphatase in polyacrylamide disc gels (T.F. Savage, E.C. Smith, and Collins in *Stain Technol.* 1972, 47(2), 77); protein blotting principles and applications (J.M. Gershoni and G.E. Palade in *Anal. Biochem.* 1983, 131(1), 1); a sensitive method for staining proteins transferred to nitrocellulose sheets (Z. Wojtkowiak, R.C. Briggs, L.S. Hnilica in Ibid. 1983, 129(2), 486); Visualization of antigenic proteins on Western blots (D.A. Knecht, R.L. Dimond in *Anal. Biochem.* 1984, 136(1), 180); a rapid sensitive method for detection of alkaline phosphatase-conjugated anti-antibody on Western blots (M.S. Blake, K.H. Johnston, G.J. Russel-Jones. and E.C. Gotschlich in Ibid. 1984, 136(1), 175); immunoconcentration—a new format for solid phase immunoassays (G.E. Valkirs and R. Barton in *Clin. Chem.* 1985, 31(9), 1427); the use of alkaline phosphatase conjugated anti-immunoglobulin with immunoblots for determining the specificity of monorlonal antibodies to protein mixtures (P.L. Ey and Leonie K. Ashman in *Methods Enzymol.* 1986, 121, 497); and work involving the coupling of redox and enzymatic reactions which has been found to improve the sensitivity of the ELISA-spot assay (C. Franci and J. Vidal (*J. Immunol. Methods* 1988, 107(2), 239).

Again, all of the preceding references rely exclusively on the spectral properties of bromo-chloro-indoxyl phosphate as a colorimetric substrate.

2.7. Electrochemical Sensors and Assay

There has recently been a significant interest in the construction of electrochemical sensors, so-called immunosensors, that are capable of integration into immunoassay protocols. M.J. Green (*Philos. Trans. R. Soc. Lond. B. Biol. Sci.* 1987, 316(1176), 135) has reviewed several immunoassays that incorporate electroactive labels for the amperometric or potentiometric detection of assay products. However, the translation of working laboratory prototypes, as reported in the book, *Biosensors: Fundamentals and Application*, edited by A.P.F. Turner, I. Karube, and G.S. Wilson, Oxford University Press, 1987, into common commercially available articles, has been impeded by the absence of appropriate manufacturing protocols.

A specific example of electrochemical detection as an alternative to color detection is described in *Anal. Chem.* 1984 56, 2355. The reference discloses an assay in which an enzyme label converts an electroinactive compound to a detectable electroactive compound. The electroactive compound, phenol, is oxidized at a potential of +750 mV. However, the method is not generally applicable since other electroactive components are present in blood or serum which are also oxidizable at this potential.

A very recent reference which illustrates the prevailing notions ingrained in those skilled in the art of "immunoelectrochemical sensing" is that by Rosen, I. and Rishpon, J. in *J. Electroanal. Chem.* 1989, 258, 27. In this article, an enzyme is used as a label which is capable of transforming a substrate, which is not electroactive, to one which is. In particular, alakaline phosphatase is the enzyme employed. Several substrates are examined, including phenylphosphate, p-nitrophenylphosphate, and p-aminophenylphosphate. In the electrochemical detection method described, the alcohol products, resulting from the hydrolysis reaction catalyzed by the enzyme (i.e., phenol, p-nitrophenol, and p-aminophenol, respectively), themselves, are detected. The viability of detecting other electroactive species, besides the transformed substrate, is not suggested and, indeed, is never contemplated.

Also, European Patent Applications Nos. 0247796 and 0270206 describe methods for conducting immunoassays which involve primarily moveable magnetic particles to which are bound immunoactive molecules. Enzyme conjugates are described which generate electroactive species such as $H_2O_2$. However, the principal means of detection involves chemiluminescence and, in any event, indoxyl compounds are not mentioned and no microfabricated sensing devices useful in performing immunoassays are disclosed.

3. SUMMARY OF THE INVENTION

The present invention relates to wholly microfabricated biosensors and various processes for the mass microfabrication thereof. The microfabrication processes establish a plurality of thin films and related structures over a planar wafer in a fashion which allows exemplary reproducibility and control over the dimensional features of the overlaid structures. In the present invention, such reproducibility and dimensional control have been realized at the wafer level for the mass production of chemical sensors, which sensors incorporate biologically active macromolecules and other reagents necessary for the conversion of selected analyte molecules to more readily detectable species.

This invention also relates to novel electrochemical assay procedures and to novel wholly microfabricated biosensors useful in determining the presence and/or concentration of biological species (analytes) of interest. The invention also relates to the novel use of a substrate (hereinafter the "substrate") that does not undergo detectable electrochemical oxidation or reduction but which undergoes a reaction with a substrate converter producing changes in the concentration of electroactive species. These changes are measured and related proportionately to the concentration of the analyte of interest. Additionally, the invention pertains to methods for making the biosensor.

The assay procedures and biosensor of this invention are particularly exemplified as being useful in effecting immunoassays. Such immunoassays are also exemplified wherein the substrate convertor is an enzyme that hydrolyzes the substrate. This hydrolyzed substrate can then undergo reactions which produce changes in the concentration of electroactive species (dioxygen and hydrogen peroxide) which are electrochemically detected with the biosensor, a ligand/ligand receptor-based (LLR-based) biosensor in this instance. Both sandwich and competitive assays can be effected using the procedures and LLR-based biosensors of this invention. In these assays, one embodiment of the present biosensor comprises a catalytic electrode and optional reference electrode (base sensor), an adhesion promoter layer overlaid on the biosensor, and a bioactive layer that is immobilized on the adhesion promoter layer, which bioactive layer is a receptor (first member) of the immunological analyte of interest.

The wholly microfabricated biosensor of the present invention comprises a substantially planar wafer on which a first structure comprising a suitable base sensor is established. Additional structures are then established over the resulting base sensor, which additional structures include a semipermeable solid film or permselective layer capable of acting as a barrier against interfering chemical species while allowing the transport of smaller detectable chemical moieties of interest. These detectable chemical moieties are typically electroactive molecules and may include low molecular weight ionic species. The semipermeable solid film may further comprise compounds or molecules which may serve to sensitize the base sensor to a preselected ionic species (e.g., ammonium ion). Furthermore, such permselective layers may also function as adhesion promoters by which the preselected ligand receptor may be immobilized to the wholly microfabricated LLR-based biosensor embodiment of the present invention.

Most noteworthy are the support matrices described in the instant invention which matrices possess the physical and chemical features necessary to support the various bioactive molecules that constitute the principal means for converting the particular analytes in a given analytical sample into detectable and/or quantitatively measureable species. Techniques are disclosed for localizing or patterning said matrices on certain desired areas of the wholly microfabricated biosensor which allow for the optimum control over dimensional features of the biolayers as well as the versatility to accommodate a wide range of bioactive molecules.

Additionally, the present invention also discloses materials which serve, in particular embodiments of the instant biosensor, as overlaid structures for the attenuation of the transport of selected analyte species which are present in high concentrations in the sample. Such analyte attenuation (AA) layers allow for a linear sensor response over a wider range of analyte concentrations than would be observed in the absence of an AA layer. Furthermore, the overlaid AA layer, which is preferably derived from a siloxane/nonsiloxane copolymer, is capable of excluding very large molecules or other contaminating constituents of the sample whose direct contact with the underlying structures would result in interference with or fouling and an eventual reduction in the reliability of the biosensor.

If the AA layer is of the appropriate structure and composition, it may also function as a gas permeable membrane. In certain embodiments of the present invention, such a gas permeable membrane has the practical advantage of allowing only very small molecules to pass through. The gas permeable membrane also insulates the immediate environment of the electrode portion of the biosensor from external fluid turbulence. Thus, the measurements performed by the preferred LLR-based sensor is rendered free of flow dependence.

The AA layer of the instant invention is established on the substrate wafer or any intervening structures with the kind of dimensional, localized, and geometric control which is compatible with the other steps in the overall microfabrication process of the instant invention and the notion of an automated, wafer-level mass-production of biosensors.

Quite apart from the AA layer mentioned above, a semipermeable solid film which is able to function as a molecular weight-sensitive transmissive film is among the layers which can be established by the methods of the present invention. Depending upon the composition and final thickness of this semipermeable solid film, also referred to as a permselective layer, molecules having molecular weights above a given threshold can be effectively excluded from entering and diffusing through such a film. As a general illustration of the function and utility of this permselective layer, molecules having a molecular weight of about 120 or above are effectively blocked by a solid film having a thickness of about 5 to about 10 nm. Varying degrees of control over the size of the molecules excluded and the rates of transport of smaller molecules which are able to diffuse through the solid film can be obtained with solid films having a thickness in the range of about 2 to about 50 nm. With certain types of materials, these permselective layers may be as thin as 1 nm or may be as thick as 100 nm.

This film may be established on the substrate wafer or any planar analyte-sensing device in a number of ways but most conveniently as an initial liquid film, comprising a silane compound mixed with a suitable solvent, which is spin-coated across the wafer. The silane compound has a formula, $R'_n Si(OR)_{4-n}$, in which n is an integer which may be 0, 1, or 2, R' is a hydrocarbon radical comprising 3-12 carbon atoms, and R is a hydrogen radical or a lower alkyl radical comprising 1-4 carbon atoms. Preferably, the solvent contains an amount of moisture sufficient to hydrolyze the alkoxy groups of the silane compound, if present. The wafer bearing the liquid film is then heated to a temperature of about 90°-250° C. for a period of time effective to form the solid film. Typically about 5 to 30 minutes of heating at this temperature is required. The non-volatile content of the initial silane solution determines the final thickness of the permselective layer which can thus be controlled.

If desired, this permselective layer may be formed at specific preselected areas of the device by means of photolithographic processing techniques. Techniques such as "lift-off" and use of a photoresist cap in combination with a plasma-etching or, alternatively, a wet-etching step may thus be employed to define the location and configuration of the semipermeable solid film. The initial liquid silane mixture, much like the majority of other liquid mixtures disclosed for use in the present invention, can also be microdispensed at multiple preselected areas of the sensing device. Such microdispensing of fluid media may be performed automatically and in uniform predetermined quantities by a computer-controlled syringe interfaced with the controlled movements of a vacuum chuck holding the substrate wafer. Such microdispensing techniques are consistent with a microfabrication method and is discussed in further detail below.

Thus, in an amperometric electrochemical sensing device, interfering electroactive species having a molecular weight above a desired threshold (e.g., above 120) may effectively be excluded from interacting with the catalytic electrode surface by employing the permselective silane layer of the present invention. Such a permselective layer, however, allows lower molecular weight electroactive species, like dioxygen and hydrogen peroxide, to undergo a redox reaction with the underlying electrode surface.

In a potentiometric biosensor, a polymeric material having functional groups and chemical properties conducive to the further incorporation of certain ionophoric compounds may be used as a semipermeable ion-sensitive film which is established on the indicator electrode of said sensing device. The development of a potential at the electrode-film interface depends on the charge density, established at equilibrium, of some preselected ionic species. The identity of such ionic species is determined by the choice of the ionophore incorporated in the semipermeable film. An enzyme which is, in turn, immobilized in the novel biolayers described herein catalyzes the conversion of a particular analyte species, present in the analytical sample, to the preselected ionic species.

The permselective layers discussed above are selected for their specificity to the ionic electroactive chemical species which are produced by chemical processes taking place in the overlaid structures referred to herein as the biolayer. The chemical process which converts a selected analyte species or exogenous reagent into an ionic electroactive chemical species is effected by at least one biologically active molecule, such as an enzyme, which is incorporated in the biolayer. The support matrices of the biolayer and methods of the instant invention help to stabilize the bioactive molecules against degradation caused by further processing, storage, handling, or exposure to analyte or reagent compositions. These support matrices must retain a certain degree of porosity such that analytes of interest may freely diffuse through the matrix and undergo chemical transformation. Because the wholly microfabricated biosensors of the instant invention are likely to be stored essentially dry, such porosity will also help in the initial wet up and calibration sequence used to prepare the biosensor for the actual analytical procedure. If the sensitivity of the bioactive molecule so dictates, the support matrix is also able to accept and immobilize enzymes introduced, for instance, from a solution after the matrix has been established locally and/or photolithographically patterned and developed. In any event, a sufficient amount of biocatalyst and/or ligand receptor must be present in the biolayer to overcome any inactivation due to subsequent processing or handling, or due simply to the passage of time during storage. Sufficient biocatalyst/ligand receptor should also be immobilized to provide a favorable condition for the efficient and ready conversion of infusing analyte molecules. Thus, the biolayer of the present invention comprises a sufficient amount of a bioactive molecule capable of selectively interacting with an analyte species and a support matrix in which the bioactive molecule is incorporated, which matrix may be a photoformable proteinaceous mixture, a film-forming latex, or combinations of these materials. As mentioned previously, the analyte species must be able to freely permeate through the support matrix and interact with the bioactive molecule contained therein. A variety of additives disclosed above may be added to the support matrices to further achieve desirable functional and structural characteristics not inconsistent with the objectives of the present invention.

As alluded to earlier, these biolayers are established with the dimensional and geometric control characteristic of wafer level manufacturing procedures. Thin-film techniques, spin-coating, use of photoresist materials, masking, exposure to radiant energy, and developing methods can be utilized for the majority of biologically active molecules. For the preceding techniques, photoformable proteinaceous mixtures are most conveniently used as the support matrix. If necessary, however, extremely labile enzymes may be introduced later, after the photodefined structures have been established. Such support matrices may also serve as electrolyte layers, as well as the photoresist layers over which the ligand receptors of interest may be immobilized. Preferably, the immunoreactive species or ligand receptors are introduced after the photodefined structures have been established.

Alternatively, film-forming compositions, which may include synthetic as well as naturally-derived polymeric materials, can be used to establish the solid matrices especially when microdispensing is the method of choice for establishing the biolayers. Combinations of photoformable gelatins and film-forming latices may be employed. Again, reagents or additives may be incorporated into these layered structures as might be dictated by the particular application or analysis at hand.

The present invention thus relates also to a method of establishing a dispensed layer onto a substantially planar surface. This method succeeds in providing layers having predictable and reproducible dimensions by adjusting the composition of a fluid to be dispensed, until its surface tension and viscosity characteristics are optimized, providing a movable microsyringe assembly, and using the assembly in a manner which allows for close control over the amount of fluid dispensed. Furthermore, the microdispensing method disclosed herein may be coupled effectively with known techniques for altering the free energy of a given surface such that the physical characteristics of the established layer (e.g., contact angle, thickness, volume, or area) may be tailored even further to accommodate a desired application.

Additional layers may also be desirable as mentioned previously to enhance the sensitivity and response time of the device, extend the range of a linear response, and increase the durability of the overlaid structures. In the case of an analyte attenuation layer, certain copolymers comprising siloxane and nonsiloxane units may be employed advantageously. These materials may also be layered or established at a given thickness, anywhere from about 5 to about 500 nm, and may be localized by photolithographic methods. Typically, the analyte attenuation layer should have a thickness sufficient to attenuate the transport therethrough of analyte species having a molecular weight of about 120 or more. As stated previously, these AA layers may also be established at a thickness sufficient to provide a gas permeable membrane. In connection with the photoforming step, a "resist cap" method may be employed, for instance, using a type of photoformable proteinaceous mixture which is also a nonbarrier (i.e., it does not impede or exclude the transport of relevant analyte species).

These and additional objects of the instant invention are apparent from the disclosures and examples included herein.

4. BRIEF DESCRIPTION OF THE FIGURES

The invention may be better understood if reference is made to the accompanying drawings. These drawings, especially the schematics of the wholly microfabricated sensor structures, are qualitative and topological in nature and are not meant to convey absolute dimensional relationships between the various layers or parts of the biosensor.

FIG. 1 Top elevation of a differential amperometric glucose sensor on a 6×3 mm rectangular silicon chip. The significance of the different layers is discussed further in Section 5.1, below. The same general configuration may also be employed for the LLR-based biosensor embodiment of the present invention. Alternatively, FIG. 1 may also illustrate a differential amperometric LLR-based biosensor on a 6×3 mm rectangular chip. The various areas/layers of the chip refer to contact pads (1). signal line (2), passivation (3). silver/silver chloride reference electrode (4), metal catalytic indicator electrode (5), adhesion promoter (6), or localized adhesion promoter (7), coupling means (8), and ligand receptor layer (9).

FIG. 2 Side elevation of one, of the glucose sensor pair of FIG. 1 with surrounding silver/silver chloride reference electrode.

FIG. 3 Side elevation of a potentiometric blood urea nitrogen (BUN) sensor and reference electrode.

FIG. 4 Top elevation of the sensor of FIG. 3 showing an array of different biosensors on a single chip.

FIG. 5 Current output (in namps) of the present glucose sensor (oxidation/reduction of hydrogen peroxide) as a function of electrode potential (mV) using a 20 mM glucose in HEPES buffer sample (O) or HEPES buffer only (X).

FIG. 6 Current output (in namps) of the present glucose sensor as a function of glucose concentration (mM) in the sample.

FIG. 7A An alternative embodiment of an amperometric oxygen sensor of the instant invention which utilizes a gas permeable layer. This configuration is also well-suited for the LLR-based biosensor application of the present invention. In the LLR-based embodiment, the electrolyte layer (12) is also the first photoresist layer; the gas permeable membrane (8') (also referred to as the AA or gas permeable layer) is established over the first photoresist layer; and the photoresist cap (9, also the second photoresist layer) is present above the AA layer.

FIG. 7B The diagram illustrates a configuration in which the gas permeable layer substantially encloses an underlying electrolyte layer (or first photoresist layer in the LLR-based biosensor embodiment).

FIG. 8A An alternative configuration of a glucose biosensor based upon the dioxygen sensor described herein.

FIG. 8B A Ligand/Ligand Receptor-based (LLR-based) biosensor with immobilized ligand receptor or immunoreactive species (45). The underlying sensor configuration is derived from that of FIG. 7B. This illustration also employs coupling means (40) to immobilize the active species (45).

FIG. 9 Uniformity of the response of three blood urea nitrogen (BUN) sensors, wholly microfabricated by the process of the present invention, to a change in the ammonium ion concentration of an aqueous sample from 2 to 20 mM.

FIG. 10 Response of the present IUN sensor to a change in the urea concentration of an aqueous solution from 1 to 10 mM.

FIG. 11 Response of the present BUN sensor to a whole blood sample spiked with urea.

FIG. 12 An illustration of one possible configuration of the automated microsdispensing system of the present invention in which syringe (5), holding the material to be dispensed, is attached to a means, (8), for controlling its displacement in the direction, z, while wafer, (2), is held to a vacuum chuck, (1), whose movement in all directions is, likewise, controlled by an automated, computerized means. The system may also include a visual means for alignment (e.g., video camera equipped with a raticle alignable with appropriate alignment features on the wafer).

FIG. 13 An alternative configuration of the automated microdispensing system comprising multiple syringe holders, (7). The syringes are inserted into openings, (13), and the vacuum chuck and wafer are positioned below the ring, (11), and through large opening, (12).

FIG. 14 A schematic rendering of a typical sandwich assay performed using the present invention is shown. An immobilized ligand receptor (the first member) is positioned near the surface of the biosensor and encounters an analyte molecule (the ligand). The ligand binds to the receptor and is subsequently attached by an antibody-enzyme conjugate (the labeled antibody or the second member). A substrate is added next which undergoes a chemical transformation mediated by the enzyme (the label or substrate converter). The resulting intermediate product then undergoes a cascade of reactions involving the consumption of dioxygen and the production of hydrogen peroxide (both $O_2$ and $H_2O_2$ are detectable, electroactive species) and final product (indigo when the initial substrate is an indoxyl derivative).

5. DETAILED DESCRIPTION OF THE INVENTION

Figure 1:
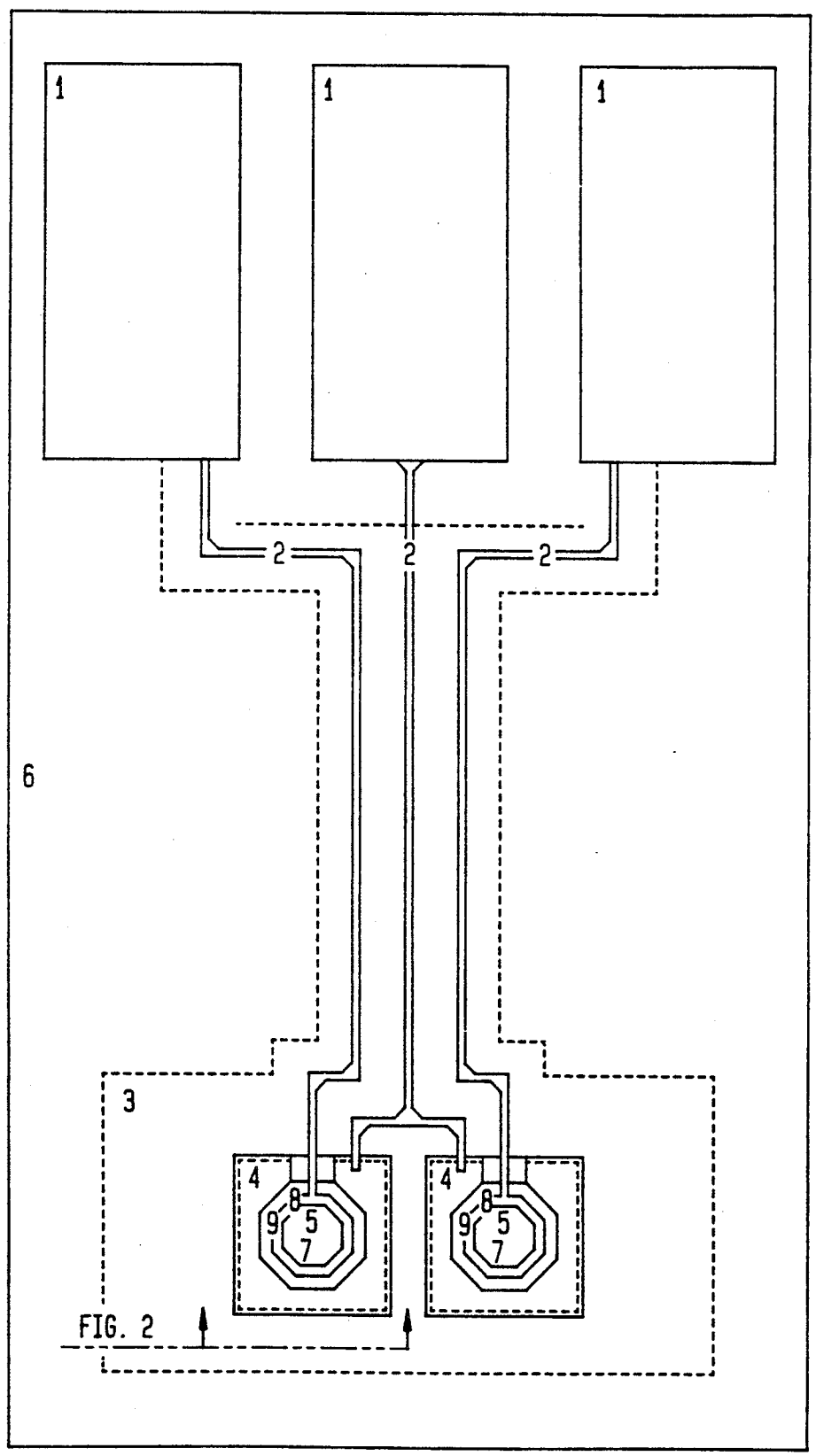

The present manufacturing method is directed to the mass production of biosensors having predictable, uniform response characteristics and which biosensors are useful in a clinical setting for the convenient and real-time detection and quantitative measurement of selected analyte species. The integrated biochemical sensing device is formed on a transducer array by establishing discrete layered structures which are robust and possess a controlled degree of porosity, at least one of which layered structures is capable of immobilizing one or more biologically active species. The term biologically active or bioactive molecule is used to encompass ionophores, ion-exchangers, enzymes, antibodies, antigens, lectins, neurochemical receptors, oligonucleotides, polynucleotides, polypeptides, molecules of DNA, molecules of RNA, proteins, glycoproteins, metalloproteins, cofactors, immunoglobulins, and other macromolecules of physiological significance including mixtures or active fragments or subunits thereof. The term biocatalyst may also be employed especially with reference to an enzyme, enzyme-complex or mixture thereof. In general, a broad class of ligand receptors may be immobilized and used in the present biosensors.

The steps comprising the method of this invention, as well as the materials disclosed which may be used to establish the discrete layered structures of the present microfabricated device, retain a surprising degree of flexibility and versatility such that a wide range of analyte species may be selectively examined. Furthermore, the microfabricated sensing device, or biosensor for short, is available for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. It should also be understood that solid or dessicated samples may be dissolved in an appropriate solvent to provide a liquid mixture suitable for analysis.

A second and related part of the invention is a means of photodefining optional additional layers over the active layer to protect it from contact with any deleterious components of the analytical sample or solution containing the analyte (i.e., the species to be analyzed or determined). In certain cases, such additional layers serve to attenuate the transport of the selected analyte into the biologically active layer, particularly when the selected analyte is present in high concentration in the sample. In so doing, the effective range of analyte concentrations in which the biosensor has a linear response is extended to higher values. Such analyte attenuation (AA) layers can also impair the responsiveness of the resulting sensing device and, therefore, their thickness must be carefully considered and controlled. Where the concentrations of selected analytes in the sample are not so great as to result in a nonlinear sensor response, such AA layers need not be established.

In certain embodiments of the invention, this AA or gas permeable layer, in addition to attenuating the transport of certain analytes or electroactive species, is also responsible for "insulating" the response of the sensor against the effects of sample turbulence or flow. Having a sensor response which is less sensitive to the external sample flow provides a more reproducible, reliable signal, and such a configuration is preferred particularly for the LLR-based biosensor embodiments described further herein.

Furthermore, a semipermeable solid film has also been discovered, which solid film may be established and patterned (photodefined) over preselected areas of a chemical sensing device. This permselective layer is able to act as a barrier against the intrusion of interfering electroactive species while the desired electroactive species may freely diffuse through said film. In a particular embodiment of this invention, the permselective layer is derived from a silanizing agent. Typically, a relatively stable silane precursor is dissolved or mixed in a solution which is able to hydrolyze at least two of the groups attached to the central silicon atom of the silane precursor. The resulting reagent solution is then established as a film across the wafer or localized over preselected areas of the wafer or base sensor. A semipermeable or permselective layer is then obtained under carefully controlled heating conditions. The permselective properties of the layer are governed, in part, by the thickness of the layer which is, in turn, dependent upon the nature and amount of silanizing agent employed as well as the method used to establish the film. Whenever desirable, mixtures of silanizing agents may be employed.

By eliminating most interfering electroactive species, fewer corrective measures are needed and the result is an operationally simpler device. Moreover, the base transducer, which frequently comprises a catalytic metal surface, may be heated in the presence of said permselective layer, to temperatures in excess of about 150° C. to about 250° C. This deliberate heating step provides an enhanced responsiveness of the base sensor to the primary electroactive species of interest (e.g., hydrogen peroxide or dioxygen) while maintaining the exclusionary nature of the solid film towards interfering electroactive species of higher molecular weight (e.g., uric acid or ascorbic acid).

In particular embodiments of the present invention, the transduction of the analyte concentration into a processable signal is by electrochemical means. These transducers may include amperometric, potentiometric, or conductimetric base sensors. However, the microfabrication techniques and materials of the instant invention may clearly be applied to other types of transducers (e.g., acoustic wave sensing devices, thermistors, gas-sensing electrodes, field-effect transistors, optical and evanescent field wave guides, and the like) fabricated in a substantially planar manner. A useful discussion and tabulation of transducers which may be exploited in a biosensor as well as the kinds of analytical applications in which each type of transducer or biosensor, in general, may be utilized is found in an article by Christopher R. Lowe in *Trends in Biotech.* 1984, 2(3), 59–65. The disclosures and descriptions contained in this Lowe article are incorporated by reference herein. Of the three electroanalytical techniques mentioned earlier, the potentiometric and amperometric techniques are preferred because the output signal may most easily be related directly to the response of the base sensor to a particular analyte. Specific examples directed to the production of potentiometric and amperometric type biosensors are found in the Examples Section of the present disclosure.

Herein are illustrated the various aspects of the invention which combine to yield a viable manufacturing process for an array of biosensors, for use in the analysis of undiluted biological samples. Preferred embodiments of an amperometric glucose sensor and a potentiometric urea sensor are described further. These sensors are useful for analyzing the concentration of glucose and urea, respectively, present in a given sample (e.g., venous blood). Various other sensors are likewise disclosed, including an embodiment especially adapted to perform immunology or affinity-based analyses, for the detection and measurement of analyte molecules of physiological significance, along with descriptions of modified configurations made possible by the present discoveries.

More particularly, this invention also relates to novel electrochemical assay procedures and to a novel wholly microfabricated LLR-based biosensor useful in determining the presence and/or concentration of selected biological (analytes) species of interest. This aspect of the invention relates to the discovery that a non-electroactive substrate (hereinafter the "substrate"), which does not undergo detectable electrochemical oxidation or reduction at an electrode at operating potentials which are accessible in aqueous based systems, but which undergoes a reaction with a substrate converter to form an unstable intermediate. The intermediate undergoes rapid auto-oxidation causing changes in the concentration of electrochemically detectable species. These detectable species include dioxygen and hydrogen peroxide. The changes are measured and related to the concentration of the analyte of interest.

Such novel assay procedures and LLR-based biosensor are useful in detecting the presence of, or monitoring the level of, one or more analytes in a mixture at a particular concentration, in the presence of potentially interfering substances. As mentioned previously the presence or absence of a particular analyte is determined from the extent of a specific binding interaction between an analyte and the first member (a capture receptor). The binding interaction, itself, is detected when a second member (the detection receptor), which is conjugated with a label (substrate converter), reacts with a substrate to give rise to the production and/or consumption (change in concentration) of detectable species (e.g., hydrogen peroxide or dioxygen); See FIG. 14. These concentration changes are electrochemically detected using the apparatus and assaying procedures of this invention. In particular embodiments of the present invention, labeled analyte species may also be employed in "competitive assay" procedures.

In a preferred embodiment of the present invention, a conjugated enzyme is used as the substrate converter (label) to effect a change in the concentration of the electroactive species. The enzyme may be conjugated to the analyte. Any change is detected electrochemically and related to the analyte of interest. In particular, the invention pertains to the preferred use of the enzyme alkaline phosphatase as the label and an indoxyl phosphate derivative as the substrate. However, it is apparent to one of ordinary skill in the art that the present invention is not so limited. In the general case, an esterase or hydrolase can be used to hydrolyze any indoxyl ester as long as the product undergoes rapid auto-oxidation. In yet other cases, the reaction of the enzyme with the substrate itself produces such a change in the concentration of electroactive species.

More particularly, but not exclusively, the invention is concerned with electrochemical immunoassay procedures and devices to determine analytes of interest. In this regard, an enzyme-labeled antibody or an enzyme-labeled antigen reacts with a substrate to effect a change in the concentration of electroactive species that is susceptible to electrochemical detection. In addition, since the enzyme-labeled antibody or enzyme-labeled antigen species is bound respectively to a complementary antigen or antibody species in a biological sample, the electrochemically detected enzyme reaction, therefore, provides for the qualitative or quantitative determination of species of interest. Specifically, this invention pertains to the reaction of the non-electroactive indoxyl phosphoric acid ester, which is the substrate, with an alkaline-phosphatase labeled goat antihuman Immunoglobulin G (antibody) or with an alkalinephosphatase labeled theophylline (antigen). These two reactions are associated with sandwich-type or competitive-type immunoassay methods, respectively.

It should be noted that the invention exemplified herein also extends to other assay systems. Theoretically, any ligand/ligand receptor pair in which at least one member can be immobilized onto the present biosensor can be incorporated into an assay procedure. Table II (Section 5.2.2) lists just a few examples of such ligand receptor/ligand pairs. Furthermore, other substrates, whose reaction with the label, or subsequent auto-oxidation, produces and/or consumes dioxygen or hydrogen peroxide may be readily contemplated. The invention is, therefore, not limited to the use of a phosphatase enzyme as the label, as already mentioned, because other hydrolases and labeling enzymes which are capable of reacting with a reagent to effectuate a change in the concentration of electroactive species are equally suitable (See, for example, Table II). Again, it must be stressed that, while the invention is described with reference to immunoassay procedures and with an immunological assay apparatus, it is also submitted that other types of specific binding reactions, such as those between other complementary binding species (e.g., enzyme/metabolite, lectin/polysaccharide, and nucleic acid oligomer/anti-oligomer) are also detectable employing the aforesaid electrochemical assay procedures and devices (See, for example, Tables II and III).

The present invention, therefore, provides processes and devices for performing simply and rapidly analytereceptor assays, for example immuno- and immunometric assays, which utilize an electrochemical sensor, and which do not require lengthy incubation steps. The electrochemical procedure and apparatuses described herein for the detection of phosphatase (label) activity are also highly specific and relatively sensitive. In addition, chromogenic and turbidimetric interferences are eliminated due to the nature of the detection system. The use of enzyme labels in the assay together with a non-electroactive enzyme substrate also potentially facilitates the extension of known specific binding assays to greater levels of resolution than those previously accomplished, usually without the requirement of pretreatment of samples to remove interfering substances. More particularly, the assay of an analyte in the nanomolar and above concentration range is thereby achieved.

5.1. Amperometric Glucose Sensor

The wholly microfabricated glucose sensor of the present invention comprises a silicon substrate on which is established thin-film structures which make up an amperometric electrochemical transducer, or base sensor. In a particular embodiment of the present invention, succeeding overlaid structures can be described as (i) a semipermeable solid film or permselective layer, superimposed over at least a portion of the base sensor, whose function is to promote the adhesion of succeeding layers over the base sensor and most importantly to prevent interfering electroactive species which are usually present in venous blood or other biological fluid samples from reaching the catalytic electroactive surface of the base sensor; (ii) a biolayer, superimposed over at least a portion of the permselective layer, in which is incorporated a sufficient amount of the bioactive molecule, in this case the enzyme glucose oxidase; and (iii) a layer responsible for attenuating the transport of the analyte species, in this case glucose, from the sample to the biolayer. The analyte attenuation (AA) layer thus limits the amount of glucose which reaches the enzyme to a given fraction of the bulk concentration of glucose in the sample.

The term "incorporated" as used herein is meant to describe any state or condition by which the material incorporated is held on the outer surface of or within a solid phase or supporting matrix. Thus, the material "incorporated" may, for example, be immobilized, physically entrapped, attached covalently to functional groups of the matrix, or adsorbed onto the porous surface thereof. Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule is "incorporated."

The succeeding overlaid structures are preferably confined to the locality of the electroactive surface of the indicator electrode of the base sensor. These structures may be localized by means of micro-dispensing or photolithographic techniques. An additional layer which comprises a photoresist cap may optionally be present over the AA layer as a consequence of the photoforming steps. This outermost cap can be established such that it does not act as a barrier to any species of interest, if any, and, therefore, need not be removed.

The basic chemical and electrochemical transformations on which the analytical value of the present device is premised include the convertion of glucose to gluconolactone by the action of the enzyme glucose oxidase (GOX):

$$\text{glucose} + O_2 \xrightarrow{\text{GOX}} \text{gluconolactone} + H_2O_2 \quad (1)$$

As indicated by Eq. 1, this transformation is accompanied by the concurrent reduction of dioxygen to hydrogen peroxide. Both dioxygen and hydrogen peroxide are electroactive species which can undergo redox reactions on the electrocatalytic surface of the indicator electrode of the base transducer. Other electroactive species (such as Na+, K+, Ca$^{2+}$, NH$_4$+, etc.) do not undergo a redox reaction per se but do promote a change in the potential at the electrode interface (See, e.g., the potentiometric device in Section 5.3). Thus, by applying the appropriate potential across the indicator electrode surface, with respect to a reference electrode, one of the following electrochemical reactions

$$O_2 + 4e^- + 4H^+ \longrightarrow 2H_2O \quad (2)$$

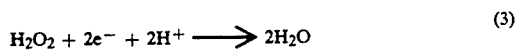

$$H_2O_2 + 2e^- + 2H^+ \longrightarrow 2H_2O \quad (3)$$

Figure 5:
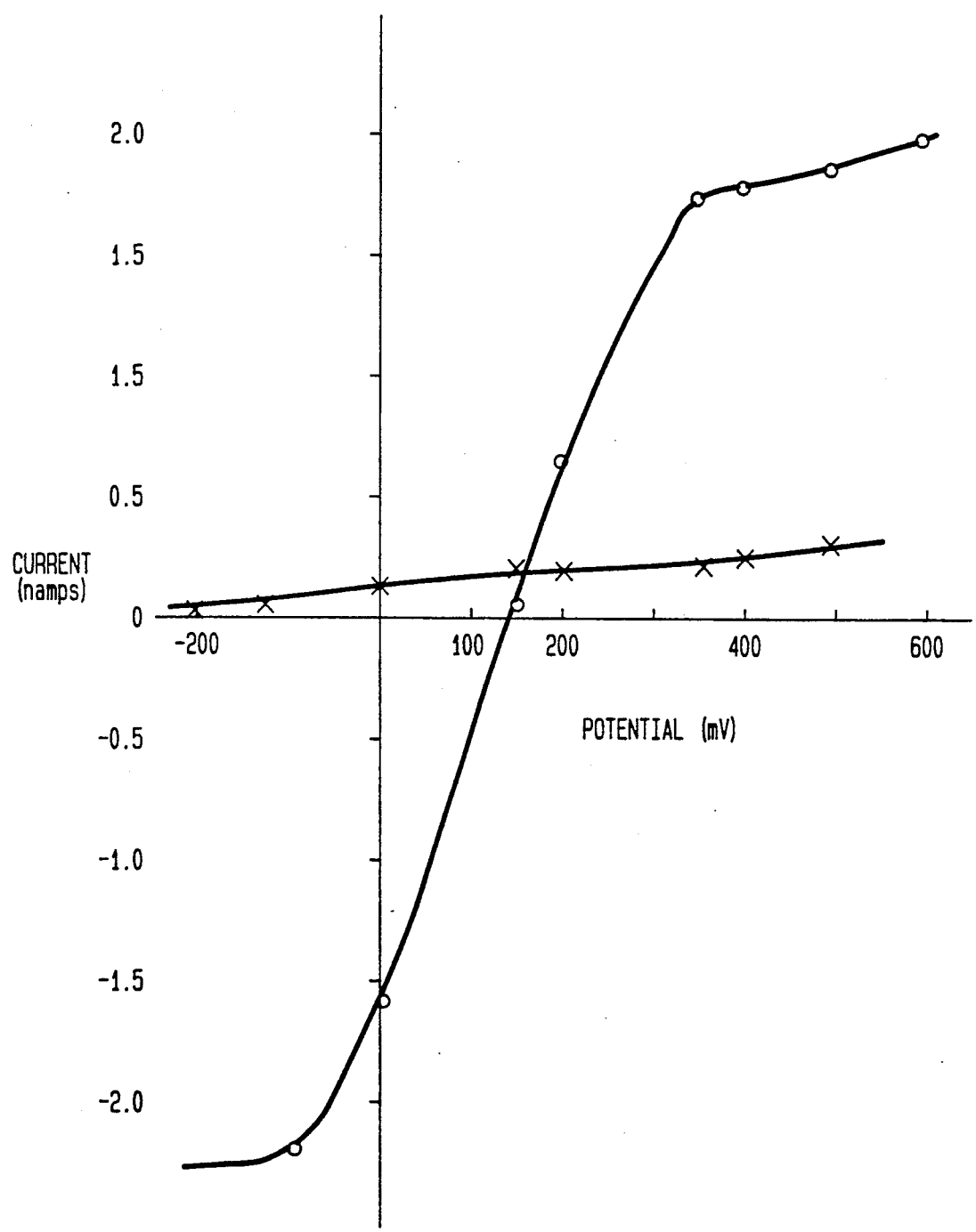

$$H_2O_2 \longrightarrow O_2 + 2e^- + 2H^+ \quad (4)$$

can take place, all of which result in the consumption of the electroactive species and the production of a measurable positive or negative current. Of the three reactions listed above, Eq. 4 is preferred in the present embodiment because it releases an equivalent of dioxygen per equivalent of hydrogen peroxide amperometrically measured. The dioxygen produced helps to maintain an adequate supply of dioxygen available for the enzymatic process of Eq. 1. The potential required for the oxidation of hydrogen peroxide is about +300 to about +600 mV, preferably +350 mV, vs. silver/silver chloride reference electrode. The current produced as a function of the indicator electrode potential of a glucose sensor of the present invention is illustrated in FIG. 5 for test samples comprising a HEPES buffer (X) and a 20 mM glucose solution in HEPES (Sigma Chemical Company) buffer (O). An increase in the current is observed as the indicator electrode potential is increased from 150 to about +350 mV for this particular glucose sensor. Further increases in the indicator electrode potential result in a nearly level response showing that, in the steady-state, the magnitude of the current produced is limited eventually by the amount of glucose analyte which is transported through the AA layer. This steady-state range extends from about +350 to about +600 mV as shown in FIG. 5. Conversely, a negative current is observed with a more negative indicator electrode potential as electrons are used up in the reduction of hydrogen peroxide to water (Eq. 3). Once again a limiting steady-state negative value for the current is reached at a certain negative potential (about −100 mV) and remains relatively constant through further increase in the negative value of the indicator electrode potential. One preferably operates the indicator electrode at the plateau to avoid large incremental changes in the current produced by small changes in the indicator electrode potential versus the reference electrode.

The current generated as a result of the preceding electrochemical reactions may be related ultimately to the concentration of glucose present in the sample. In an amperometric sensor, such as the glucose sensor, the measured variable (i.e., the current, i) is related to the flux of the electroactive species at the electrode surface (at a distance, x=0) by Faraday's laws, in combination with Fick's Law of diffusion (Eq. 5):

$$i = nFAD_p \frac{\partial [P]}{\partial x}\bigg|_{x=o} \quad (5)$$

where, n is the number of electrons involved in the fundamental electrochemical reaction at the electrode, F is Faraday's constant, A is the area of the electrode, and Dp is the diffusion coefficient of the electroactive species, P. In the steady-state, the rate of the enzymatic reaction in the biolayer is equal to the rate of supply of the glucose analyte through the AA layer. The degree of permeability ($Q_{AS}$) of the AA layer to the analyte species (AS) governs the upper limit of analyte concentration for which the sensor has a linear response, along with the activity of the enzyme, as measured by the Michaelis-Menton constant, Km. In the limiting case where both the amount of the enzyme and its activity are sufficiently high, the current can be controlled solely by the membrane permeability to the analyte, ($Q_{AS}$), and the bulk concentration of the analyte species, $[AS]_B$, as follows (Eq. 6):

$$i = nFQ_{AS}[AS]_B \qquad (6)$$

where i, n, and F have the same meaning as stated above. In effect, the steady-state current response is independent of the amount of enzyme activity in the enzyme layer. Such a condition enhances the operational stability and extends the useful shelf-life of the resulting biosensor.

5.1.1. AMPEROMETRIC BASE SENSOR

The amperometric base sensor that is a particular embodiment of the instant invention is fabricated on a substantially planar silicon substrate by means of photolithography in combination with the plasma deposition of metallic substances. The base sensor may comprise a unit cell containing two catalytic electrodes of identical geometry and area. This configuration allows a differential type of measurement because on only one of these catalytic electrodes is established a biolayer with active enzyme. Such a differential measurement may, in turn, enable the device to measure a current due to the activity of selected bioactive molecules over and above a background level, especially in circumstances where an interfering species may not be readily excluded by a permselective membrane.

Referring now to the accompanying drawings, FIG. 1 illustrates a preferred amperometric glucose sensor unit cell which is repeated in a geometric array several hundred times on a single silicon wafer. Each catalytic indicator electrode, 5 (iridium metal is used in this case), is surrounded by a combined reference and counter electrode, 4 (silver-silver chloride, in particular). The electrodes are each connected to one of three contact pads, 1, by means of an over-passivated signal line, 2. These contact pads serve as the means by which the biosensor is connected to external controlling electronics. The dashed area outlined by 3, represents the passivation layer. The permselective silane layer (functioning as an adhesion promoter and a semipermeable solid film), 6, can be present over the entire structure or, preferably, may be localized on the electrode portions of the unit cell. Over the iridium catalyst are successive overlaid structures: the biolayer or enzyme layer, 7; the AA layer, 8; and the outermost layer, 9, a photoresist cap.

Figure 2:
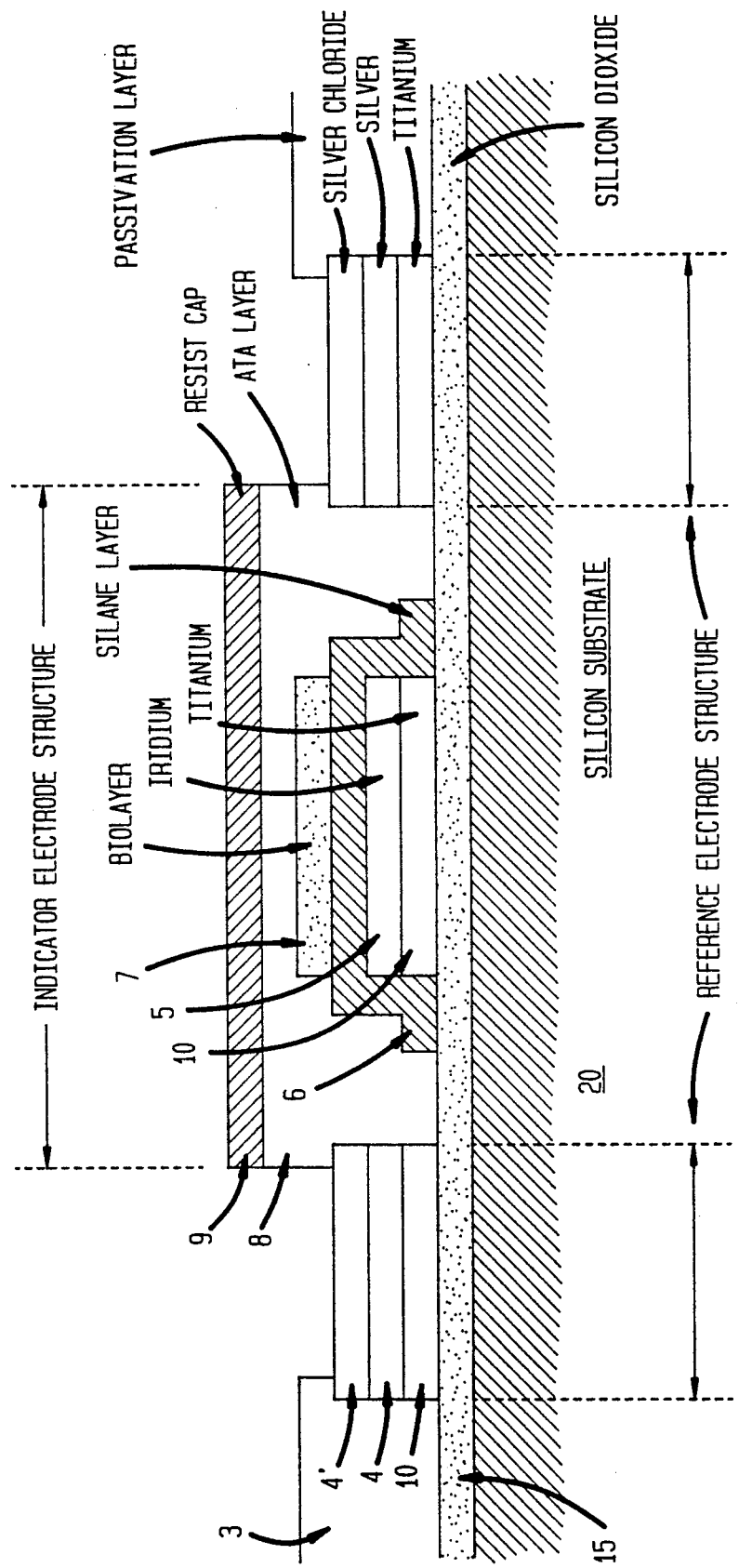

FIG. 2 illustrates the layered structures of one of the pair of indicator electrodes and the reference electrode portion of the preferred differential glucose sensor unit cell. The other member of the pair of indicator electrodes contains no active enzyme in the biolayer, 7. The substrate wafer, 20, is silicon, in this case, with a non-conductive layer of silicon dioxide, 15, present above it. Patterned titanium metal structures, 10, also serve as conducting signal lines to the contact pads of FIG. 1. The iridium electrocatalyst layer is indicated by 5 in the indicator electrode structure while silver and silver chloride are designated by 4 and 4', respectively, in the reference electrode structure. The polyimide passivation layer is 3 and the permselective silane layer (and adhesion promoter) is 6. Finally, 8 is the analyte attenuation (AA) layer (also, sometimes referred to as the gas permeable membrane elsewhere in this disclosure) and 9 is the photoresist cap.

Although the electrocatalyst is iridium in this particular embodiment, the catalytic metal of the indicator electrode may be made of any of the noble late transition metals. Hence, other metals such as gold, platinum, silver, rhodium, iridium, ruthenium, palladium, or osmium are also suitable. Other elements such as carbon or mercury are also useful. In another embodiment, involving a potentiometric type of electrochemical sensor, a mixed metal oxide alloy such as iridium tantalum oxide may also be used as the metal surface. In yet another possible embodiment, a dioxygen sensor is comprised preferably of a gold indicator electrode. Of these metals, silver, gold, or platinum is preferred as a reference electrode metal. A silver electrode which is subsequently chloridized is most preferred as the reference electrode.

These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E.M. *Palladium: Recovery, Properties, and Uses*, Academic Press, New York, N.Y. (1988); Wong, K. et al *Plating and Surface Finishing* 1988, 75, 70–76; Matsuoka, M. et al. Ibid. 1988, 75, 102–106; and Pearlstein, F. "Electroless Plating," *Modern Electroplating*, Lowenheim, F.A., Ed., Wiley, New York, N.Y. (1974), Chapter 31.) Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide or dioxygen. Doubtless, equivalent methods of establishing metal layers will be apparent to those skilled in the art.

In addition, the substantially planar substrate need not be a silicon wafer but can be a polished alumina wafer, glass sheet, controlled pore glass, or a planarized plastic liquid crystal polymer. In fact the planar substrate may be derived from any material containing one or more of a variety of elements including, but not limited to, carbon, nitrogen, oxygen, silicon, aluminum, copper, gallium, arsenic, lanthanum, neodymium, strontium, titanium, yttrium, or combinations thereof.

Additionally, the substrate may be coated onto a solid support by a variety of methods well-known in the art including chemical vapor deposition, physical vapor deposition, or spin-coating with materials such as spin glasses, chalcogenides, graphite, silicon dioxide, organic synthetic polymers, and the like. Additional substrates may include gallium arsenide, lanthanum gallate, neodymium gallate, or, less desirably, strontium titanate should the establishment of superconductive materials be deemed desirable.

In one of the initial steps of microfabrication, good metal-substrate adhesion can be promoted by etching the substrate wafer in an argon plasma prior to plasma deposition of titanium metal. The titanium layer serves as the conductive material for the signal lines and also promotes the adhesion of subsequent metal layers onto the substrate surface. The titanium is deposited at a rate of about 2 nm/sec, to a thickness of about 20 to about 500 nm, preferably about 80 nm. This step is followed by plasma deposition of iridium, at a rate of about 0.5 nm/sec to a thickness of about 10 to about 100 nm, preferably to about 20 nm. It is important to exclude dioxygen during metal deposition, since even traces of dioxygen lead to the formation of iridium oxide. Excessive amounts of the oxide provide an inferior sensor surface with a substantially increased capacitance and, therefore, a slower response.

It has been observed that even thin layers of a tenacious residue can reduce the metal surface activity significantly. In this respect, it is important to note that while nonmicrofabricated surfaces can often be reactivated by polishing the electrode with the aid of a slurry of an inert abrasive material, e.g., 0.3 $\mu$m particle size alumina powder (See, Sawyer, D.T. and Roberts, J.L. *Experimental Electrochemistry for Chemists*, Wiley, N.Y. (1974), p. 78), this treatment is incompatible with microfabricated electrode arrays. Hence, in a preferred method for the fabrication of the glucose sensor, it is essential that the polyimide passivation layer (3, in FIGS. 1 and 2) be processed *prior* to deposition of the catalytic electrode metal. Reversing the order of the processing can lead to the contamination of the catalytic metal surface.

Nevertheless, it has also been discovered that for the purposes of the present invention, passivation of the signal lines is an optional step. To obtain a device which has less topography (i.e., flatter, with fewer ridges), and one which facilitates the application of layers of materials by wafer spinning with the greatest degree of control, it may even be desirable to discard the polyimide or other passivation layer altogether. This omission is possible, perhaps, because of the observation that titanium, as the metal comprising the signal line, is a poor electrocatalyst for the redox conversion of the electroactive species (e.g., hydrogen peroxide, ascorbate, urate).

5.1.2. ADHESION PROMOTER AND SEMIPERMEABLE SOLID FILM

Another aspect of microfabrication which should be considered when depositing multiple layers onto a planar transducer of this type is the lack of "detailed" rough topography that would promote adhesion between component layers. Frequently, special materials are employed to promote adhesion to the underlying surface. A coupling reagent commonly used for this purpose is $\gamma$-aminopropyltrimethoxysilane. The silane compound is usually mixed with a suitable solvent to form a liquid mixture. The liquid mixture can then be applied or established on the wafer or planar sensing device by any number of ways including, but not limited to, spin-coating, dip-coating, spray-coating, and microdispensing. The microdispensing process can be carried out as an automated process in which microspots of material are dispensed at multiple preselected areas of the device (See, further Section 5.4, below). In addition, photolithographic techniques such as "lift-off" or using a photoresist cap may be used to localize and define the geometry of the resulting permselective film (See, Section 6.1.2, infra).

Solvents suitable for use in forming the silane mixtures include aqueous as well as water-miscible organic solvents, and mixtures thereof. Alcoholic water-miscible organic solvents and aqueous mixtures thereof are particularly useful. These solvent mixtures may further comprise nonionic surfactants, such as polyethylene glycols (PEG) having a molecular weight in the range of about 200 to about 6,000. The addition of these surfactants to the liquid mixtures, at a concentration of about 0.005 to about 0.2 g/dL of the mixture, aids in planarizing the resulting thin films. Also, plasma treatment of the wafer surface prior to the application of the silane reagent can provide a modified surface which promotes a more planar established layer.

Water-immiscible organic solvents may also be used in preparing solutions of the silane compound. Examples of these organic solvents include, but are not limited to, diphenylether, benzene, toluene, methylene chloride, dichloroethane, trichloroethane, tetrachloroethane, chlorobenzene, dichlorobenzene, or mixtures thereof.

When protic solvents or mixtures thereof are used, the water eventually causes hydrolysis of the alkoxy groups to yield organosilicon hydroxides (especially when n=1) which condense to form poly(organosiloxanes). These hydrolyzed silane reagents are also able to condense with polar groups, such as hydroxyls, which may be present on the substrate surface. When aprotic solvents are used, atmospheric moisture may be sufficient to hydrolyze the alkoxy groups present initially on the silane reagent.

The R' group of the silane compound (where n=1 or 2) is chosen to be functionally compatible with the additional layers which are subsequently applied. The R' group usually contains a terminal amine group useful for the covalent attachment of an enzyme to the substrate surface (a compound, such as glutaraldehyde, for example, may be used as a linking agent as described by Murakami, T. et al., *Analytical Letters* 1986, 19, 1973–86; and the article by Yao, T. referred to previously).

In the instant invention, it has been discovered that a film of a silane compound having the formula, $R'_nSi(OR)_{4-n}$, where n=0, 1, or 2, which has been heated to at least about 100° C., for a sufficient period of time, usually 5-15 minutes, can dramatically attenuate the transport of interfering electroactive species, ascorbic acid and uric acid, among others, to the electrocatalyst *without* significantly affecting the current due to the transport of dioxygen and hydrogen peroxide. In a preferred embodiment of the present invention, the R' fragment of the silane is a hydrocarbon radical comprised of 3-12 carbon atoms and R is a lower alkyl radical comprised of 1-4 carbons. In addition, the R' hydrocarbon fragment may further comprise at least one heteroatom such as an oxygen, nitrogen, phosphorus, or sulfur. Further, functional groups which represent stable combination of these heteroatoms, such as isocyanato, cyanato, phosphate, and the like may also be present. It may even be desirable in certain instances to employ an organosilane reagent in which the hydrocarbon fragment R' further comprises a suitable leaving group, preferably at the terminus of the hydrocarbon fragment. One example of such a silane reagent is 3-chloropropyltrimethoxysilane. In this manner, nucleophilic moieties may be covalently bound to the silane layer by displacement of the potential leaving group.

The lower alkyl radical, R, may be a methyl, ethyl, n-propyl, isopropyl, n-butyl, isobutyl, tertiary butyl group, or mixtures thereof. Routine experimentation will determine which groups are best suited to the particular manufacturing conditions being employed. Such factors as volatility, boiling point, and viscosity properties may be important considerations. The ease by which the alkoxy groups are hydrolyzed may also be dispositive. Also, because the —OR groups are substantially hydrolyzed in an aqueous environment, silane reagents in which R is also a hydrogen radical, is within the scope of the present invention.

Indeed, an important aspect of the present invention is the discovery and recognition that certain classes of silane reagents can be formulated into a convenient medium, established onto a substantially planar surface, and subsequently treated under controlled conditions to provide a layer or coating with permselective properties. It should be pointed out that prior to these observations, silane reagents were employed as mere adhesion promoters, on the one hand, or to establish impermeable glasses, at the other extreme.

Hence, freshly prepared alcoholic solutions of silicon hydroxides can be spun onto a wafer and heated to an intermediate degree such that the dehydration reaction which accompanies such heating produces a material having semipermeable properties. Although, the —OR groups of the silane reagent are preferably hydrolyzed (and later dehydrated), it should be pointed out that such hydrolysis is not always necessary. The thermal conversion of a tetraalkoxysilane to an intermediate form of silicon dioxide can be accompanied by the evolution of an ether compound.

It has been discovered further that replacing one or two of the alkoxy or hydroxy groups of tetrasubstituted siloxane with a group which is not readily hydrolyzed, such as a hydrocarbon moiety bonded directly to silicon, renders the resulting silane layers "more porous" than their "glassy" counterparts. Thus, for a given thickness, a layer derived from a silane of the formula $Si(OR)_4$ is less permeable than one obtained from a reagent of the formula $R'Si(OR)_3$. The increased permeability of the latter is, perhaps, best explained by the inferior ability of the $R'Si(OR)_3$ precursor to establish a network of oxo-bridged silicon atoms.

For optimum performance, then, the thickness and composition of the silane layer must be controlled. Such control is achieved by carefully selecting the identity of the silane reagent used, adjusting its concentration in the solvent mixture, and determining the proper rotation speed if the solution of the silane is deposited onto the wafer by spin-coating. Numerous silane compounds such as 3-aminopropyltriethoxysilane, N-(2-aminoethyl)-3-aminopropyltriethoxysilane, 3-aminopropyltrimethoxysilane, N-(2-aminoethyl)-3-aminopropyltrimethoxysilane, 3-isocyanatopropyltriethoxysilane, 10-aminodecyltrimethoxysilane, 11-aminoundecyltrimethoxysilane, 2-[p-{N-(2-aminoethyl)aminomethyl}phenyl]ethyltrimethoxysilane, n-propyltrimethoxysilane, phenyltrimethoxysilane, diethylphosphatoethyltriethoxysilane, or N,N-bis(2-hydroxyethyl)aminopropyltriethoxysilane, 3-chloropropyltriethoxysilane, are commercially available and may be processed in this manner to yield a semipermeable solid film which promotes adhesion of subsequent layers of other materials and yet is able to act as a small-molecule-selective membrane. As stated earlier, other materials used as preceramic or precursors to dielectric layers may also be used under proper conditions. Silicafilm products available from Emulsitone Company (Whippany, N.J. 07981) may be utilized. Examples of other silanes include tetrahydroxyorthosilicates (silicic acid) or tetraalkylorthosilicates such as tetramethyl, tetraethyl, tetrapropyl, tetrabutyl orthosilicates, or their mixtures. However, the preferred silane compound is N-(2-aminoethyl)-3-aminopropyl(trimethoxy)silane. The resultant sensor is easy to manufacture, has a very fast response time to changing hydrogen peroxide concentrations, and is substantially free of the signals resulting from interfering electroactive species.

As mentioned previously, the degree of permeability of the permselective silane membrane is due not only to the nature of the silane reagent but is also largely dependent on its thickness. A useful range of thickness lies in the range of about 1 to about 1000 nm, preferably between about 2 to about 20 nm. However, where one desires to substantially exclude molecules having a molecular weight of about 120 or more while allowing the effective diffusion of molecules having a molecular weight of about 50 or less, the preferred thickness of the silane layer, particularly when the preferred silane compound is used, should be in the range of about 5 to about 10 nm. The types of interfering electroactive species that one may wish to exclude from interacting with the metal catalyst surface include, but are not limited to, uric acid, ascorbic acid, salicylic acid, 2-(p-isobutylphenyl)propionic acid, cysteine, 4-acetamidophenol (acetaminophen), reduced glutathione, and the like, including their physiological salts in addition to any drug or metabolite thereof.

It has further been discovered that heating the planar wafer bearing the silane compound to a temperature in the range of about 150° C. to about 250° C., maximizes the subsequent indicator electrode response toward the oxidation of hydrogen peroxide. It is possible that at these higher temperatures, the surface of the electrocatalyst becomes more highly activated.

Separately, it is also advantageous to cycle the applied potential from positive to negative values before the actual sample is introduced. For the amperometric sensors such as glucose, the current signal that is measured may be small compared to the background noise. This condition may arise either from incomplete wet-up of the membrane layers or from deactivation of the electrode surface. It has been found that this signal-to-noise ratio may be increased by applying potential pulses to the electrode prior to making the measurement. Such a procedure can be conveniently carried out automatically by a suitable programmed sequence effected by the external electronics.

According to a particular embodiment for the instant glucose sensor, then, the iridium electrocatalyst is poised at a potential of +350 mV versus the silver-silver chloride reference electrode with a permselective silane layer is localized over the working electrode. As noted in Section 5.1.6, however, one configuration of the instant glucose sensor can be produced in which this permselective silane layer may be replaced by a gas permeable layer which preferably comprised a siloxane-nonsiloxane copolymer. As discussed infra such materials can be established at a sufficient thickness and can be localized over preselected areas of the sensor, chip, or wafer. Furthermore, different types of permselective layers may be utilized at different preselected areas of the sensing device. Such embodiments containing a gas permeable layer interposed between multiple photoresist layers are especially suitable for the LLR-based biosensors, described further below.

5.1.3. OVERLAID BIOLAYER

For the amperometric glucose sensor, the support matrix in which the biologically active molecule is immobilized is preferably photoformable in addition to providing a stabilizing environment for the biocatalyst. Most preferably, such a photoformable matrix behaves like a negative photoresist (although the methods are adaptable to positive resists) so that discrete structures may be applied and formed over predetermined areas of the transducer array; the biolayer is usually aligned with the iridium catalyst layer. Therefore, the support matrix material is first applied as a liquid solution in a suitable solvent, usually water, onto the wafer by spin-coating. The support matrix material may be about 0.02 $\mu$m to about 20 $\mu$m in thickness at this stage, preferably 0.1-2.0 $\mu$m. Alternatively, the layer may be applied in other ways including, but not limited to, dip-coating, spray-coating, or automated microdispensing. After deposition of the matrix film, the radiation-sensitive material is exposed to radiant energy (e.g., visible light, ultraviolet, infrared, X-ray, electron team, ion beam, and the like) through a patterning mask for a sufficient length of time to initiate the transformations necessary for fixing the exposed areas of the matrix to the wafer (in the case of a negative photoresist). The developing stage of the lithographic procedure usually involves exposing the irradiated wafer to further chemical reagents or solvents which ultimately results in the removal of unexposed matrix material while exposed areas remain fixed to the wafer.

It has surprisingly been discovered that hydrated proteinaceous substances which contain a sufficient amount of a photosensitizer (photoactivator or photoinitiator) are able to behave as suitable negative photoresist materials but in which a wide range of bioactive molecules may be immobilized or incorporated. It has also been found that these water-based photoformable multicomponent negative resist materials may also comprise various other components (sometimes nonproteinaceous) which modify the characteristics and properties of the resulting resist.

The proteinaceous substance of the resist mixture acts as a crosslinkable matrix, and the photoactivator serves to initiate the crosslinking reaction upon exposure to radiant energy. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to, albumin, casein, gamma-globulin, collagen and collagen derived products (e.g., fish gelatin, fish glue, animal gelatin, and animal glue). It is important to note that the photoformable proteinaceous mixtures of the present invention are comprised substantially of the protein-derived material. It is the proteinaceous material, itself which serves as the immobilization matrix brought about by the photoinitiated crosslinking reaction. This matrix is uniquely suited to act as a photodefinable membrane which also provides a very hospitable environment for the bioactive molecule.

The preferred substance is fish gelatin derived from the skin of Northern cold water fish, also known as "Teleostean Gelatin" (Sigma Chemical Co., St. Louis, Mo.). The multicomponent photoformable resist material may contain 0.01-50 g/dL fish gelatin solids, preferrably 0.5-10 g/dL. A wide range of high oxidation state transition metal compounds (salts, complexes, or chelates) can serve as a suitable photosensitizer. Representative compounds include, but are not limited to, ferric chloride, ferric ammonium citrate, ferric potassium citrate, ferric ammonium oxalate, ferric sodium oxalate, ferric potassium oxalate, ferric oxalate, ferric ammonium tartrate, manganese tartrate, potassium dichromate, and ammonium dichromate. The most preferred materials are ferric ammonium citrate and ammonium dichromate which may be present in the material at about 0.1-10 g/dL, preferrably about 1-2 g/dL. Alternatively, the photoactivator can itself be a multi-component system comprising a photosensitizing dye and a transition metal compound, preferably of high oxidation state. Virtually any photosensitive dye will do so long as the resulting photoactivated dye is capable of reducing a suitable transition metal compound. The photosensitizing dye may be a xanthine-based dye, such as fluoroscein (or a halogenated derivative thereof), eiosin, rhodamine, or methylene blue, and the like. The metallic component may include, but is not limited to, salts of $Pb^{2+}$, $Hg^{2+}$, $Ti^{4+}$, $Cu^{2+}$, $CrO_4^-$, $Ag^+$, and $MoO_4^-$ in which the appropriate counterion is preferably selected to confer solubility to the metal salt. For additional examples, please see Oster, G.K. and Oster, G. *J. Am. Chem. Soc.* 1959, 81, 5543-5545.

Although the mechanism is not completely understood, it is believed that radiant energy, such as UV light, initiates the reduction of the paramagnetic ferric ion to the ferrous form in the presence of suitable electron donors such as citrate ion (Eq. 7). Upon exposure of the ferrous ion to hydrogen peroxide in the developing solution, hydroxyl radicals are produced (Eq. 8) which, in turn, promote the crosslinking of the proteinaceous material, especially in the presence of added crosslinking agents, such as a polyunsaturated compound.

$$Fe^{3+} + h\nu + e^- \text{ donor} \rightarrow Fe^{2+} \tag{7}$$

$$Fe^{2+} + H_2O_2 \rightarrow Fe^{3+} + HO\cdot + HO^- \tag{8}$$

Again, not wishing to be limited by theory, it is believed that the chromium system works slightly differently in effectuating a change in the solubility of the protein material. One may speculate that exposure of the dichromate initiates the transformation shown in Eq. 9.

$$Cr_2O_7^{2-} + h\nu \rightarrow CrO_3 + CrO_4^{2-} \tag{9}$$

The chromate ion may then combine with functional groups of the gelatin to alter its solubility characteristics. In any event, the developing medium for the chromium system may be composed solely of water.

Additional compounds may be added to the resist material to modify its characteristics and properties. Crosslinkers such as N,N'-methylenebisacrylamide can be used to promote patternability. Other additives are listed in Table I. The preferred additive is N,N'-methylenebisacrylamide which may be at a concentration range of about 0.01 to about 10 g/dL, preferably about 1-2 g/dL. It is understood that the examples listed in Table I are not exhaustive and are not meant to limit the scope of the present invention. Furthermore, many other types of crosslinking agents maybe employed so long as two functional groups are present in the compound. The preferred functional group is a vinyl group. However, other groups which may be present include, but are not limited to, formyl, carboxyl, anhydride, amine, amide, epoxy, hydroxyl, cyano, isocyanato, thio, halo, or any stable combination thereof.

Polyhydroxylated compounds such as glycerol, and alcohol sugars, such as sorbitol, erythritol, and mannitol, may be added to the crosslinked matrix to promote the formation of a more open (porous) structure. Such porosity-altering substances may also include simple salts and may be used in combination with the polyhydroxylated compounds. Detergents may be added also to promote planarization of the matrix during spin-coating onto the wafer. Nonionic surfactant materials such as polyethylene glycol, Triton X-100, or reduced Triton X-100 may be used at a concentration of about 0.01 to about 1 g/dL, preferably at about 0.1 g/dL.

TABLE I

| Other Suitable Crosslinking Agents | | |
|---|---|---|
| Compound | MW | Structure |
| N,N'-Methylenebisacrylamide | 168 (n = 2) | |
| Dihydroxyethylenebisacrylamide | 204 | |
| Diallyltartardiamide | 232 | |
| Triallylcitrictriamide | 312 | |
| Ethylene diacrylate | 170 | |
| n-Polyethylene glycol diacrylate | 214 (n = 2) | |
| Bisacrylylcystamine | 262 | |
| Acetonebisacrylamide | 198 | |
| 1,1-Dimethylethylenebisacrylamide | 196 | |
| 2,2-Dimethylpropylenebisacrylamide | 210 | |
| Diacrylylpiperazine | 196 | |
| Diacrylylethylenedipiperidine | 306 | |

TABLE I-continued

Other Suitable Crosslinking Agents

| Compound | MW | Structure |
|---|---|---|
| 1,6-Heptadiene-4-ol | 112 | CH₂=CH-CH₂-CH(OH)-CH₂-CH=CH₂ |
| Acrylamide | 71 | CH₂=CH-C(=O)-NH₂ |
| Acrylic acid | 72 | CH₂=CH-C(=O)-OH |
| Acryloyl chloride | 90 | CH₂=CH-C(=O)-Cl |
| Acrolein | 56 | CH₂=CH-C(=O)-H |
| Acrylonitrile | 53 | CH₂=CH-CN |
| Acrolein dimethyl acetal | 102 | CH₂=CH-CH(OCH₃)₂ |

The biologically active component, or a mixture containing same, can either be pre-mixed with the negative photoresist (e.g., fish gelatin/ferric ammonium citrate) and co-deposited therewith or may be impregnated thereafter into the patterned support matrices. Where a wafer containing any array of identical sensors is required, spin-coating a negative resist is preferred since spinning offers the best dimensional control over the thickness of the layer. It may also be less wasteful, of course, if the biologically active component is impregnated into the already patterned structure. Where an array of different sensors is required in a single wafer, however, it is more effective to pre-mix each biologically active component with the negative photoresist and then microdispense the mixture at appropriate locations on the wafer. Alternatively, solutions of different biocatalysts may be introduced into each established support matrix. After all the mixtures have been dispensed, structures are then formed by a single patterning step. Microdispensing of the mixture is achieved by using an automatically controlled syringe with the wafer placed on an x, y, z - controlled vacuum chuck. The vacuum chuck may also be rotated slightly, if needed, to align the reference axis of the chip with the translational axis of the chuck. In general, microdispensing enough material to cover an area about three times the diameter of the catalytic electrode will dry to leave a substantially planar region directly above the catalytic electrode. Additional details of the automated microdispensing system are given in Section 5.4 and in FIGS. 12 and 13.

It should be evident to one of ordinary skill that variations of this technique may also be used to microdispense reagents other than biocatalysts. For example, reagents comprising adenosine diphosphata (ADP) and glycerol may be microdispensed in the vicinity of an ATP sensor, which reagents may be dissolved by an added fluid during the operation of the sensor. In addition there may be circumstances where the reagent cannot be exposed to the water-jets used to cool the dicing saw when the wafer is diced; that is, where the reagents comprise water soluble compounds, fragile membranes, etc., the wafer can either be partially diced (the dicing saw is used to score the wafer surface so that it can easily be broken along the score line after processing) or completely diced. In the latter method, wafer dicing using a commercial dicing saw (such as those supplied by Microautomations Inc., Santa Clara, Calif. or Kulicke and Soffa Industries Inc., Willow Grove Pa.) is performed with the wafer stuck on a flat plastic sheet in the center of a metal frame. When the wafer is diced completely the individual chips remain attached to the plastic. Thus, the step and repeat distances are maintained, and the microdispensing process can still be performed. This technique employing the plastic backing on a metal frame provides individual chips which have smoother edges than those obtained by breaking partially diced or scribed wafers. Consequently, better fitting assemblies, such as the disposable sensing device of the related and co-pending U.S. application Ser. No. 245,102, may be produced.

It has been discovered that such a microdispensed layer is almost as planar in the region above the base sensor after drying as that obtained by spin-coating. The thickness of this layer after patterning is controlled largely by the solids content of the resist, its viscosity, the surface energy of the substrate wafer, and the subsequent development time. With respect to the surface energy considerations, the surface can actually be tailored to spread the microdispensed material in a controlled manner. For instance, if the surface surrounding the indicator electrode is either polyimide or silicon dioxide, it can be made hydrophilic by exposure to an oxygen, water, argon, or nitrogen plasma. (A fluorocarbon plasma treatment makes silicon dioxide hydrophilic but a polyimide hydrophobic) (See, Section 5.4.1.3, below).

Of course, only those sections of the proteinaceous layer which are exposed to light, through the photolithographic mask, contain the reduced metal species. As mentioned previously, when an iron species is used as the high oxidation state metal, the irradiated wafer is then exposed to an aqueous developing solution which contains, among other components, hydrogen peroxide. The reduced metal species (ferrous ion, in this particular case) next interacts with the hydrogen peroxide present in the solution producing hydroxyl radicals. These radicals which are produced locally initiate the crosslinking reactions which serve to "fix" the proteinaceous matrix onto the exposed areas of the substrate wafer. Unexposed (uncrosslinked) portions of the proteinaceous layer are thus concurrently washed away. The reader is reminded that in another preferred embodiment, a dichromium system is useful as the photosensitizer. The mechanism of action of this system appears to be different from the iron system because plain water may be used effectively as the developing solution. Doubtless, other photosensitizing systems may be readily apparent to those skilled in the art which are consistent with the teachings and objectives of the present invention. Such equivalent photoinitiated means for "fixing" the proteinaceous matrix is naturally within the scope and spirit of the instant invention.

Surprisingly, it has been discovered that a number of enzymes are compatible with and are not inactivated or denatured by such negative photoresist-based processes. Examples of these enzymes include, but are not limited to, oxido-reductases with an organic cofactor, e.g., the flavoproteins: glucose oxidase, sarcosina oxidase, cholesterol oxidase, NADH oxidase, and glycerol-3-phosphate oxidase; oxidoreductases with a metal ion at the active site, e.g., uricase; hydrolases, e.g., creatirinase; and kinases, e.g., glycerol kinase and hexokinase. Other enzymes which may be immobilized within the proteinaceous matrix (or introduced subsequent to the establishment of the matrix structure) include, but are not limited to, urease, creatinine amidohydrolase, creatinase, creatine kinase, cholesterol esterase, glucose dehydrogerase, lactate dehydrogenase, alkaline phosphatase, alanine transaminase, aspartate transaminase, amylase, lipase, esterase, $\gamma$-glutamyl transpeptidase, L-glutamate oxidase, pyruvate oxidase, diaphorase, bilirubin oxidase, or appropriate mixtures of these and the above-mentioned enzymes. Additional macromolecules of biological significance, such as proteins, lectins, neurochemical receptors, molecules of deoxyribonucleic acid (DNA), molecules cf ribonucleic acid (RNA), polypeptides, glycoproteins, metalloproteins, immunoglobulins, cofactors, antibodies, antigens, receptors, ionophores, ion-exchangers, oligonucleotides, polynucleotides and mixtures, active fragments or subunits thereof, may also be immobilized by means of the negative photoresist process described herein. The above-mentioned substances must not be sensitive to brief exposure to ultraviolet light, dichromate ion, ferric ion, ferrous ion, crosslinking agents, or hydrogen peroxide (with certain photosensitizing agents), however, if they are to be present before the photoforming and subsequent development steps. Those that are denatured or inactivated under these conditions may be introduced subsequent to the patterning step as an aqueous solution, for example, as mentioned previously and further, infra.

The thickness and porosity of the preferred proteinaceous layer is important in controlling the final properties of the sensor. If the layer is too thick, the response will be impaired, and if it is insufficiently porous, the amount of enzyme which can be loaded into the structure will be too low. Generally, the proteinaceous layer may range in thickness from about 10 nm to about 0.5 mm, preferably about 0.05 to about 5 $\mu$m.

It should be noted that most biologically active macromolecules, including enzymes, generally degrade over time. Consequently, enough biocatalyst should be present in the immobilizing layer of the biosensor not only to provide the most favorable overall reaction rates but also to compensate for the amount of bioactive molecule (e.g., enzyme) which inevitably degrades over the period of time that the sensor is stored. Sensors manufactured with defects in the thickness or porosity of the proteinaceous layer will unavoidably have a limited shelf-life or useful lifetime, and will have impaired performance characteristics. It is therefore a crucial object of the present invention to provide a microfabrication process which is reliable and establishes overlaid biolayers in a reproducible and controllable manner.

Consistent with this objective, it has been discovered that the thickness of the layer can be controlled, among other things, by the content of solids in the negative photoresist, the spin speed, and the development time. On the other hand, the porosity of the crosslinked layer can be controlled, for example, by adding certain reagents to the negative photoresist which are radical scavengers (free-radical inhibitors) and can thus impede the degree of crosslinking. One such reagent is sorbitol. Other porosity-altering substances may include monosaccharides, disaccharides, oligosaccharides, polysaccharides, sugar alcohols, simple salts, or combinations thereof. Thus in a preferred embodiment of the present invention, the . photoformable gelatin layer is formulated to contain from about 0.01 to about 4 g/dL of sorbitol. It has been found that too much sorbitol, for example over 5 g/dL, results in a composition which undergoes very little crosslinking and is, therefore, not photoformable.

It should be mentioned that the porous characteristics of the immobilizing layer also aid in the initial "wet-up" stage of the operable biosensor. This stage involves the "wetting" and calibration of the biosensor which is stored essentially dry under a controlled humidity environment. Any structural features which speed up this process shortens the waiting time needed before the results are obtained.

By incorporating the bioactive molecules, or combinations thereof, described above and following the methods of the present invention, a broad scope of analytes may each be detected selectively and measured quantitatively in a given wholly microfabricated biosensor device. A representative group of analyte species of interest may include, although this list is by no means exhaustive, dissolved and total amounts of carbon dioxide, carbon monoxide, ammonia, dioxygen, ethanol, ionized calcium, sodium ion, potassium ion, lithium ion, hydrogen ion, chloride ion, magnesium ion, ammonium ion, hydrogen peroxide, ascorbic acid, glucose, cholesterol, uric acid, esterified cholesterol, urea, creatinine, creatine, triglycerides, lactate dehydrogenase, creatine kinase, alkaline phosphatase, creatine kinase-MB, alanine transaminase, aspartate transaminase, bilirubin, amylase, lipase, among others.

The biolayers of the present invention have utility in a wide range of applications in which a biologically active molecule is to be incorporated in the solid phase at preselected areas of a given device. Whether the biolayers are spin-coated across a surface, painted, screen-printed, dipped, or dispensed as microspots, they may be localized at strategic, precise areas by, for example, photolithography. Conceivably, these materials can be applied to any surface comprising part of a diagnostic system or kit, for example. The components of the test can be separated in different sections of the test surface and only later combined during the actual performance of the test. Such binary, ternary, or higher multicomponent systems can incorporate a chromogenic reagent which may then produce a characteristic color.

The film-forming latices may also be coated onto reactor beads, hollow fibers, or the inside walls of a bioreactor to promote the chemical transformation of reactive substrates. In addition, more than one number or one type of biolayer may be established to accomplish a series of transormations leading to the overall detection of a complex analyte like adenosine triphosphate, for example, or more than one analyte (e.g., cholesterol and glucose). Clearly, film-forming latices may be microdispensed, for instance, over proteinaceous layers. Alternatively, the reverse sequence, proteinaceous layers over microdispensed film-forming latices, may also be accomplished. A plurality of proteinaceous layers may also be established readily. Those skilled in the art can readily conceive of slight modifications or other applications of the present compositions which would follow quite naturally from the instant disclosures. Because of the broad utility of these compositions, such natural extensions are considered within the scope and spirit of the present teachings and are considered equivalents of the invention.

5.1.4. ANALYTE ATTENUATION (AA) LAYER

The sensor, thus far described, can function as a glucose sensor per se; that is, glucose solutions placed in contact with this device will produce a signal output (i.e., current) which is proportional to the concentration of glucose in the sample. In clinical practice, however, two limitations must still be overcome. First, such a sensor would have a response proportional (i.e., linear response) to the concentration of glucose in a sample over only a very narrow range of glucose concentration. Typically, this range spans about 0.1 to about 2.0 mM in glucose, hardly appropriate for the range of glucose concentrations (1–25 mM) encountered in fluid samples obtained from diabetic subjects, for instance. Second, the proteins, cells, and other components of whole blood, or any other biological fluid, would quickly foul such a sensor and prevent the uniform transport of analyte molecules. Although the blood sample may first be centrifuged or filtered to remove its heavier constituents, one would ideally, and most conveniently, wish to perform the tests on whole blood.

As already mentioned, the narrowness of the linear response range is due largely to the inherent biochemical properties of the enzyme employed in the functioning sensor described to this point. Such a sensor would not perform in the most ideal fashion in most clinical settings.

In the case of the glucose sensor, the enzyme glucose oxidase becomes saturated kinetically at a glucose concentration as low as 4 mM. As a consequence, the sensor provides no analytical information at higher analyte concentrations (i.e., the response becomes nonlinear, or even zero order). A possible solution to this problem of low saturation levels would involve providing some means for allowing only a certain, but constant, fraction of the glucose, or any other desired analyte, to reach the enzyme-containing layer without significantly attenuating the transport of the co-reactant dioxygen (Eq. 1). In other words, such a layer would tend to attenuate the amount of analyte reaching the biolayer but would also serve as a gas permeable membrane. If the fraction of attenuated analyte concentration is sufficiently low, the range of actual glucose concentrations which can be analyzed becomes much more desirable. However, because the amount of analyte, and hence the amount of electroactive species produced by the enzymatic reaction, is diminished, the current output must also necessarily decrease. The desirability of a linear response must, therefore, be carefully balanced against an overly diminished signal output.

In a particular embodiment of the present invention an additional layer of material, termed the analyte attenuation (AA) layer, is deposited over the enzyme-containing layer or biolayer. The thickness of the AA layer governs to a large degree the amount of analyte that reaches the active enzyme. Its application must, therefore, be carried out under strict processing conditions, and its dimensional thickness must be closely controlled. In other words, the AA layer must be established in a manner which is consistent with one of the primary objects of the instant invention. An AA layer which is too thin fails to provide a sufficiently linearized signal, while an overly thick layer is expected to reduce the current excessively and also slow down the response time of the sensor. In utilizing an AA layer, the problem of sensor fouling by extraneous materials is also obviated.

As in the microfabrication of the underlying layers, an important factor which affects close dimensional control over the AA layer is the composition of the AA material itself. In this regard, it has been discovered that several types of copolymers, for example, a copolymer of a siloxane and a nonsiloxane moiety, are particularly useful. These materials can be microdispensed or spin-coated to a controlled thickness. Their final architecture may also be designed by patterning and photolithographic techniques in conformity with the other discrete structures described herein. Examples of these nonsiloxane-siloxane copolymers include, but are not limited to, dimethylsiloxane-alkene oxide, tetramethyldisiloxane-divinylbenzene, tetramethyldisiloxaneethylene, dimethylsiloxane-silphenylene, dimethylsiloxanesilphenylene oxide, dimethylsiloxane-$\alpha$-methylstyrene, dimethylsiloxane-bisphenol A carbonate copolymers, or suitable combinations thereof. The percent by weight of the nonsiloxane component of the copolymer can be preselected to any useful value but typically this proportion lies in the range of about 40–80 wt%. Among the copolymers listed above, the dimethylsiloxane-bisphenol A carbonate copolymer which comprises 50–55 wt% of the nonsiloxane component is preferred. These materials may be purchased from Petrarch Systems, Bristol, Pa. (USA) and are described in this company's products catalog.

Other materials which may serve as AA layers include, but are not limited to, polyurethanes, cellulose acetate, cellulose nitrate, silicone rubber, or combinations of these materials including the siloxane nonsiloxane copolymer, where compatible.

In a preferred embodiment of the present invention, a solution of dimethylsiloxane-bisphenol A carbonate block copolymer in a mixture of chlorinated and aromatic solvents is spin-coated onto the wafer. Ethereal and carbonyl-containing solvents may also be used advantageously in the solvent mixtures. The thickness of this layer is controlled by the non-volatile content of the mixture and the spin-speed; its porosity to glucose is controlled also by the solvent composition. Examples of suitable solvents include, but are not necessarily limited to, diphenylether, benzene, toluene, xylenes, methylene chloride, trichloroethane, tetrachloroethane, chlorobenzene, dichlorobenzene, phenetole, 2-methoxyethylether, acetophenone, propiophenone, and cyclohexanone.

The AA layer thickness may be in the range of about 2 nm to about 10 μm, but is preferably between about 5 nm to about 10 nm for most applications. The thinner layers are most useful for the attenuation of low-molecular weight molecules (e.g., those having a molecular weight of about 100 to about 300). If the layer is sufficiently thick and cast from the appropriate solvent system, it can act as a gas permeable layer in which only gaseous molecules like ammonia, dioxygen, or hydrogen peroxide can permeate. It should be understood that the nature of the polymer film, along with its thickness, governs the dimensional threshold at which the analyte attenuation layer becomes a gas permeable layer. Depending on the particular polymeric material used, a given layer may function as a gas permeable layer at a lesser or greater thickness relative to another. Such routine experimentation to determine the useful range of thickness, for a given function of a given material, is deemed within the capability of a person skilled in the art. Generally, for the preferred materials, certain layers with a thickness of about 5-1000 nm can function as an AA layer, whereas some layers having a thickness of about 100-5000 nm would function as a gas permeable membrane. Hence, some overlap in the thickness ranges is to be expected.

An important aspect of the establishment of the AA layer is the successful patterning of the polymer layer without deleteriously affecting the function and performance of the underlying layers, particularly the activity of the enzyme should a biolayer be present underneath. It is desirable to localize the area covered by the AA material and to remove it from regions of the wafer where it would interfere with other functional aspects of the sensor. The contact pads, 1 (FIG. 1), for example, must be unhindered in their ability to make electrical contact with a microprocessor unit.

To pattern the AA copolymer layer, a gelatin-based negative photoresist, similar to that employed for the enzyme-containing layer and known as NPR 6, is spin-coated over the polymer layer and patterned to leave a photoresist cap only in locations where the AA copolymer is required. This negative photoresist is available commercially from Norland Products Inc., New Brunswick, N.J. Excess AA copolymer can then be removed by exposure to a basic etchant which may be comprised of an alcoholic solution of potassium hydroxide or tetramethyl ammonium hydroxide. It has been discovered that the resist cap does not affect the response of the glucose sensor and, therefore, its subsequent removal is optional. Clearly other aqueous-based photoresists known to those skilled in the art could also be used to pattern the AA layer.

Figure 6:
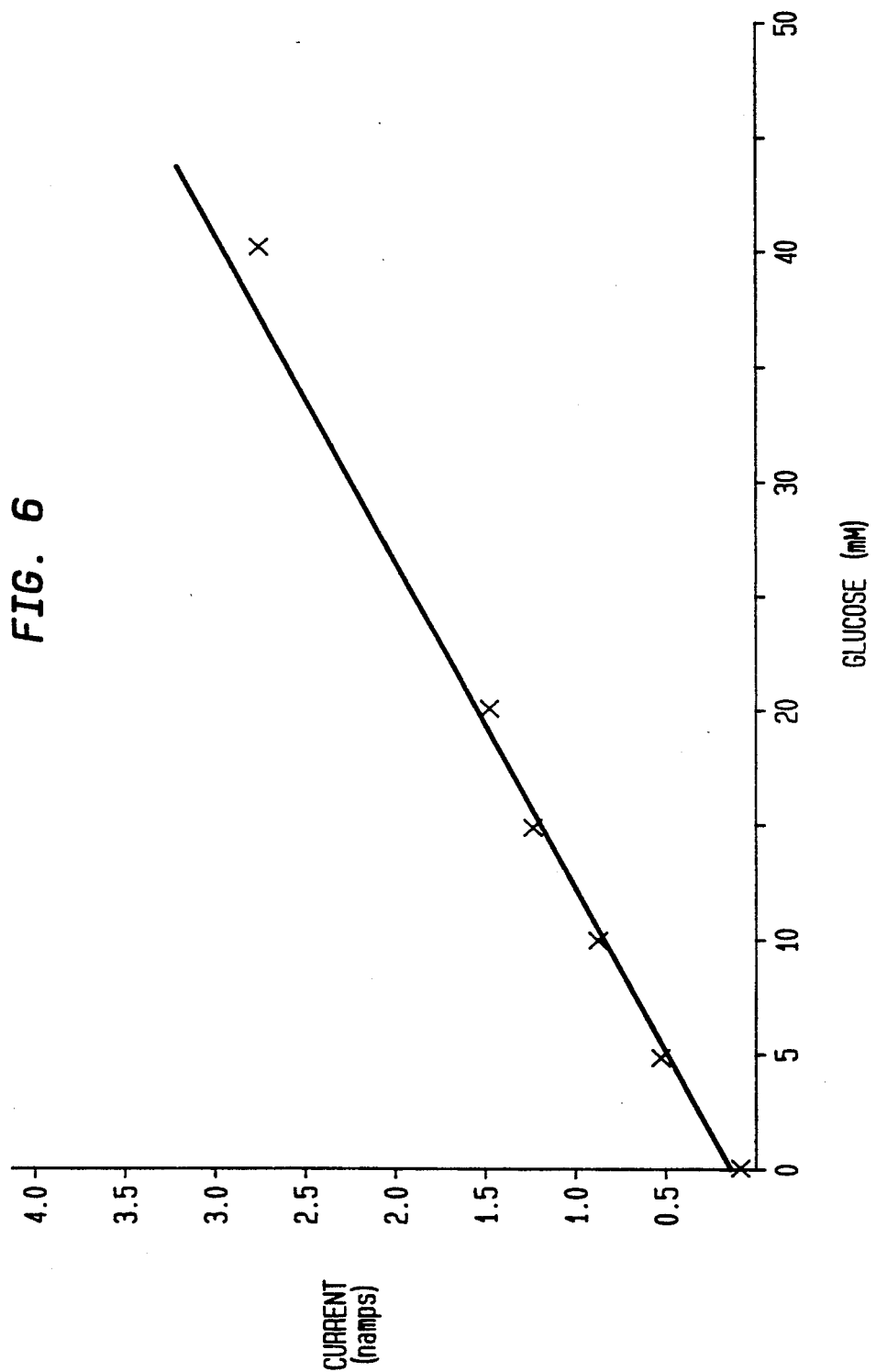

Referring now to FIG. 6, one can see that the response of the glucose biosensor as disclosed herein is linear over a much wider range of glucose concentration due to the presence of the AA layer. Without the AA layer, the sensor would have been less appropriate for use in undiluted biological materials.

5.1.5. FINISHING STEPS AND ADDITIONAL EMBODIMENTS

The final step in manufacturing the device involves dicing the wafer to yield individual glucose sensors. This step may be conveniently performed by an automated machine with a diamond-impregnated rotating saw-blade and which is equipped with a means for delivering water jets to cool the blade and to remove swarf and the like. This relatively drastic step is capable of effectively destroying all but the most robust thin-film structures which are present on the substrate wafer. Of particular significance in the present invention is the discovery that this step can, in fact, be successfully performed on the embodiments of the glucose sensor as described herein without a deleterious effect on the selectivity, sensitivity, and overall performance of the sensor. The disclosures of the present invention represent, therefore, a true microfabrication manufacturing process which can be utilized in the production of identical microcomponents useful as sensors for analyte molecules of physiological, biological, and medical significance.

In some instances, nevertheless, it may be preferable to "scribe" the wafers with the automated rotary saw prior to establishing the structures which comprise the bioactive layers of the chemical sensor. This process involves a partial dicing step which outlines each individual sensor on the wafer. The scribing process facilitates a final cleaving step at the end of the manufacturing process but still leaves the scribed wafer with sufficient structural integrity to endure the intervening process steps. The scribing process is described in more detail in the Examples section of this disclosure.

Additional types of chemical sensors based on the proteinaceous photoresist immobilizing layer are described in the Examples section. Most of these examples involve amperometric devices which utilize an electroactive species (e.g., hydrogen peroxide or dioxygen) generated from an enzyme-catalyzed reaction involving an analyte molecule and some cofactor. Among the specific embodiments given is a means for microdispensing a mixture containing the enzyme uricase onto a sensor, followed by patterning the resulting thin film to yield a uric acid sensor. In addition, a combined glucose and cholesterol sensor may be coprocessed by microdispensing two mixtures on the sensor, one containing glucose oxidase and the other containing cholesterol oxidase and cholesterol esterase. An example of an adenosine-5'-triphophate (ATP) sensor which involves the co-immobilization of more than one enzyme is also given. This process is achieved by microdispensing a mixture comprised of glycerol kinase and glycerol-3-phosphate oxidase. These examples are illustrative of the generality of the microfabrication process of the instant invention and demonstrate the broad scope of chemical sensors which may be fabricated limited only by the availability of suitable catalysts (e.g., enzymes) and/or reagents (e.g., adenosine diphosphate, ADP), needed for a specific chemical transformation.

5.1.6. AN AMPEROMETRIC DIOXYGEN SENSOR, ELECTROLYTE LAYER, AND ALTERNATIVE PERMSELECTIVE LAYER

As alluded to in numerous parts of this disclosure, the specific embodiments described herein enjoy great flexibility depending upon the particular application or analysis to be performed. For instance, the preceding discussion concentrated on the utility of the hydrogen peroxide sensors when coupled to biocatalyst systems which consume the neutral or charged analyte species and concommitantly produced $H_2O_2$. However, in certain situations, the change in the concentration of dioxygen may be a more convenient variable to monitor.

Figure 7B:
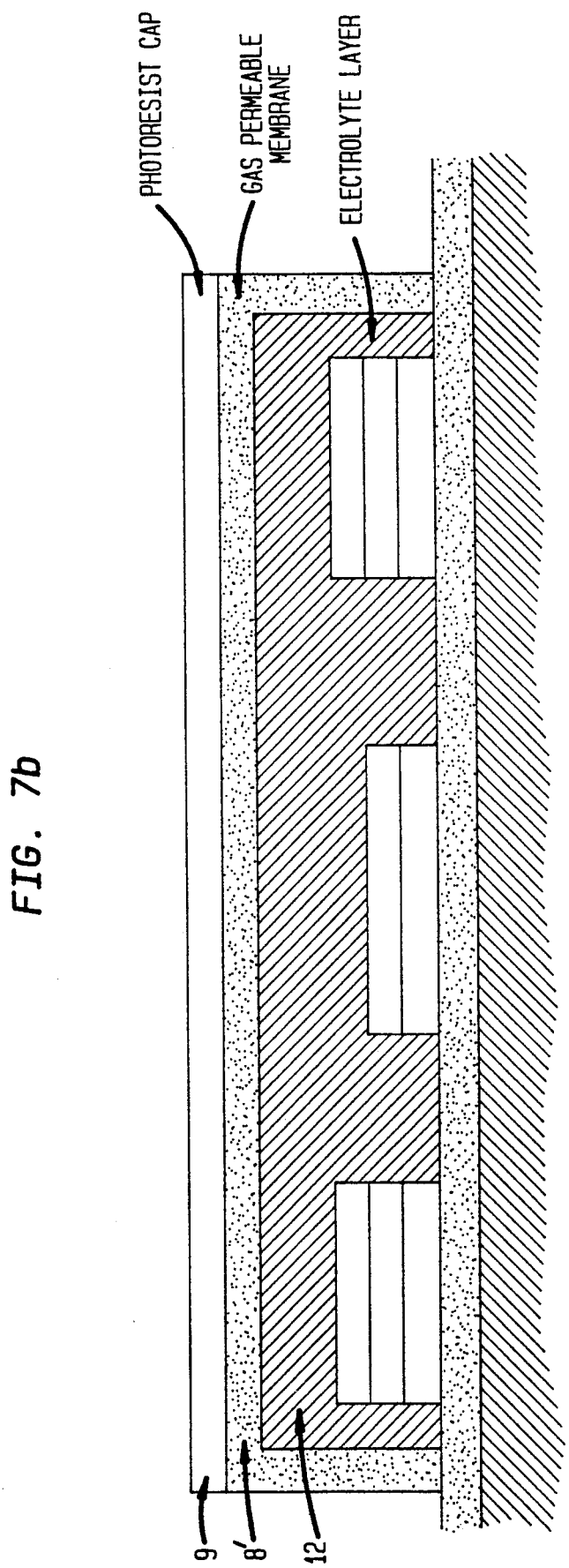

A skilled practitioner in the art recognizes that dioxygen is consumed in many enzymatically catalyzed processes. Thus, one could monitor, in the alternative, the decrease in the amount of dioxygen present in a sample as a consequence of the enzymatic action on the enzyme substrate or analyte species. In one embodiment of a dioxygen sensor, the base sensor is comprised of a gold indicator electrode superimposed over the primary titanium layer as shown in FIG. 7. The metallic components of the dioxygen base sensor are as illustrated in the figure and resemble closely the hydrogen peroxide sensor depicted in FIG. 2 except that the preferred electrocatalyst metal 5 is gold in this case. The overlaid structures in FIGS. 7A and 7B are essentially the same comprising, in succession, an electrolyte layer 12, a gas permeable layer 8', and a photoresist cap 9. The principal distinction is that the gas permeable layer 8' effectively envelopes the entire underlying electrolyte layer in the configuration of FIG. 7B, and, thus, more effectively seals off the electrode region from the external fluid. However, such a structure would be expected to take a longer time to "wet-up" relative to the architecture of FIG. 7A. The preferred materials for use in the electrolyte layer and photoresist cap are the photoformable proteinaceous mixtures described herein. The gas permeable membrane/AA layer is preferably formed using the siloxane/nonsiloxane copolymers described previously.

From a processing point of view, it is noteworthy that the configuration of FIG. 7A can be established using a single photoexposure step in which the photoinitiated crosslinking reaction can take place both in the underlying electrolyte layer and the overlaid photoresist cap. The structure of the dioxygen sensor of FIG. 7B, on the other hand, would require a first exposure to radiant energy followed by the developing step to form the underlying electrolyte layer. The AA material would then be established followed by the photoresist cap. The final structures are then localized over the preselected areas by a second exposure through a photolithographic mask, then developed in the appropriate developing solution. In the single exposure method, it should be remembered that the conditions of irradiation can be adjusted such that all of the sensitive layers receive an appropriate exposure to provide photocrosslinked matrices. This penetrating irradiation step is only possible, however, where the intervening layers (in this case, the gas permeable layer) do not significantly absorb the radiant energy. Thus, preferred materials for use in the AA layer should not be strongly absorbing in, say, the ultraviolet region of the electromagnetic spectrum. Such preferred materials are the siloxane/nonsiloxane copolymers, for example.

Two additional aspects of the dioxygen sensor embodiments are noteworthy. First, the gas permeable layer can be established at a thickness such that only small gaseous molecules, like dioxygen, can effectively reach the electrode portions of the sensor. Therefore, interfering electroactive species may be substantially excluded from the electrocatalyst surface in this manner. The gas permeable layer thus performs the same permselective function as the permselective silane layer and can be used for that purpose, in the alternative. Second, the electrolyte layer surrounding the electrode structures, in cooperation with the other overlaid structures, provides a "stagnant" environment, in terms of external turbulence, within which the redox reactions can take place on the metal surfaces. Put another way, the amount of redox species reaching the electrode surface is governed by the presence of the gas permeable and electrolyte structures such that the electrode response is independent of the flow or turbulence characteristics of the external fluid sample. Furthermore, the electrolyte layer, which is hydrated under normal operating conditions, is able to provide protons for the redox reaction of dioxygen. The resulting multi-layered device is much more reliable and able to provide more accurate and reproducible measurements relative to a bare metal electrode configuration.

Figure 8A:
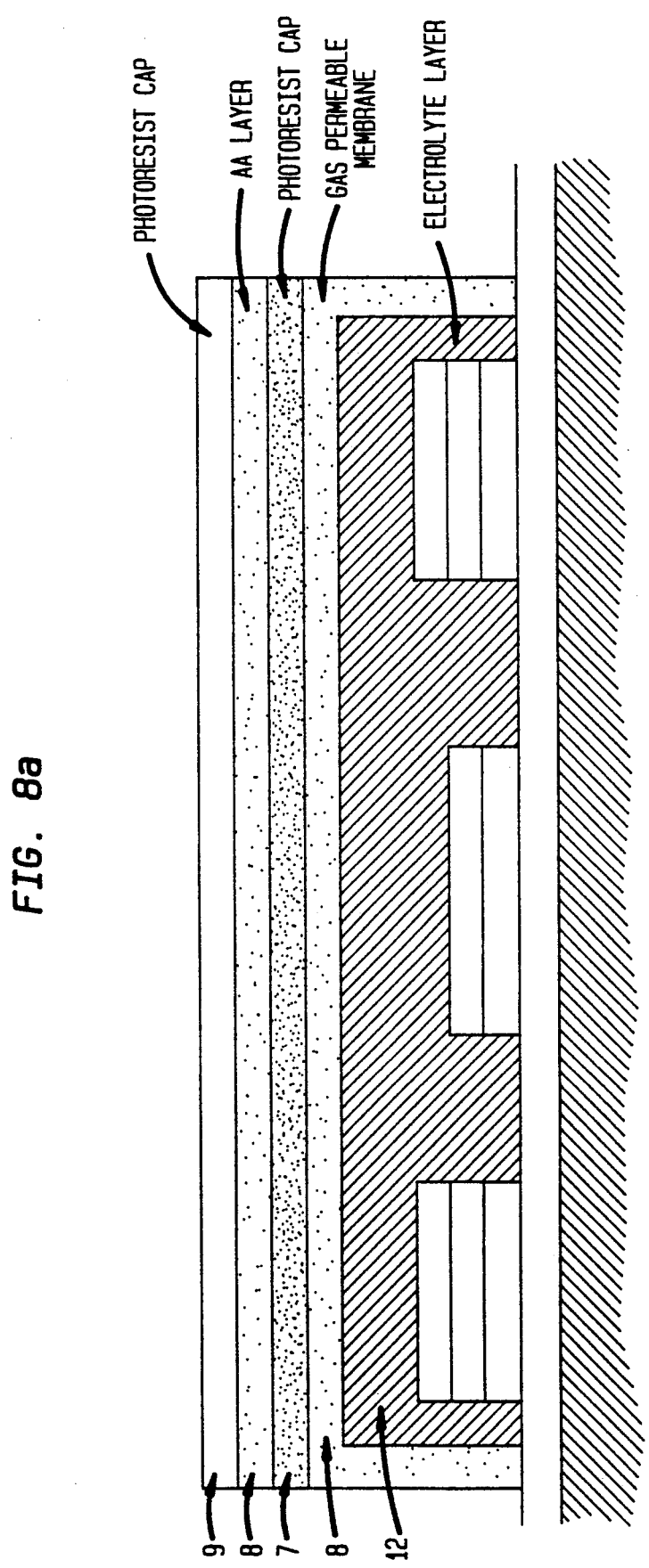

The structures illustrated in FIG. 8 embody these latter aspects of the present invention. In FIG. 8A, the biolayer, 7, is superimposed over the underlying gas permeable layer of a dioxygen sensor as in FIG. 7. The AA layer 8 and photoresist cap 9 are established over the biolayer as described previously. If the bioactive molecule present in the biolayer is glucose oxidase, then the resulting device is able to function as a glucose sensor, with the gas permeable layer performing a similar function as the permselective silane film described earlier.

Figure 8B:
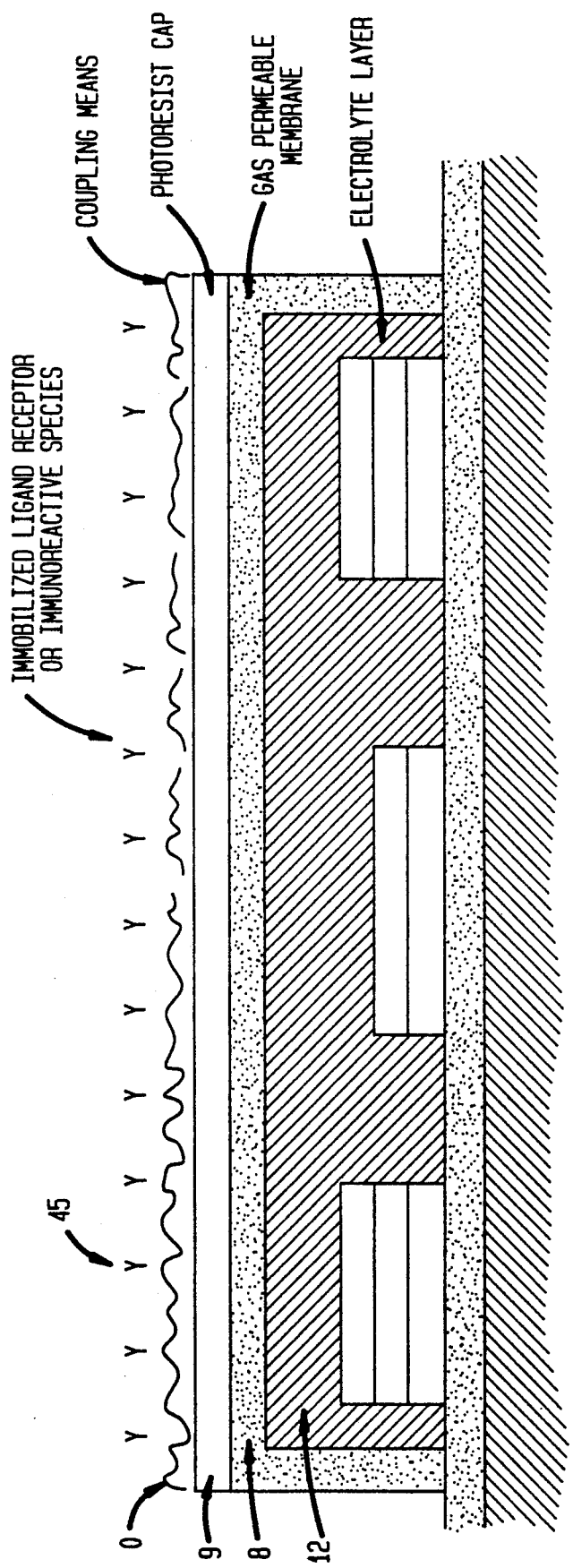

The structures of FIG. 8B, on the other hand, illustrates a device which is described further in Section 5.2, but which takes advantage of the underlying electrolyte and gas permeable layers (12 and 8', respectively) against external fluid turbulence or sample flow. In this device, a coupling means, 40, is used to covalently attach a ligand receptor or immunreactive species, 45, to the outermost surface of the layered structures (e.g., to the top of the photoresist cap, 9). As disclosed further, infra, such a device is useful as a ligand/ligand receptor-based (LLR) biosensor which expands considerably the range and scope of possible analyte species which may be detected or analyzed by the wholly microfabricated biosensor devices of the present invention, without being unduly sensitive to the movement of the external fluid samples.

5.1.7. PERFORMANCE OF THE GLUCOSE SENSOR

FIG. 5 shows the steady-state current for glucose as a function of the operating potential of the glucose sensor with respect to the on-board silver/silver chloride reference/counter electrode for a solution containing HEPES buffer 50 mM (pH 7.4) containing 100 mM NaCl (O) and the same solution containing 20 mM glucose (X). At potentials between $+300 - +600$ mV the current is associated with hydrogen peroxide oxidation at the iridium electrode surface derived from the enzymatic oxidation of glucose by the enzyme glucose oxidase. At potentials between $-200$ to $-100$ mV the current is derived from the reduction of hydrogen peroxide at the iridium electrode surface. The observation of a plateau current for both the oxidation and reduction of hydrogen peroxide suggests that the biosensor current is limited by transport of glucose through the AA layer into the enzyme layer, as discussed earlier.

FIG. 6 shows a calibration curve for the glucose biosensor in which the steady-state current measured at $+350$ mV is plotted as a function of glucose concentration. The response is linear in the range 1–30 mM glucose. Additional experiments demonstrate that the current response is not significantly effected by: (i) changes in pH over the range commonly encountered in biological fluids e.g., pH 6.8–8.2; (ii) changes in the partial pressure of dioxygen over the range 20–200 mm Hg; or (iii) changes in chloride ion concentration over the range 50–200 mM. The glucose biosensors, indeed, any of the biosensor embodiments of the instant invention may be used in conjunction with the devices which are the subject of co-pending U.S application Ser. Nos. 245,102 and 187,665 (the complete disclosures of which are incorporated by reference herein) to perform measurements of glucose or other analyte levels in biological fluids such as human plasma, serum, or whole blood.

5.2. Ligand/Ligand Receptor-Based Biosensors Adapted for Conducting Biological Assays or Chemical Testing In another embodiment of the present invention, the microfabricated biosensors may be adapted for performing analyses based upon intermolecular affinity and/or immunochemical complex interactions. Such interactions are manifest in numerous complementary ligard/ligand receptor complexes such as antigen/antibody, antibody/anti-antibody, biotin/avidin, immunoglobulin G/protein A, enzyme/enzyme receptor, hormone/hormone receptor, substrate/enzyme, DNA (or RNA)/complementary polynucleotide sequence, drug/drug receptor, and the like. Thus, an assay may be devised in which one or the other member of the complex may be the analyte species of interest, and the other component may be used as the sensor-immobilized ligand receptor or immunoreactive species.

Generally, a first member (e.g., the ligand receptor) is immobilized (e.g., by covalent attachment or adsorption) over a preselected area of the biosensor (preferably, above the indicator electrode). Next, the ligand or analyte species is allowed to bind to the first member, forming an affinity, immuno, complementary, or like complex. Depending upon the assay method employed (e.g., a sandwich assay), a second member with a suitable label is then introduced and binds to the analyte. Finally, a substrate for the enzyme label is introduced which is converted by a process initiated by the label. In such a fashion, electroactive species, such as dioxygen or hydrogen peroxide, are generated (or consumed), and the quantitative amounts of which are detected advantageously by the underlying base sensor. The second member and the substrate may be collectively referred to as reagents with which the sample suspected of containing the analyte species may be treated or combined. Such reagents may further comprise other components which may enhance the interaction of the reagent or reagents with the analyte species or to amplify the change in the concentration of detectable species so produced.

In an embodiment of the instant ligand/ligand receptor-based (LLR-based) biosensor, the first member may be immobilized by covalent attachment to a functionalized silane layer, with or without the benefit of a crosslinking agent (e.g., glutaraldehyde, epichlorohydrin, and others). Preferably, the immunoreactive species or ligand receptor is covalently bound to the outermost layer of a sensor having a structure of the type illustrated in FIGS. 7 or 8. Such a configuration would possess all the advantages attendant with the presence of the overlaid structures as explained earlier in Section 5.1.6. Again, the base sensor may be predisposed to hydrogen peroxide (e.g., iridium) or dioxygen (e.g., gold).

The exact assay procedure used is a choice which can be made by one skilled in the art and can be a procedure based, for example, on existing sandwich assays, competitive assays, or the like. Where the base sensor is an electrochemical sensing device, the instant embodiment is particularly useful in the qualitative and quantitative measurement of analytes which are of interest in immunology or substance detection.

5.2.1. AN LLR-BASED BIOSENSOR ADAPTED FOR IMMUNOASSAYS

As a particular illustration of an LLR-based biosensor that uses procedures based on existing sandwich assays, one can take a specific case in the general area of antigenic substance/antibody interactions. The presence of a particular analyte species, such as a particular antigen, may be detected, for example, by immobilizing an antibody (first member), capable of binding to the specific antigen of interest, onto the base sensor of the present invention. The resulting LLR sensor is then brought into contact with a mixture comprising the sample, in which the presence of the antigen is to be determined, and a second antigen-specific antibody (second member) which is labeled suitably. The action of the "label" on a chemical substrate, subsequently added, initiates a process by which the measurement of the analyte species is effected. Alternatively, the antigen (first member) may be immobilized on the base sensor, and the antigen-specific antibody may be the analyte species. A second member, comprising an anti-antibody, may then be present to bind to the analyte species. This second member would also be "labeled" with an enzyme, such as alkaline phosphatase. An enzyme substrate is then introduced.

As described earlier, the antibody or antigen may be attached non-covalently (e.g., by adsorption) or attached covalently, directly or through an intermediate crosslinking reagent, to functional groups present on the silane layer. In one example, a photoresist cap may also be present which photoresist cap is preferably comprised of a proteinaceous substance. As such, the proteinaceous substance also possesses a multitude of reactive functional groups, notably amino and carboxylate groups, to which the first member of the assay may be bound covalently.

The base sensor may be selected from an amperometric electrochemical device to which the applied potential allows the electrochemical conversion of hydrogen peroxide or dioxygen. Preferably, antibody is immobilized via any coupling means well-known in the art to the outermost layer of the preferred dioxygen sensor, which outermost layer comprises a proteinaceous substance or mixture thereof, and aligned over the indicator electrode, to provide a structure such as that illustrated in FIG. 8B.

In another embodiment of the present LLR-based biosensor, a hydrogen peroxide base sensor with an overlaid permselective silane layer (also acting as an adhesion promoter) is manufactured as already described in the preceding sections. The permselective silane layer is useful as a screen against interfering species which may otherwise come into contact with the base sensor and which may interfere with the analysis during incubation of the appropriate reactive components, including the test sample. Preferably, the silane layer is confined to preselected areas of the base sensor.

The substrate wafer bearing the silanized base sensors, or other electrolyte/gas permeable layers, is preferably "scribed" (as described in Section 5.1.5) before the layer of immunoreactive species is established. The scribed wafer can then be exposed to a solution of glutaraldehyde, or any other suitable crosslinking reagent known to the skilled practitioner, and subsequently to a solution of the desired first member. The resulting wafer may then be cleaved to provide individual chips or devices.

(It should be noted that the term "substrate", as used generally in the art and in this disclosure can refer to one of two substances. Where the base sensor is the subject of the discussion, "substrate" refers to the substantially planar surface or wafer which forms the foundation of the transducer. When the context of the disclosure is focused on an enzymatic process, "substrate" refers to the chemical species which is transformed by that enzymatic process.)

5.2.2. METHODS FOR PERFORMING ELECTROCHEMICAL ASSAY PROCEDURES

The electrochemical assay procedures of the invention relate to many analytes of interest. Such assay procedures involve sandwich and competitive assay procedures using this invention's novel biosensor, which is an electrode described in detail infra, to detect changes in the concentration of electroactive species.

In the operation of a sandwich assay, a solution is prepared which possibly contains the analyte of interest and a second member (detection receptor), which is labeled with a substrate converting moiety. If the analyte of interest is present, then the second member and the analyte form a complex. The sandwich assay also uses an LLR-based biosensor on which is immobilized a first member ,capture receptor of the analyte). The complex obtained from the analyte and second member is brought into contact with the biosensor to form a capture receptor/analyte/detection receptor complex on the biosensor. Following the formation of this complex on the biosensor, the biosensor is washed to remove other components of the solution which are not complexed to the biosensor. The biosensor to which the complex is bound is then placed in contact with a non-electroactive substrate whereby the label of the second receptor reacts with the substrate. This reaction ultimately (i.e., directly or indirectly) initiates a sequence of steps which effectuate changes in the concentration of electroactive species (i.e., produces hydrogen peroxide and/or consumes dioxygen) which are electrochemically measured. The measurement provides for the determination of the corresponding analyte concentration in the sample.

In another embodiment of the invention, enzyme linked immunosorbent assay (ELISA) competitive assays are performed. In these assays a capture receptor is bound to the biosensor, and the biosensor is placed in contact with a sample containing the analyte of interest that competes with a fixed quantity of analyte labeled with a substrate converter. In the alternative, a sample containing the analyte of interest on the surface of cellular material can also be used as the analytical sample. Following the formation of an (analyte and labeled-analyte)/capture receptor complex on the biosensor, the biosensor is washed to remove uncomplexed components of the solution. The biosensor is contacted with the non-electroactive substrate whereby the substrate reacts with the label to induce changes in the concentration of electroactive species. To this end, an electrode is poised at an optimum preselected potential sufficient to induce the reduction or oxidation of the electroactive species produced and/or consumed by the enzymatic reaction. Furthermore, the change in the concentration of the electroactive species is measured and correlated to the analyte which one is seeking to detect.

In preferred aspects of this invention, the assay pertains to an electrochemical sandwich immunoassay or a competitive immunoassay.

One embodiment of a sandwich assay pertains to the use of an immunosensor on which an antigen (receptor) is immobilized. A sample possibly containing mono- or polyclonal antibodies of interest (analyte) is admixed with an enzyme-labeled antigen or enzyme-labeled anti-antibody, and formed antibody/(enzyme-labeled antigen or enzyme-labeled anti-antibody) complexes in the admixture are contacted with the immunosensor to form an immobilized antigen/antibody/(enzyme-labeled antigen or enzyme-labeled anti-antibody) complex on the immunosensor. The immunosensor is then preferably washed to remove admixture components other than the immobilized complex. The immunosensor is then put in contact with the non-electroactive substrate whereby the enzyme moiety of the immobilized complex reacts with the substrate, which reaction ultimately (i.e., directly or indirectly) initiates a sequence of steps which effectuate changes in the concentration of electroactive species (i.e., produces hydrogen peroxide and/or consumes dioxygen) which are electrochemically measured. The measurement, consequently, provides for the determination of the antibody concentration in the sample.

In the aforesaid where labeled anti-antibody is used, the assay is particularly suited to allergy specific assays where the first member or capture receptor is an allergen (antigen) bound to the adhesion layer (or in other embodiments, a photoresist layer), and the second member or detection receptor is an antibody to IgE. In some cases, the IgG response to allergens may be measured similarly, i.e., by using an antibody against IgG, as the second member.

In another embodiment of a sandwich immunoassay, a mono- or polyclonal antibody (capture receptor) is immobilized on an electrode to form the immunosensor. A sample possibly containing the antigen of interest is admixed with an enzyme-labeled antibody (detection receptor), and formed antigen/enzyme-labeled antibody complexes in the admixture are contacted with the immunosensor to form immobilized antibody/antigen-/enzyme-labeled antibody complexes on the immunosensor. This immunosensor is then processed as is noted regarding the prior described sandwich immunoassay to determine the antigen concentration in the sample. The reader may refer to FIG. 14 which schematically illustrates certain aspects of a particular embodiment of the instant invention.

One embodiment of a competitive assay pertains to the contacting of an immunosensor, to which is bound an antigen to antibodies (mono- or polyclonal), with a sample possibly containing the antibodies of interest and a fixed quantity of enzyme-labeled antibodies. Following the formation of antibody and labeled-antibody/antigen complexes on the immunosensor, the immunosensor is washed to remove uncomplexed components of the solution and then the immunosensor is contacted with the non-electroactive substrate whereby the substrate reacts with the label to induce changes in the concentration of electroactive species. To this end, an electrode is poised at an optimum preselected potential sufficient to induce the reduction or oxidation of the electroactive species produced and/or consumed by the enzymatic reaction. Furthermore, the change in the concentration of the electroactive species is measured and correlated to the analyte which one is seeking to detect.

An alternative embodiment of the competitive assay pertains to the contacting of an immunosensor, to which is bound antibodies to an antigen, with a sample possible containing an antigen of interest and a fixed quantity of enzyme-labeled antigen.

In performing the electrochemical assay procedures described herein, the sample to be analyzed and the labeled ligand receptor are typically premixed before being brought into contact with the LLR-based biosensor. Such an initial premixing or incubation step is not necessary, however, because all the necessary binding interactions may be allowed to take place on the LLR sensor. Ultimately, thus, a ternary or "sandwich" complex comprised of an immobilized antibody/antigen/labeled antibody is formed. As mentioned previously, unbound materials (and interfering electroactive species) are then preferably removed from the sensor. This step may be carried out by using a wash solution which may also contain a non-ionic detergent. This wash solution is displaced, in turn, by a solution containing a substrate which is complementary to the enzyme label. Alternatively, unbound materials may be removed concurrently with the introduction of the enzyme substrate (i.e., the solution containing the enzyme substrate may also function as the wash solution). The ensuing enzymatic reaction leads to the production and/or consumption of electroactive species, which species may undergo a redox reaction at the indicator electrode. The analysis is completed by measuring the signal output (current) produced in response to the electrochemical reaction. The magnitude of the output current is proportional to the changes in the amount of electroactive species present at the indicator electrode at the steady-state and which amount is proportional, in turn, to the original concentration of the analyte of interest. Thus, in a particular embodiment of the present invention, an enzyme-linked immunosorbent assay (ELISA), or related procedures and variations known to those skilled in the art, is performed using the wholly microfabricated ligand/ligand receptor-based biosensor disclosed herein.

Table II lists a few enzyme/substrate pairs which may be utilized in the method or one equivalent to that disclosed herein for the electrochemical detection of selected immunoreactive analyte or particular ligand species. Of the enzymes listed, alkaline phosphatase, acting on a suitable phosphoric acid ester, is preferred principally because of its high turnover rate. Other enzymes may also be preferred according to the requirements of a particular system. Those workers of ordinary skill can readily determine the particular combination of characteristics (e.g., stability, specificity, etc.) best suited to a given set of conditions.

TABLE II

Representative Complementary Enzyme/Substrate Pairs which Involve the Consumption or Production of $O_2$ or $H_2O_2$[a]

| Entry | Enzyme | Substrate | Electroactive Species[b] | |
|---|---|---|---|---|
| | | | Consumed | Produced |
| 1 | uricase | uric acid | $O_2$ | $H_2O_2$ |
| 2 | sarcosine oxidase | sarcosine | $O_2$ | $H_2O_2$ |
| 3 | cholesterol oxidase | cholesterol | $O_2$ | $H_2O_2$ |
| 4 | glycerol-3-phosphate oxidase | glycerol-3-phosphate | $O_2$ | $H_2O_2$ |
| 5 | pyruvate oxidase | pyruvate | $O_2$ | $H_2O_2$ |
| 6 | diaphorase | NADH | $O_2$ | $H_2O_2$ |
| 7 | catalase | $H_2O_2$ | $H_2O_2$ | $O_2$ |
| 8 | L-glutamate oxidase | L-glutamate | $O_2$ | —[d] |
| 9 | bilirubin oxidase | bilirubin | $O_2$ | $H_2O_2$ |
| 10[c] | alkaline phosphatse | BCIP | $O_2$ | $H_2O_2$ |
| 11 | glucose oxidase | glucose | $O_2$ | $H_2O_2$ |

[a]The content of this table is by no means comprehensive with respect to the number of suitable enzyme/substrate combinations or alternative substrates (enzymes) for a given enzyme (substrate). This table serves only to illustrate useful enzymes and their substrates and is not to be construed as limiting the scope and utility of the present invention.
[b]These electroactive species are either consumed or produced or both.
[c]BCIP = Bromochloroindoxyl phosphate. Alternatively, an indoxyl ester (e.g., indoxyl acetate) may be used in conjunction with an esterase enzyme.
[d]Water is formed.

It should be stressed that the choice of immunoreactive species to be immobilized onto the base sensor depends on the particular analyte species to be measured and is within the skill of those knowledgeable in the art. For instance, a first member (capture receptor; e.g., an antibody) receptor for a particular antigen such as Immunoglobulin G, may be covalently bound to the base sensor while a second antibody, having a binding site on the antigen different from that of the first receptor, is labeled with a suitable enzyme. The sample to be analyzed for the presence of Immunoglobulin G (antigen) is then incubated with the receptor conjugate (enzyme-labeled antibody) and then brought into contact with the LLR sensor as described above. Of course, an antigenic substance may also be immobilized, instead, onto the biosensor where a particular antibody is the analyte species of interest. The sequence of steps may be varied also, and other modifications can be incorporated into the assay procedure as warranted by the particular analysis to be performed.

Perhaps in its simplest form, the assay can be performed by preparing a mixture comprising the test sample, the labeled antibody, and the substrate. This mixture is brought into contact with the LLR-based liosensor on which is immobilized a first antibody member specific to the antigen of interest. A quantitative measure of the amount of analyte species is made by comparing the signal output of the sensor with one nearby in which the immobilized antibody (first member) is absent or unreactive towards the antigen. The difference between the two signal outputs can be related to the concentration of the antigen in the test sample.

Also, whereas the foregoing application of the invention has stressed that complex formation on the immunosensor takes place after the formation of the analyte/labeled second receptor complex in a sandwich assay and with a sample containing both labeled and unlabeled analyte in a competitive assay, other variations in the assays, protocol are contemplated. It is noted, therefore, that in a sandwich assay the second member (detection receptor) can be placed in contact with the immunosensor before or after the immunosensor is contacted with the sample containing the analyte of interest. In the case of a competitive assay, the labeled-analyte can be placed in contact with the immunosensor before or after the immunosensor is contacted with the sample containing the analyte of interest.

Although the invention, as described infra pertains to examples of an assay for a specific type of analyte detected by measuring different electroactive species, it is contemplated that similar assays for a variety of analytes are possible. Possible analytes include, but are not limited to, IgG, IgM, prostatic acid phosphatase prostate specific antigen, alphafetoprotein, carcinoembryonic antigen, leutenizing hormone, choriogonadotrophin creatine kinase MB, and the like. Additionally, liquid samples containing material having analytes associated therewith, such as antigens associated with bacteria, parasites, fungi, or viruses including for example, *Neisseria gonorrhea, Gardnerelle vaginalis, Trichomonas vaginalis, Candida albicans, Chlamydia trachomatis,* hepatitis B, herpes, rubella, acquired immunodeficiency virus (HIV or HTLV III), cytomegalovirus and autoimmune antibodies can be detected using a membrane that will trap the cells or a membrane to which a receptor specific for the antigen is bound.

Other sandwich assay procedures are also contemplated using a biosensor that selectively immobilizes a first member. For example, a first member and a second member are added to a sample containing the analyte of interest. This admixture can form a first member-/analyte/second member complex that selectively binds via portions of the first member of the complex to the biosensor. Alternatively the three component admixture can be contacted with the biosensor, whereby the first member is selectively immobilized on the biosensor followed by the sequential complexing to the first member (capture receptor of the analyte) and then second member, or an analyte/second member adduct can complex with the immobilized first member. In addition, the biosensor can be sequentially contacted with the first sensor analyte containing sample and detection receptor to yield the first member/analyte/second member complex bound to the biosensors. The resulting sensor-bound complexes are then treated with a substrate as previously disclosed to assay for the analyte.

In this manner, any type of affinity binding interaction between two molecular species may be exploited so long as one of the pair may be immobilized onto the electrochemical device (preferably, via functional groups present on the outermost layer, which may be the silane layer or a proteinaceous substance) and the other may be labeled suitably. Thus, for example, the assay of the invention can also be used to detect an enzyme by binding the enzyme's receptor to the biosensor. A labeled antibody against the enzyme can be used to detect formation of a receptor/enzyme/labeled antibody complex on the biosensor. Monoclonal antibodies, may also be used in any of the assays described herein.

The assay of the invention can also be used to detect nucleic acid oligomers. In these assays the biosensor is functionalized with (has bound on it) a nucleic acid oligomer as a probe-receptor for nucleic acid material in a sample. The probe may be an oligomer of DNA, for example, complementary to a sequence in the nucleic acid of interest and can be used to bind a polynucleotide, RNA, or DNA as the analyte. Detection of the analyte-receptor complex can be done using a second nucleic acid oligomer complementary to a non-interfering region of the nucleic acid analyte of interest, the second oligomer being labeled to permit detection. Alternatively, an antibody which recognizes the hybrid formed by the polynucleotide sequence and the probe may also be used as the immobilized ligand receptor. Still other ligand receptors may be useful such as DNA-binding proteins and the like.

Moreover, receptors for certain drugs may be isolated and immobilized, and so forth. The sample may then be incubated with the LLR-based biosensor, and the amount of bound enzyme may be determined by the addition of a suitable substrate which gives rise to the production or the consumption of an electroactive species upon interaction with the enzyme. The procedures may also be varied to use a label other than an enzyme. The use of the label must allow the production of an electroactive species or the consumption of an electroactive species (i.e., gas, or some other electroactive species) which are electrochemically measured.

As a further aid to one who wishes to practice the methods or to manufacture the LLR sensors of the present invention, Table III is provided herewith as a working guide. It must be stressed, however, that appropriate combinations of analyte, immobilized receptor, and the specific method used are virtually unlimited. In addition, other types of outer surfaces or solid phases may prove useful for the immobilization of ligand receptors or immunoreactive species. It is within the skill of the ordinary practitioner to determine which systems are best suited for the particular application at hand. In the particular area of immunoassay techniques, additional methods and general discussions may be found in U.S. Pat. Nos. 4,366,241; 4,376,110; 4,486,530; and 4,740,468 the disclosures of which patents are incorporated herein by reference. Indeed, U.S. Pat. No. 4,184,849 discloses pairs of reagents for agglutination, one of which pairs may be immobilized on the present LLR-based sensor and the member of said pairs may be labeled. An inhibition of the binding of the reagent pairs, and subsequent inhibition of the activity of the label, would then be proportional to the amount of (or indicative of the presence of) analyte species in the sample.

TABLE III

REPRESENTATIVE ANALYTES WHICH MAY BE DETECTED AND/OR MEASURED USING THE LIGAND/LIGAND RECEPTOR-BASED BIOSENSORS AND SUGGESTED METHODS

| Entry | Analyte Species | Immobilized Receptor | Method |
|---|---|---|---|
| 1 | Viruses Rubella, Paramyxoviruses (Influenza Mumps, Measles, Respiratory Syncytial Virus), Cytomegalovirus, Adenovirus, Rotavirus, Retrovirus (Friend Leukemia Virus, Radiation Leukemia Virus, Human Immunodeficiency Virus), Hepatitis A, Hepatitis B, Infectious Mononucleosis, Epstein-Barr Virus, Papillomavirus | b,c | e,d |
| 2 | Mycoplasma *Mycoplasma pneumoniae* | b | e |
| 3 | Parasites Toxoplasma, Giardia, Amebiasis | b | e |
| 4 | Bacteria including Aexually-Transmitted Diseases Salmonella, Streptococci and Anti-Streptolysin O, Legionella, Staphylococci, Hemphilus, Neisseria, Chlamydia, Treponema | b | e |
| 5 | Yeasts and Fungi Candide, Histoplasma, Blasto-, mycoses, Crytococcus, | b b | e e |

TABLE III-continued

REPRESENTATIVE ANALYTES WHICH MAY BE DETECTED AND/OR MEASURED USING THE LIGAND/LIGAND RECEPTOR-BASED BIOSENSORS AND SUGGESTED METHODS

| Entry | Analyte Species | Immobilized Receptor | Method |
|---|---|---|---|
| | Coccidia | | |
| 6 | Allergy-Causing Agents IgE Total, Screens to Specific Allergens | b,c | e,d |
| 7 | Immunoglobulins and C-Reactive Protein IgG, IgM, IgA, IgD, IgE (heavy and light chains) | b | e |
| 8 | Hormones Adrenocorticotrophic hormone, Alpha-Fetoprotein, Estriol, Estradiol, Testosterone, Aldosterone, Androstenedione, Endocrine Function hormones (Cortisol, Prostaglandin, Human Growth hormone and Variants, thereof), Reproductive hormones (Human Chorionic Gonadotropin, Human Leutinizing hormone, Follicle-Stimulating hormone) | b | e,f |
| 9 | Analytes Useful in Gauging Thyroid Function T4, T Uptake, T3, Total Thyroxine, Thyroid-Stimulating hormone | b | e |
| 10 | Blood Grouping Factors, Human Leukocyte Antigen (HLA), and Platelet Factors Factor VIII, von Willebrand's, Fibrinogen/Fibrin Degradation Products, Blood Group surface antigens, HLA antigens, Platelet Factor IV, and other factors associated with clotting pathways (extrinsic and intrinsic) | b | e |
| 11 | Autoimmune Antigens and Antibodies Double-Stranded DNA, Single-Stranded DNA, Rheumatoid Factor, Smith Antigen, Smith Antigen/Ribonucleoprotein, Immune Complexes, and other associated antigens and antibodies | b,c | e,d |
| 12 | Apolipoproteins and Lipoproteins Apo A-1, Apo A-II, Apo B, Apo C-II, Apo C-III, Apo E, HDL, LDL, VLDL | b | e |
| 13 | Antibiotics Gentamicin, Tobramycin, Amakacin | b | f |
| 14 | Cardiac Glycosides Digoxin, Digitoxin | b | f |
| 15 | Antiasthmatic and Antiepileptic Drugs Theophylline, Phenytoin | b | f |
| 16 | Other Drugs (in the course of a toxicological study, drug screening, drug abuse, etc.) Procainamide, Phenobarbital, Methotrexate, salicylate, etc. | b | f |
| 17 | Tumor Markers, Cancer, and Other Miscellaneous | b | e |

TABLE III-continued

REPRESENTATIVE ANALYTES WHICH MAY BE DETECTED AND/OR MEASURED USING THE LIGAND/LIGAND RECEPTOR-BASED BIOSENSORS AND SUGGESTED METHODS

| Entry | Analyte Species | Immobilized Receptor | Method |
|---|---|---|---|
| | Antigens of Diagnostic Value Alpha 1 Acid Glycoprotein, Acid Phosphatase, Carcinoembryonic Antigen, CPK BB, Alpha 1 Antitrypsin, Alpha 2 Antiplasmin, Beta 2 Microglobulin, Ferritin (anemia), Transferrin, Ceruloplasmin | | | a The content of this table is by no means comprehensive with respect to the number, type, or scope of suitable analyte species, immobilized receptor(s), or methods which may be the subject of an analysis carried out using the ligand/ligand receptor-based biosensor of the present invention. This table serves only to illustrate the wide range of molecular species which may be measured and/or detected by a virtually unlimited number of methods and is not to be construed as limiting the scope and/or utility of the present invention.
b Antibody or receptor to given organism, immunoglobulin, antigen, component, or drug.
c Specific antigen associated with given organism.
d Indirect method in which analysis is performed for the presence of specific antibody.
e Double antibody sandwich method.
f Competitive method.

5.2.3. NOVEL ELECTROCHEMICAL DETECTION OF ENZYMATIC BREAKDOWN PRODUCTS OF BCIP AND RELATED ANALOGS OR DERIVATIVES THEREOF

In connection with the enzymatic transformations described herein, it has been discovered, that 5-bromo-4-chloro-3-indoxyl phosphate (BCIP), commonly used as a chromogenic substrate for alkaline phosphatase, functions quite efficiently as a substrate for an enzyme-mediated process which ultimately leads to the consumption of dioxygen and the production of hydrogen peroxide.

Thus, in a particular embodiment of the present invention, BCIP, or a suitable analog thereof, is used as an agent, in connection with an electrochemical assay procedure, for effectuating changes in the concentration of electroactive species. Preferably, the assay procedure and/or the devices used to perform the analyses are chosen from the methods and sensors disclosed herein. However, the present method employing BCIP, or a suitable analog thereof, is not so limited particularly because macroelectrodes, indeed, any amperometric device, may be used to perform the electrochemical measurements.

Figure 14:
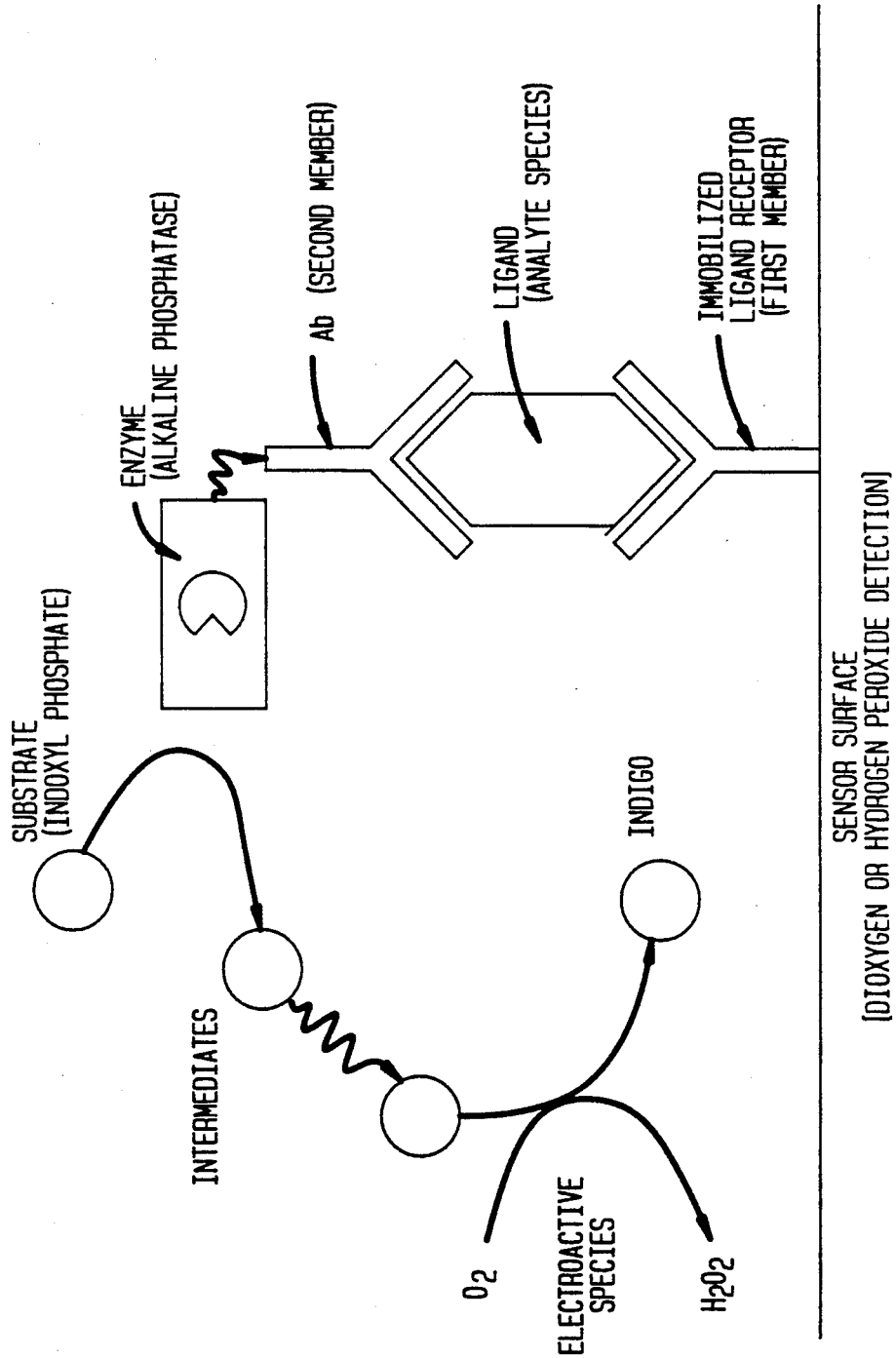

Referring now to FIG. 14, a receptor or analyte labeled with an enzyme, preferably alkaline phosphatase, converts the added indoxyl phosphate substrate (BCIP) to a hydrolyzed species that forms unstable intermediates. The subsequent auto-oxidation reaction produces indigo with the concomitant consumption of dioxygen and production of hydrogen peroxide.

The corresponding change in the concentration of $O_2$ or $H_2O_2$ can then be determined electrochemically at a preselected potential as previously discussed in Section 5.1, supra. These measurements, consequently, provide a means for correlating the activity of the enzyme label, as deduced from the electrochemical signal derived from the BCIP reagent chemistry, with the concentration of the analyte of interest.

Again, the electrochemical detection of the electroactive species may be performed using any amperometric electrochemical device, and such measurement would not be hampered by any turbidity or other condition which may interfere with existing colorimetric or spectrophotometric measurements. Preferably, the action of a phosphatase enzyme, including the acid phosphatase, on BCIP, or any suitable analog or derivative thereof (e.g., other substituted indoxyl phosphates) capable of ultimately yielding (or consuming) electroactive species, is utilized in conjunction with the microfabricated biosensors of the instant invention to provide an assay procedure with totally unexpected and unanticipated efficiency, sensitivity, and clinical applicability.

It should be apparent to those of ordinary skill, however, that, conversely, any indoxyl compound having a functional group in the 3-position which is recognized by an enzyme (that is, indoxyl reagent which may be hydrolyzed, e.g., R=phosphate, acyl), is considered equivalent and within the scope of the present electrochemical detection method (See, also, the enzyme/substrate pairs exemplified in Table II).

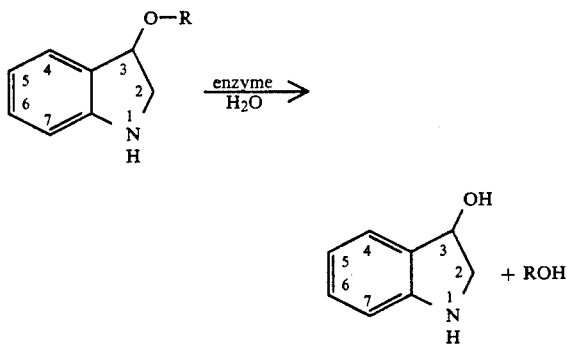

5.3. Blood Urea Nitrogen (Bun) Sensor

The potentiometric chemical sensor for urea can be viewed as a system which is constructed from functionally dissimilar components, as is the glucose sensor (supra). In one embodiment of the blood urea nitrogen (BUN) sensor, the outermost layer, the one in contact with the analyte solution, permits the transport of urea while also serving to immobilize the enzyme urease. This enzyme catalyzes the hydrolysis of urea to ammonia and carbon dioxide, as follows:

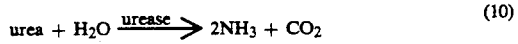

(10)

At neutral pH values, the ammonia thus produced from Eq. 10 exists predominantly as ammonium ions. By interposing a separate layered structure, which contains an ionophore with high sensitivity and selectivity for ammonium ions between the enzyme containing layer and a silver-silver chloride indicator electrode, the ammonium ion concentration at the electrode interface can be measured. In this type of measurement, the potential difference between the indicator electrode and a reference electrode is recorded.

The analytical value of the measurement is derived from the fact that the magnitude of the potential difference is related by the Nicolsky equation (Eq. 11, below) to the concentration of the analyte, in this case, urea:

$$E = E_o + \frac{RT}{nF} \log\left[ A + \sum_{a,b} k_{a,b} B \right] \quad (11)$$

where E is the measured electromotive force (signal), R is the gas law constant, T is the absolute temperature, n is the absolute value of the charge on analyte species a (e.g., n=1 for the ammonium ion), F is the Faraday constant, A is the activity of the analyte species a, B is the activity of an interfering chemical species b, $k_{a,b}$ is the interference coefficient associated with the effect of the presence of chemical species b on the electrochemical potentiometric determination of the activity of the analyte species a, and $E_o$ is a constant independent of T, A, or B. For additional discussion of the Nicolsky equation, please refer to Amman, D. *Ion-Selective Microelectrodes*, Springer, Berlin (1986) p. 68 and references cited therein.

5 3.1. BUN BASE SENSOR

In a preferred embodiment of the present invention, the unit cell for the BUN sensor comprises a thin film silver-silver chloride indicator electrode operating in combination with a thin-film silver-silver chloride reference electrode.

Figure 3:
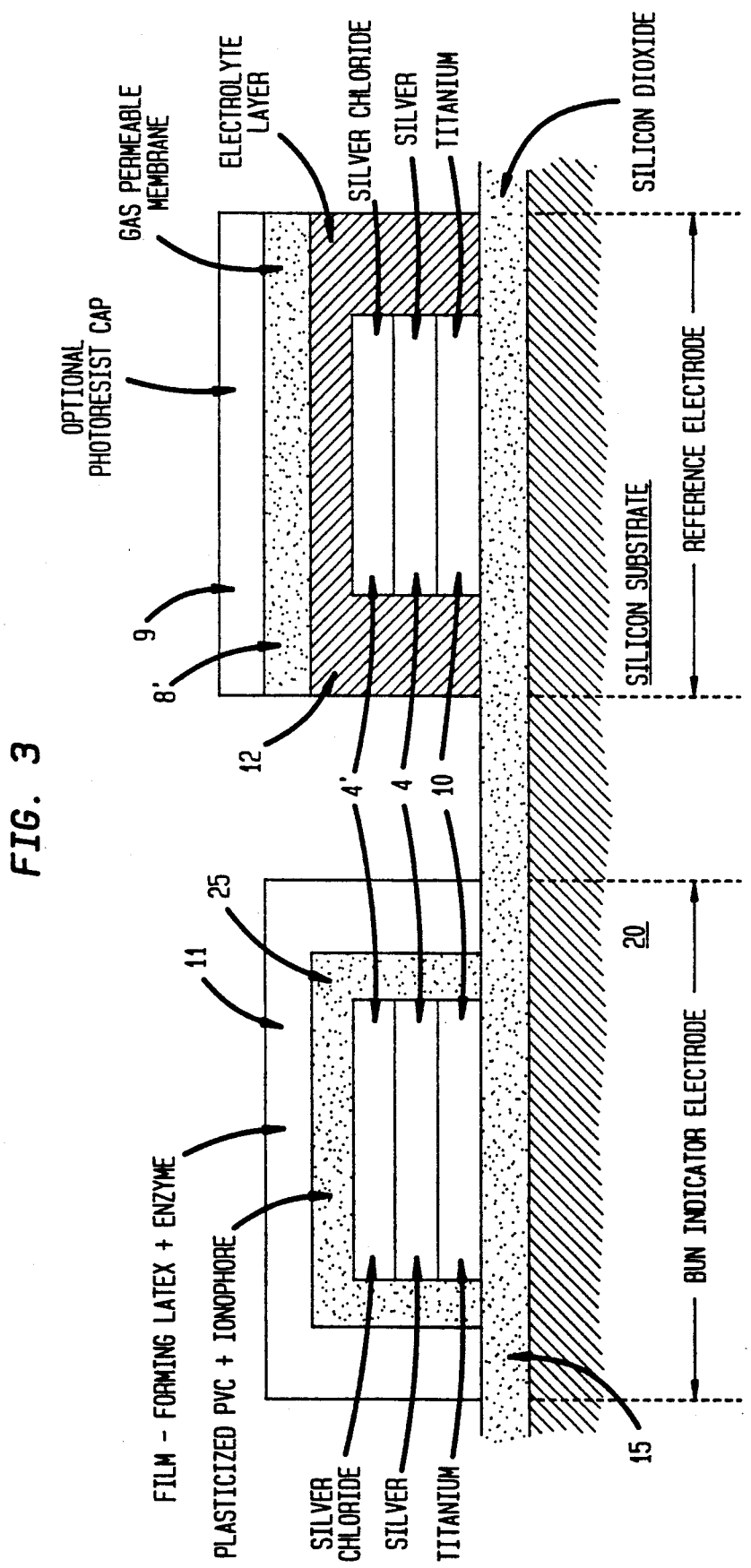

Referring now to FIG. 3, the substrate wafer, 20, is silicon, with an overlaid insulating layer of silicon dioxide, 15. The first metal layer, 10, is titanium and serves the same function in the BUN sensor as in the glucose sensor. Succeeding layers 4 and 4', are the silver and silver chloride layers. On the left side of FIG. 3, the remaining layers of the indicator electrode include (i) a semipermeable membrane film, 25, comprising an organic polymer layer (e.g., poly(vinyl chloride)—PVC) and an ammonium ion ionophore; and (ii) the outermost biolayer, 11, comprising in this particular sensor, a film-forming latex (e.g., poly(vinyl acetate-co-vinyl alcohol)) and a sufficient amount of the enzyme urease.

The reference electrode portion of the unit cell may be comprised of overlaid structures as shown in FIG. 3. In this particular embodiment, the metal and chloridized layers of the reference electrode are covered by an electrolyte layer, 12, which may comprise any material which is able to hold a high concentration of salt but which is, preferably, photoformable. In this respect, a fish gelatin formulation is the preferred material and may first be photopatterned and subsequently saturated with a salt, such as potassium chloride. A separate gas permeable membrane, 8', may also be present which serves to diminish the loss of electrolyte or salt to the bulk analytical sample but allows the rapid wet-up (i.e., passage of $H_2O$ or other small gaseous molecules) of the reference electrode prior to commencing the sample analysis. The photoresist cap, 9 which may be a remnant of the patterning process need not be removed if it does not bar the free passage of solvent, solute, or ions. In a preferred embodiment, the reference electrode structure described in co-pending U.S. application Ser. No. 07/156,262, filed Feb. 16, 1988, the disclosures of which are incorporated herein by reference, is used. Alternatively, a reference electrode structure in which the distance between the liquid junction and the surface of the silver/silver chloride is sufficiently large, such that the concentration of electrolyte in the immediate vicinity of the Ag/AgCl structure is substantially constant for a period of time sufficient to perform a measurement of the potential difference between the indicator electrode and the reference electrode.

As illustrated in FIG. 3, superimposed over the indicator electrode of a BUN sensor is a thick film ammonium ion-sensitive structure comprising a poly(vinyl chloride) (PVC) binder, tris(2-ethylhexyl)phosphate as a plasticizer, and nonactin as the ionophore. The indicator electrode can be made selective for different ions by using the same binder and plasticizer composition but with different ionophores. For example, valinomycin, monensin and (methyl)monensin, or tridodecylammonium chloride have been used to make potassium, sodium, or chloride-ion selective electrodes, respectively. Other ionophores may include, but are not limited to crown ethers, trialkylamines, or phosphate esters, and the like. Alternatively, other polymeric binder materials may be used besides PVC. These polymers may include, for example, silicon rubber, polytetrafluoroethylene plastics, or derivatives of PVC containing ionizable functional groups (e.g., carboxylates). Other plasticizers suitable for use in the present invention may include, but are not limited to tris(2-ethylhexyl)phosphate, nitrocymene, 2-nitrophenyloctyl ether, dibutyl sebacate, diethyl adipate, phthalates, propylene carbonate, 5-phenylpentanol, or mixtures thereof. Still other binders and ionophore combinations may occur to those skilled in the art which are within the scope of the present invention. The resulting semipermeable ion-selective film may have a thickness in the range of about 2 $\mu$m to about 200 $\mu$m, preferably about 10 to about 30 $\mu$m.

Figure 4:
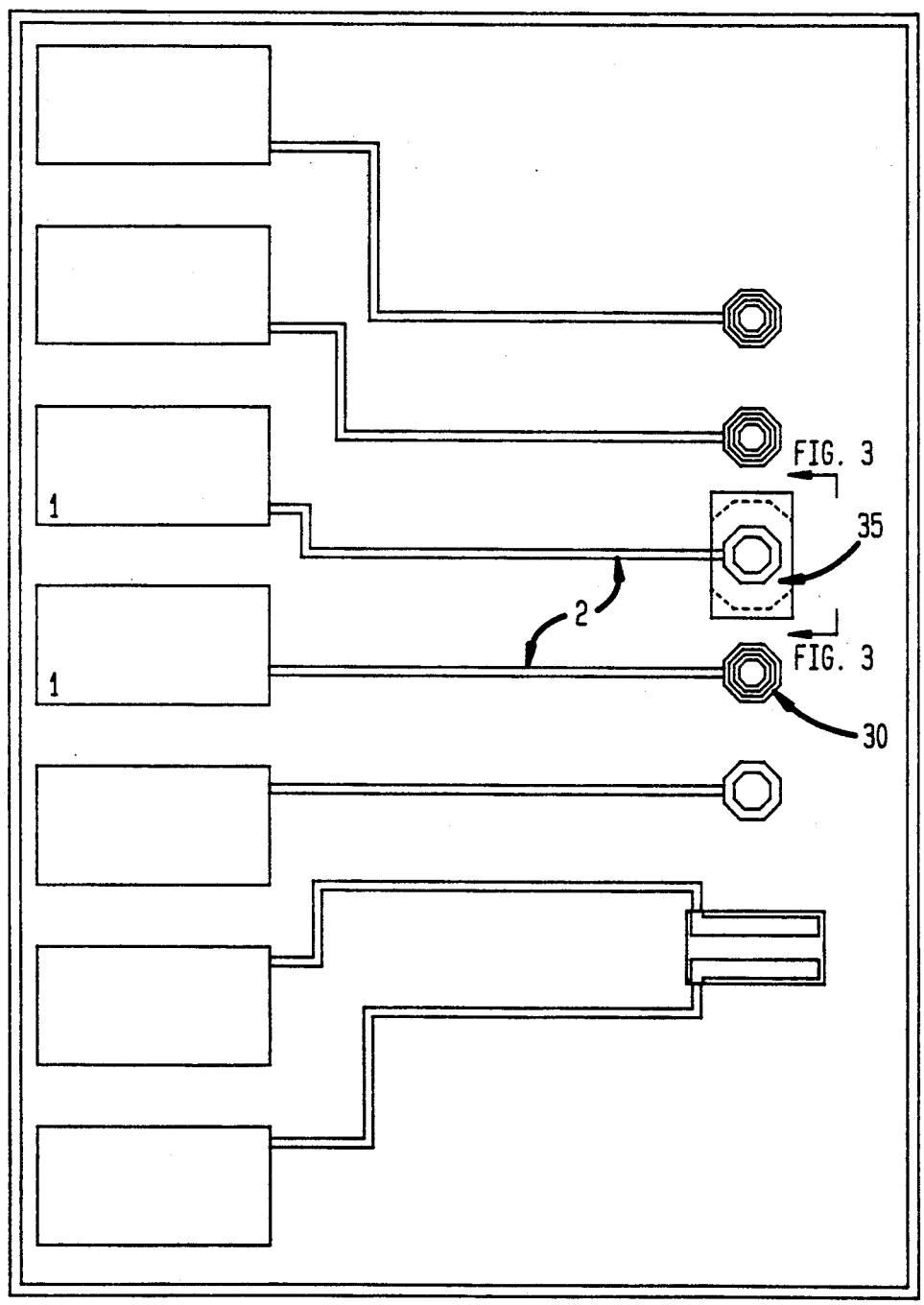

Referring now to FIG. 4, indicator electrode, 30, and the adjacent reference electrode, 35, are each connected by an overpassivated signal line, 2, to a contact pad, 1. The unit cell is confined within a rectangular area, which is repeated in a square array several hundred times on a single silicon wafer. In particular embodiments of the instant invention, other indicator electrodes may be present in the biosensor for the simultaneous measurement of ionic species (e.g., $Na^+$, $K^+$, or $Cl^-$) in addition to ammonium ion.

5.3.2. BUN BIOLAYER

At this point, it is important to distinguish between the properties of particle latices and their film-forming counterparts. A particle latex comprises a solid polymeric structure, such as polystyrene, which is coated with a hydrophilic material that allows the polymer particle to be waterborn. Particle latex materials have been used traditionally to immobilize all manner of biologically active materials (See, Kraemer, D. et al., U.S. Pat. No. 4,710,825). However, an important property of *particle* latices which is unsuitable in the present application is that even after these materials have been dried, the particles can be redispersed easily in water. By contrast, a film-forming latex is a colloidal solution comprised of a mobile polymeric liquid core, such as a vinyl acetate, with a hydrophilic outer coating. Such a film-forming latex is made by an emulsion-polymerization process in which a water-immiscible organic monomer or a mixture of monomers is added to an aqueous medium containing a free radical catalyst. The polymerization may be initiated, for example, by mechanical agitation (See, for example, Vanderhoff, J.W., *J. Poly. Sci. Polymer Symposium* 1985, 72, 161–198). When this material is dried the particles coalesce to form a film which *cannot be redispersed in water*. Because film-forming latices are water-based and contain both hydrophilic and hydrophobic components, one may speculate that these compositions are able to provide a stabilizing environment for biologically active species and constitute an effective medium for the immobilization or incorporation of same.

It has further been found that film-forming latices from both natural and synthetic sources are of significant utility. For example, the following synthetic monomers, their chemically-modified analogues, copolymers, or mixtures thereof may be used to make a film-forming latex: vinyl acetate, ethylene, acrylate or acrylic acid, styrene, or butadiene. These and many other materials known to those skilled in the art are available commercially from many sources including Reichhold, Air Products, DuPont, Dow Chemical, or Imperial Chemical Company. Natural isoprene-based polymers are also useful and available from Imperial Adhesives and Chemicals, Inc. and from General Latex and Chemical Corp.

Moreover, it has been discovered that these materials retain their film-forming properties even when non-latex water-soluble components (e.g., proteins, enzymes, polysaccharides such as agarose, or synthetic polymers such as poly(vinyl alcohol), poly(vinyl pyrrolidone), and the like) comprise up to about 25% by weight of the solids content. In this respect, a significant consideration related to a microfabrication process for the production of biosensors is that the established film adheres effectively to a planar substrate even in the presence of large amounts of additives (i.e., enzymes).

Various methods can be used to define a layer on a planar substrate. If a thick layer (about 5 to about 200 $\mu$m) is required, microdispensing of a viscous film-forming latex composition (<500 Centipoise as measured on a Brookefield RV viscometer) is preferred. However, if a thin layer (about 0.2 to less than about 5 $\mu$m) is required, a composition with a lower viscosity is used which can be microdispensed directly onto the indicator electrode, or alternatively, either microdispensed or spin-coated onto a positive resist layer (e.g., Shipley AZ®1370 SF) which has been patterned to leave the area over the indicator electrode exposed. Any suitable solvent known in the art, such as n-butylacetate and the like, is then used to lift off the resist, along with the excess latex. A separate technique using a photoresist cap may also be used. Specific examples of the "lift-off" and resist cap techniques are given in the Examples Section, infra.

As in Section 5.1.3 above, control of the surface energy may be used beneficially to control the spreading of the microdispensed reagent (and, thus, its dimenionality, such as thickness). A fluorocarbon (e.g., $cF_4$) plasma treatment of a polyimide layer surrounding the indicator electrode causes the aqueous based latex to exhibit a high contact angle (i.e., minimizes spreading and maximizing thickness).

To immobilize one or more biologically active species in a latex layer it is possible either to mix the species with the latex prior to deposition or impregnate the layer after deposition. The stability of the biologically active species, particularly enzymes, is enhanced by adding a crosslinking agent either before or after deposition. These crosslinking agents are well-known in the art and may include such compounds as glyoxal, glutaraldehyde, melamine formaldehyde, urea formaldehyde, and phenol formaldehyde. Other suitable crosslinking agents may possess at least two functional groups which may include vinyl, carboxyl, anhydride, amine, amide, epoxy, hydroxyl, cyano, isocyanato, thio, halo, in addition to formyl, and stable combinations of these functional groups (e.g., a chloroalkylepoxide). These additives can significantly enhance the wet-strength of the biolayer and extend the shelf-life of the completed biosensor. In almost all instances, one or more of the biologically active macromolecules listed in the preceding or following sections of this disclosure may be successfully immobilized using a film-forming latex such as Elvace or Elmer's Glue. In some cases, a more responsive sensor may result when using a film-forming latex compared with the photoformable proteinaceous matrix used in the glucose sensor.

In a particular embodiment of the present invention, a film-forming latex is used to immobilize the enzyme urease. A higher enzymatic activity is achieved in this case compared to a urea sensor in which the biolayer is manufactured from a photoformable fish gelatin.

Furthermore, the porosity of the biolayer can be controlled to a significant extent by incorporating certain additives, such as salts (e.g., sodium chloride) or sugar alcohols (e.g., mannitol, erythritol, or sorbitol), into the latex mixture prior to deposition. For example, the addition of sorbitol to the latex formation (1 g/dL of solution) significantly decreases the time needed for wet-up of the dessicated urea sensor. A shorter wet-up period provides, in turn, for a faster response.

5.3.3. PERFORMANCE OF THE BUN SENSOR

Figure 9:
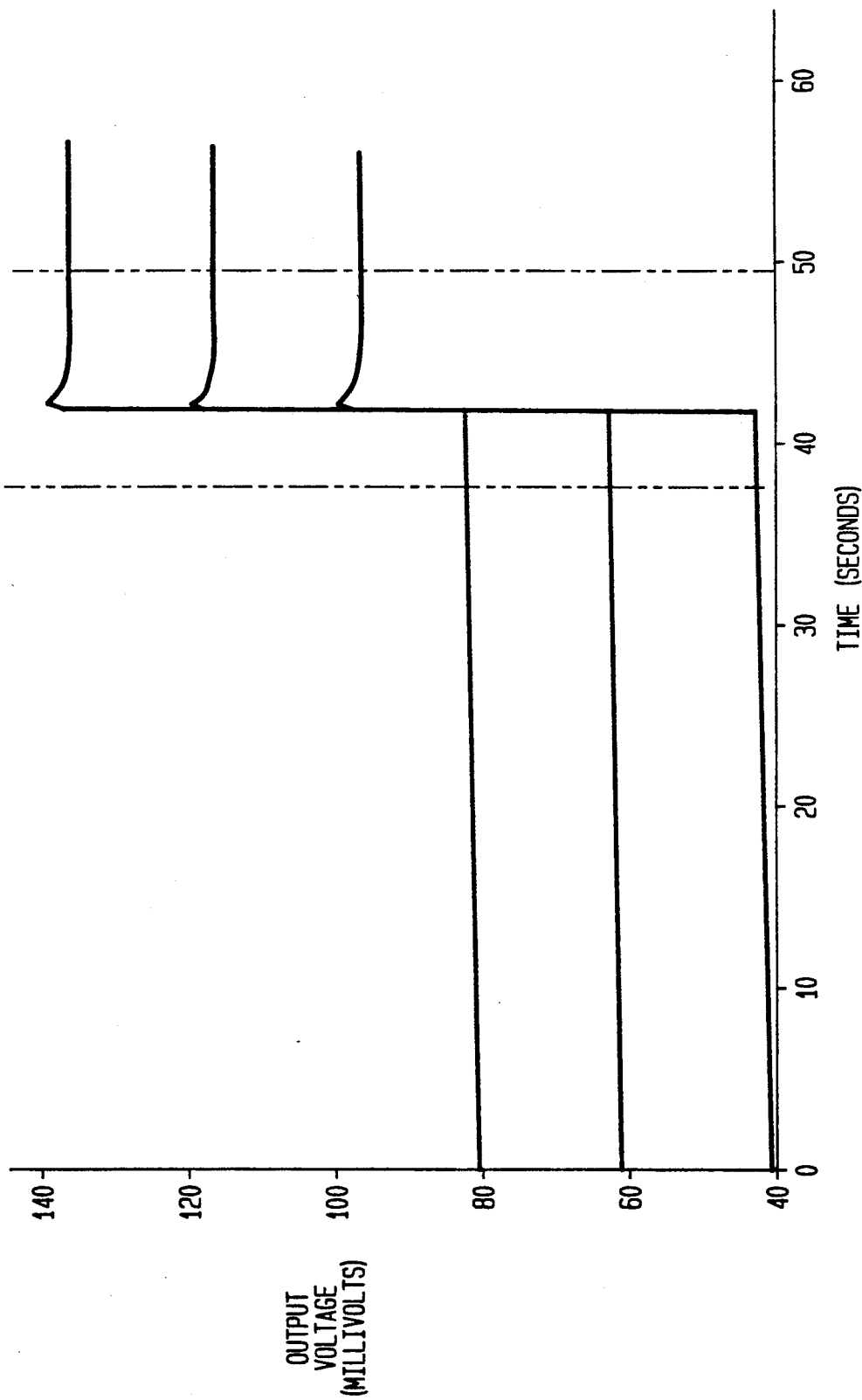

FIG. 9 shows the response of the ammonium ion sensor as a function of time measured against the on-chip reference electrode. The measurements are done on a sensor starting in the dry state. The initial slow increase is due to wetting of the sensor by the solution. At the moment that the unknown solution is injected the sensor responds very quickly so that measurements can be done within a few seconds. The test solution changes concentration from 2 to 20 mM ammonium. The three graphs on the figure are from different urea sensors and show the uniformity of the response.

Figure 10:
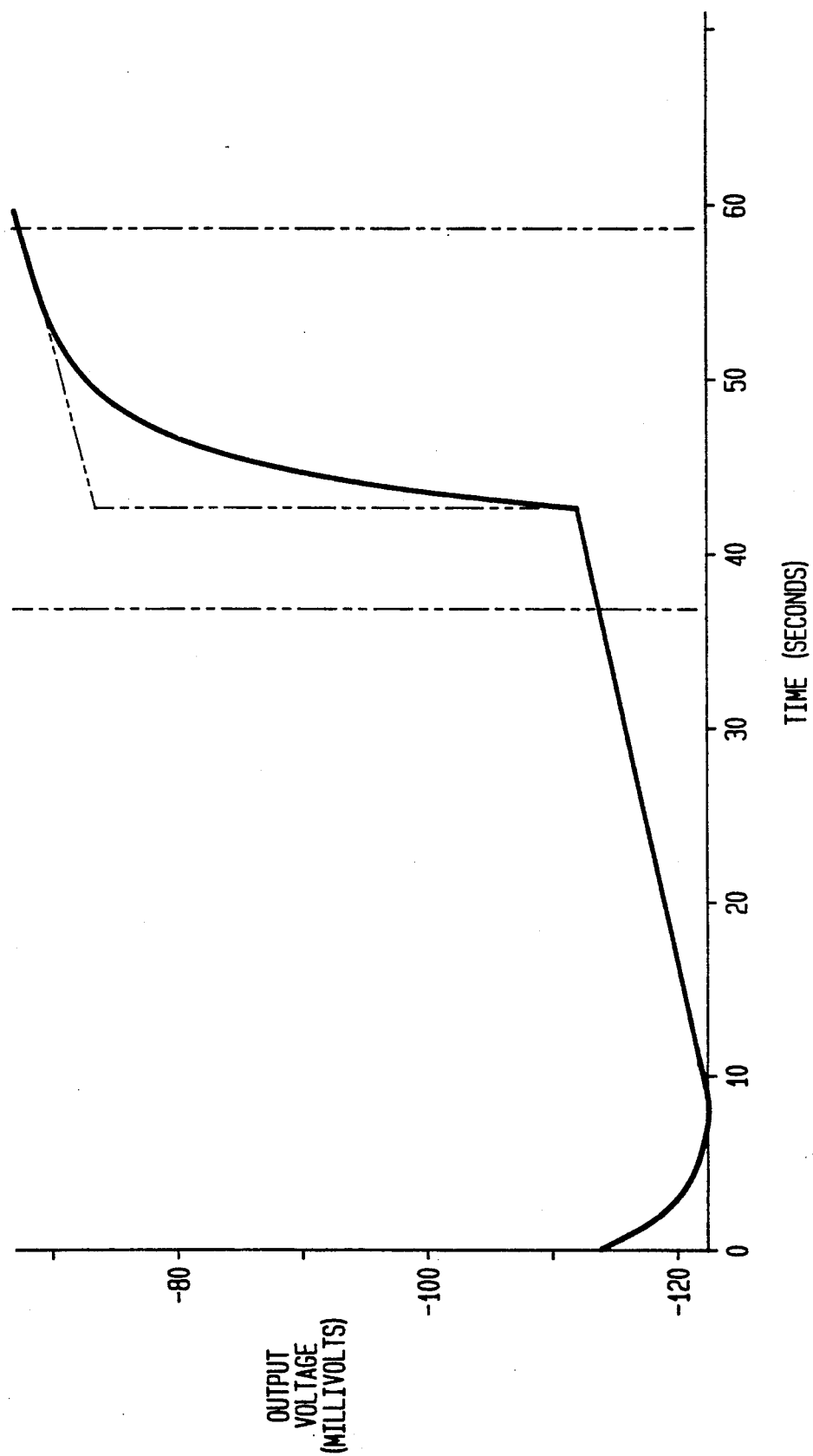
Figure 11:
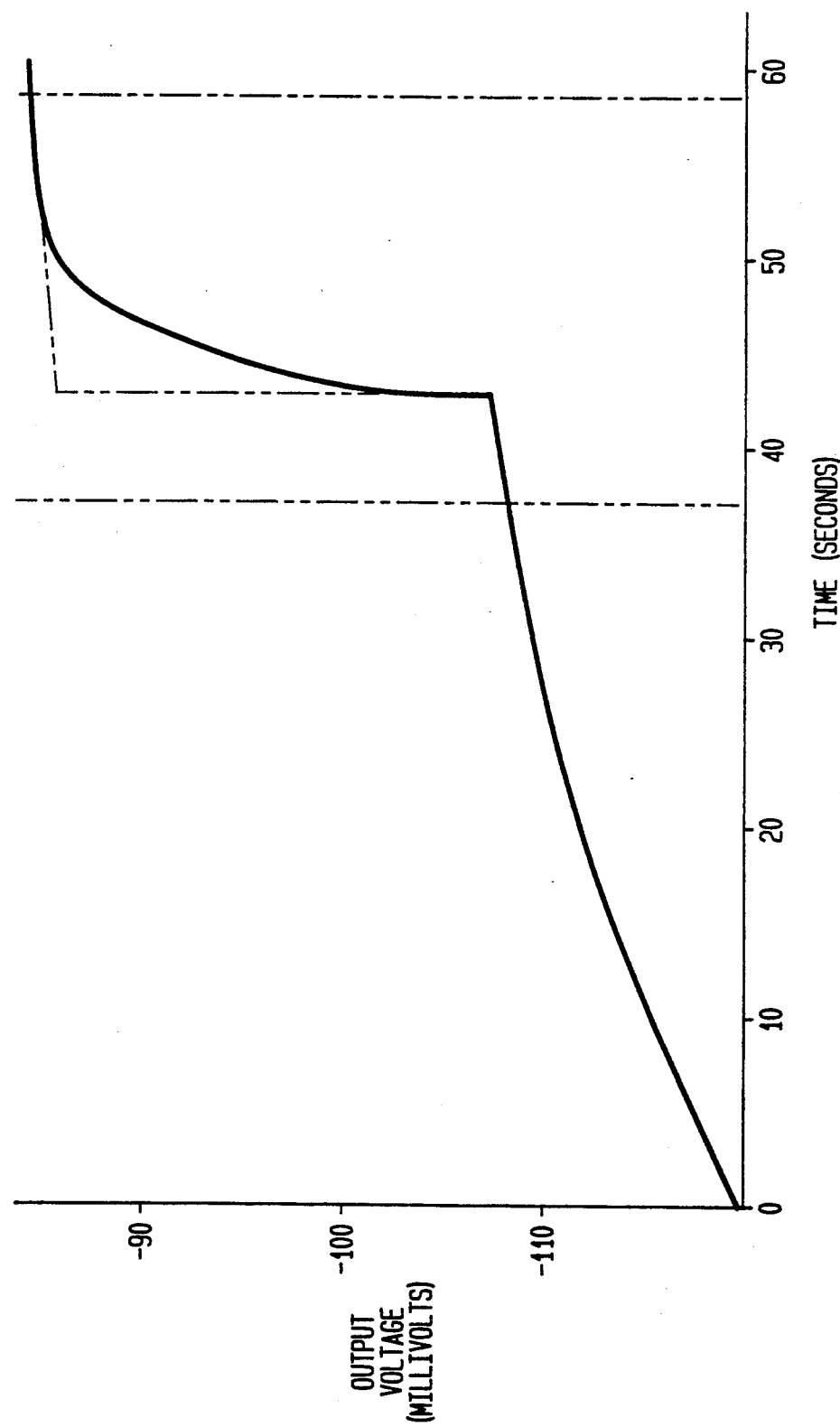

The response of the BUN sensor to aqueous urea solutions is given in FIG. 10. The initial decrease and subsequent increase is due to the wetting of the sensor. After about 40 seconds the concentration is changed from 1 to 10 mM urea. The slower response, in comparison to the sensor of FIG. 3, is due to the outer film-forming latex layer through which mass transport is necessary and where also the catalytic reaction occurs before the ions can reach the underying indicator electrode. The Nicolsky selectivity coefficient are taken into account in determining the urea concentration. FIG. 11 shows the response of a BUN sensor to whole blood which has been spiked with urea to elevate the level. The response is similar to the previous one. The BUN sensor has a linear range between 1 and 20 mM urea and a measurable range up to 40 mM in blood.

5.4. Automated Microdispensing System

An important aspect of the microfabricating process described in the present invention is ar automated system which is able to microdispense precise and programmable amounts of the materials used in the biosensors of interest. The microdispensing system, which is based on a wafer prober (Pacific Western Systems, SP1-C), is comprised of a vacuum chuck and a syringe, each of which are attached to separate means for altering the vertical, horizontal, lateral, or rotational displacement of these key elements of the system. For the sake of economy, it is sufficient to have means for changing the vertical displacement of the syringe so long as one can change the position of the vacuum chuck multidirectionally. The movements of both elements may be controlled via a single personal computer using customized software (Turbo-C) to drive the machinery. The position of the vacuum chuck may be reproducible within $\pm 13$ microns or better in either x or y directions.

The drop sizes which can be dispersed reproducibly extends over a wide range. For volume sizes between about 5 to about 500 nanoliters (nL), the drops can be applied with a precision of about 5%. A solenoid having a 0.1% precision rating is sufficient for this purpose. The height of the tip of the syringe needle above the biosensor should be between about 0.1 to about 1 mm, depending on the volume to be dispensed: generally, the smaller the volume of the drop, the lower the elevation of the needle from the sensor (Please refer to Section 5.4.1.1, below).

The precise alignment of the syringe needle with the preselected area of the biosensor can be achieved optically, if necessary, by means of a camera and a reticle. Such an operation can be performed manually by an operator or automatically by means of a visual recognition system incorporating aspects of artificial intelligence. Of course, the rate at which material can be dispensed onto the devices is limited by the speed with which the elements of the system can arrive at their specified positions. However, multiple syringe configurations may be operated advantageously as described further below.

Figure 12:
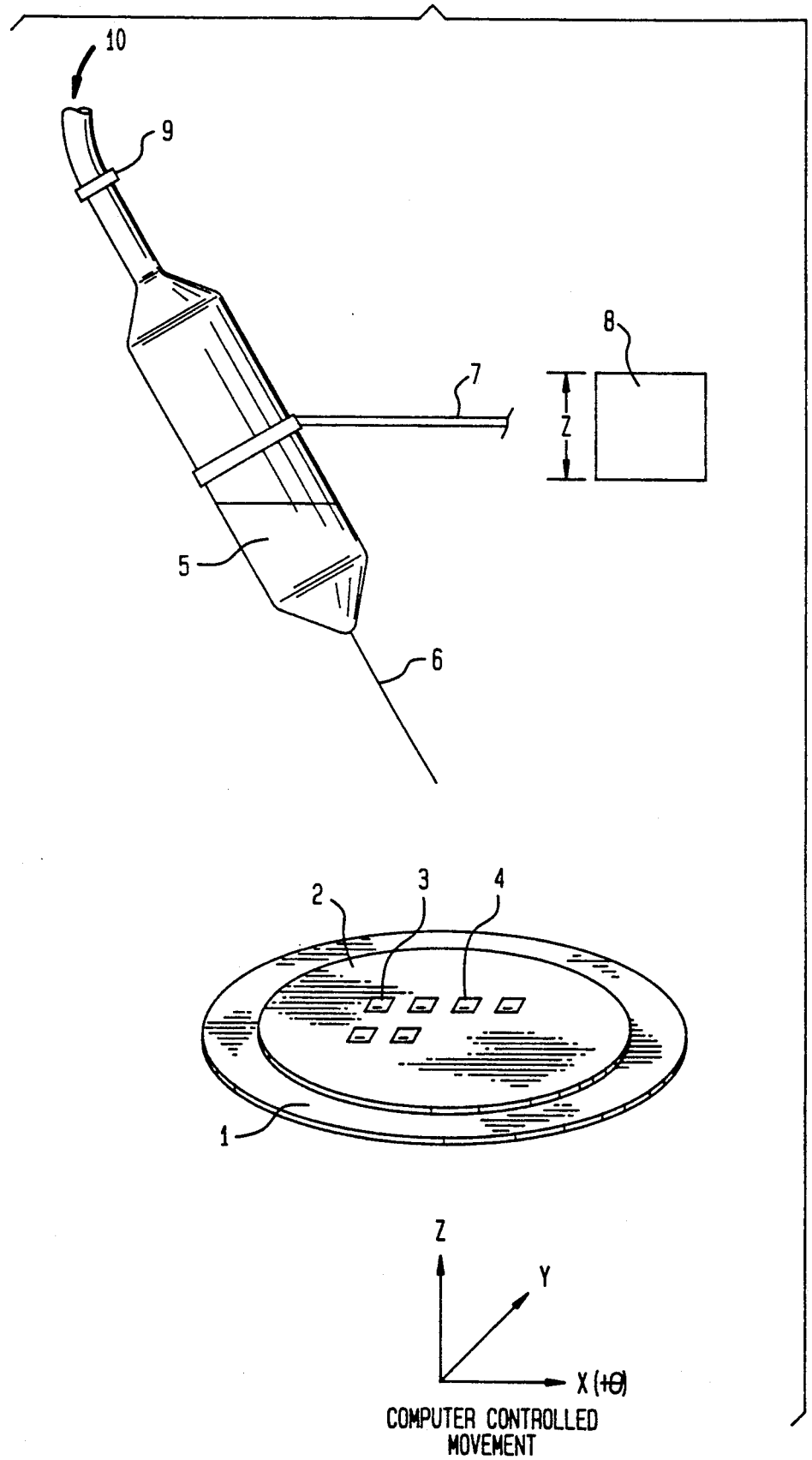

Referring now to FIG. 12, a suitable microdispensing system will have the elements of a vacuum chuck, 1, on which the wafer, 2, is held and the syringe, 5, holding the material to be microdispensed. The liquid material is applied through a needle, 6, with the aid of pressurized nitrogen or other suitable gas supplied at 10. The flow of the pressurized gas is controlled by a solenoid valve, 9, which provides precise pulses of gas to dispense predetermined volumes of material. The support arm, 7, may be connected to a means 8 for adjusting the vertical position, Z, of the syringe and needle. The film-forming latex materials containing the appropriate bioactive molecule may be dispensed on the biosensor chip, 3, at a preselected region, 4. As discussed above, the vacuum chuck is also coupled to a means for varying the displacement of the wafer multidirectionally. It is understood, of course, that the means, 8, may also be varied multidirectionally, if desired.

Figure 13:
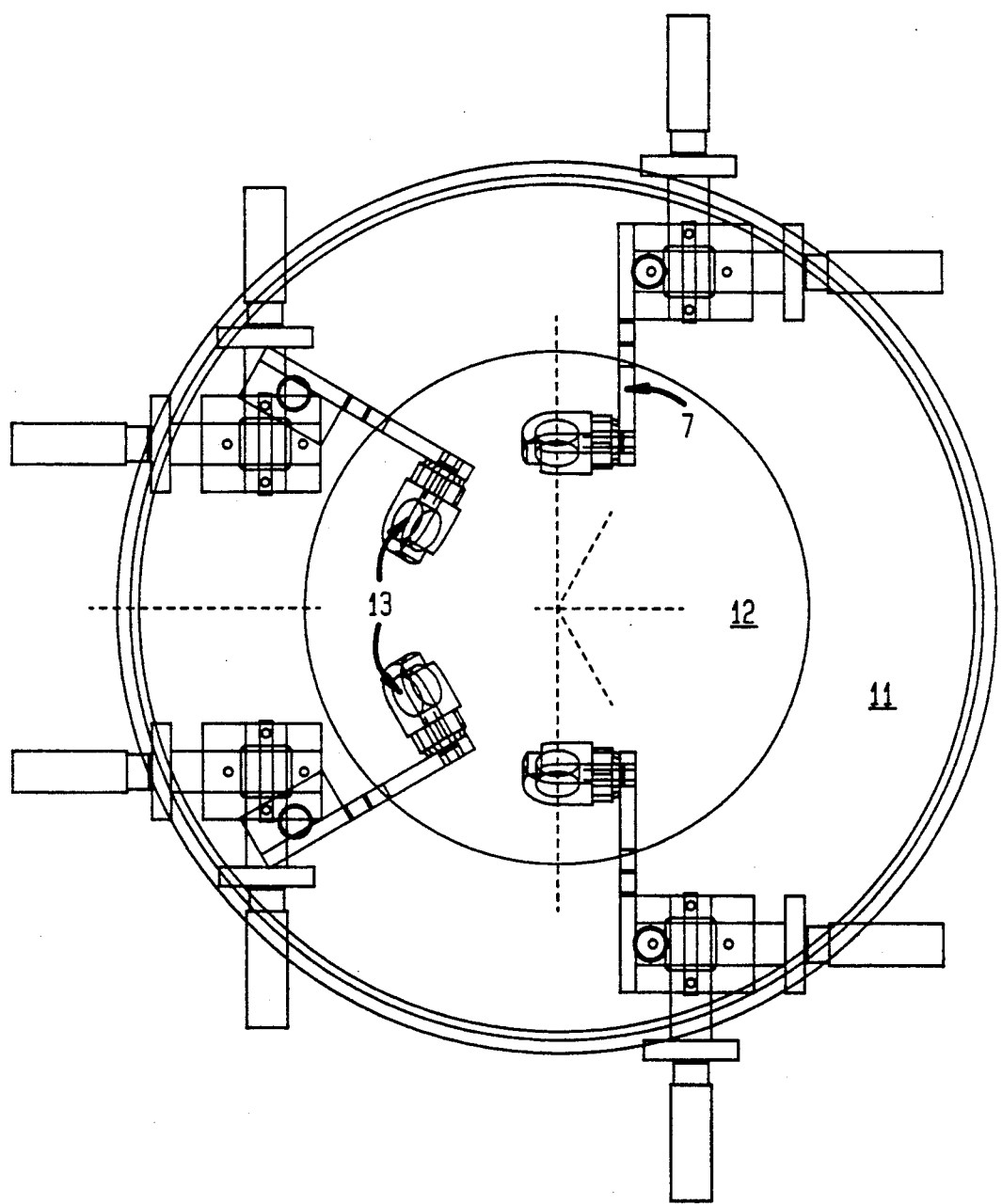

An alternative embodiment of the instant microdispensing device is illustrated in FIG. 13, which comprises a plurality of independently controllable microdispensing syringe assemblies. These assemblies are preferably mounted on a circular support, 11, having an opening, 12, below which opening the wafer and vacuum chuck may be positioned appropriately.

Using such a multiple assembly configuration, more than one component layer may be established on the biosensor at any given time. Of course, the alignment considerations are more complex in this multiple assembly configuration, the individual needles needing to be positioned over particular areas of the chip. However, this configuration allows the most flexibility with respect to where the fluids may be dispensed while accomplishing the uniform microfabrication processes which are part of the primary objectives of the present invention.

5.4.1. FURTHER COMPOSITIONS AND METHODS USEFUL FOR MICRODISPENSING LO-

CALIZED DISCRETE FILM LAYERS OF CONTROLLABLE BUT UNIFORM DIMENSIONS

As mentioned briefly in Section 5.1.3, the dimension of a microdispensed layer (especially its thickness) are governed by a variety of factors. More specifically, the inventors have found that these factors involve, among other things, the volume of and the manner in which a fluid is dispensed, the composition and surface tension of the fluid, and the free energy characteristics of the surface onto which the fluid is dispensed. The following sections seek to explore more fully the intricate interplay between these multiple factors and how their individual and collective effects can be harnessed to provide a more reproducible but versatile manufacturing process.

5.4.1.1. VOLUMETRIC MICRODISPENSING OF FLUIDS

It is useful, at this point, to consider the dynamics involved when a single drop of fluid is formed at and expelled from a needle needle.

As more fluid is expelled from the needle tip, the drop will grow in size until the gravitational force acting on the mass of the drop exceeds the opposing forces maintaining contact with the needle tip. These opposing forces include the adhesive forces between the needle tip and the fluid or liquid, and surface tension of the liquid itself. It is well established that at low liquid flow rates where discrete drop formation is complete, the drop volume is fixed. However, the volume may be changed by varying any of the fluid related parameters discussed above, or by changing the diameter of the needle tip thus changing the available surface area for fluid adhesion. The present inventors have also demonstrated that the exterior surface of the needle may be coated with an additional layer of a material that modifies the fluid adhesion. For example, a hydrophopic polytetrafluoroethylene (PTFE) coating applied to the needle tip reduces the natural drop size of an aqueous based latex material by reducing the adhesive forces between the drop and the needle tip. Conversely, the needle tip can be coated with a hydrophilic material (e.g., crosslinked poly(vinyl alcohol) (PVA) to enlarge the volume of the emerging drop before gravity pulls it away from the needle tip. Doubtless, other variations can be readily conceived by those of ordinary skill, which variations are considered part of this invention.

In circumstances where a controlled volume must be microdispensed onto a surface, it has also been discovered that it is possible to have the microsyringe tip positioned above the planar surface at a height which does not allow the drop to form completely (and then fall to the surface under the influence of gravity), but the partially formed drop actually contacts the surface and the new adhesive forces between the liquid and the surface begin to spread the drop. If the needle tip is now retracted in the Z-direction a sufficient distance away from the surface, then the cohesive forces of the liquid is overcome and a volume of liquid less than the fixed drop size would remain in contact with the surface. This technique can be used to dispense reproducibly any volume of liquid from about one-one thousandth of the fixed drop size or greater. For example, the present inventors have shown that an 8 nL drop of glycerol could be dispensed reproducibly where the natural drop size would have been 8 μL.

5.4.1.2. FLUID COMPOSITIONS WITH PREDETERMINED SURFACE TENSION

It is well known that the surface tension, $\alpha$, between a pure liquid and its vapor phase can be changed by adding reagents. For example, if a fatty acid is added to water the hydrophilic portion of the molecule is cohesive, whereas the hydrophobic portion is not, i.e., it resides in a high energy solvated state. Minimal work is required to bring the solvated portion of the molecule to the surface, and thus, the surface layer becomes enriched in the non-cohesive portion of the fatty acid, reducing the surface tension.

Conversely, solutes such as ionic salts added to aqueous systems increase cohesion (ion-dipole interactions) between water molecules in the bulk of the fluid, increasing the work required to introduce them to the surface. The surface tension of the fluid is thus increased.

In the context of the present invention, a brief discussion of the concept of a contact angle is appropriate. It is known that when a small amount of liquid is placed on a planar solid surface, the liquid does not wet the surface completely (continue to spread indefinitely) but remains as a localized drop having a defined contact angle, $\theta$, $$\cos \theta = (\alpha_{SV} - \alpha_{SL})/\alpha_{LV}$$

where $\alpha_{SV}$ is the surface tension between the surface and the vapor, $\alpha_{SL}$ is the surface tension between the surface and the liquid, and $\alpha_{LV}$ involves the liquid/vapor surface tension. The geometry of the drop and its associated contact angle reflect a balance between the cohesive forces between molecules in the liquid and adhesive forces between the liquid and the surface. Where cohesive forces dominate, the contact angle is high and when adhesive forces dominate the contact angle is low (See, for example, FIG. 15). Clearly, a hydrophilic liquid will have a low contact angle on a hydrophilic surface, whereas a hydrophotic liquid will have a high contact angle. If the contact angle, $\theta$ is greater than 90° the surface is said to be nonwetting. Simple optical instrumentation is available for measuring contact angles.

The microdispensable fluid compositions of the present invention are prepared to have a controlled optimized surface tension. Suitable additives are used when necessary. The hydrophobicity or hydrophilicity of the fluid is controlled in the same manner. Where a cured membrane is required as the end product, the solids content and volatile solvents content are carefully adjusted. Moreover, the ratio of these components is also used to control the viscosity.

The preferred microdispensable compositions for application onto a given surface are described further in the Example Section. In particular, examples for formulations are provided for establishing layers which are sensitive to Cl−, Na+, K+, pH, NH4+, and Ca++ ions. These compositions comprise PVC polymer, plasticizers, ionophores and solvents with viscosities generally higher than those used for planar casting (e.g., spin-coating) of membranes. It has been found that these higher viscosity compositions cure or dry without deformation of the membrane layer. Related problems, e.g., that of ensuring the homogeneity of the matrix at high viscosity and thus preventing phase separation of materials after time (i.e., considerations related to shelf-life) are also alleviated by these novel compositions. Other additives are also used to prevent long term degradation of the membranes. Finally, the solvent system is selected to provide the appropriate surface tension and stability. For $K^+$, $Na^+$, $NH_4^+$, pH and $Ca^{++}$ sensors, the solids content (wt %) of plasticizer, PVC polymer, and ionophore are preferably 60-80%, 15-40% and 0.5-3%, respectively. For the $Cl^-$ sensor, ratios of 25-40% plasticizer, 25-45% PVC, and 25-35% ionophore are preferred.

5.4.1.3. METHODS FOR TAILORING THE SURFACE ENERGY OF A PLANAR STRUCTURE

In addition to the factors described above relating to controlled volumetric dispensing of fluids having an optimized surface tension associated with a prescribed composition, the present inventors have discovered that tailoring the surface free energy of the substrate, or surface onto which the fluid is dispensed, provides an unexpected degree of control over the final dimensions, especially the thickness, of the resulting layer. Even more surprising, it has been discovered that a process which combines these techniques gives predictable and reproducible results. Furthermore, the resulting process is highly versatile, allowing the deposition of arrays of biolayers of varied composition and utility.

As an example, consider a sensor consisting of a silver/silver chloride electrode with a polyimide layer extending away from the electrode perimeter. If a control fluid, e.g., a mixture of 80% glycerol and 20% water, is dispensed onto the surface, a contact angle of 50° is attained. Pretreating the surface with a tetrafluoromethane plasma renders the polyimide surface more hydrophobic. If the same control fluid is now dispensed over the $CF_4$-treated surface, contact angles of 50° to 120° are attained.

Alternatively, if the polyimide surface is first treated with an oxygen plasma, the surface is made more hydrophilic and contact angles of 10° to 50° are attained with the same control fluid.

Figure 15A:
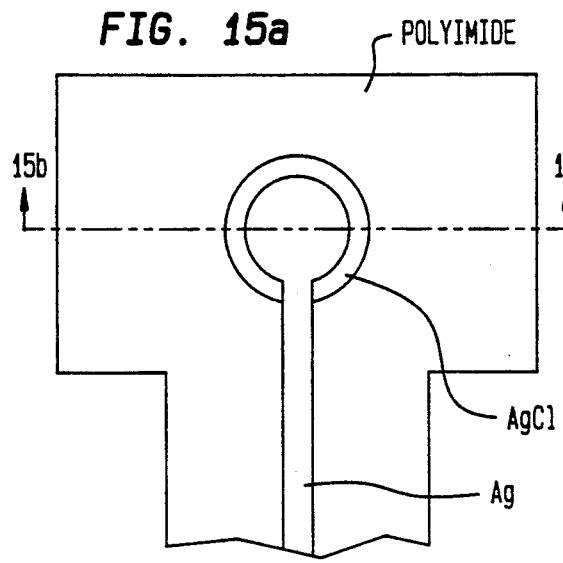
FIGS. 15a–15e illustrate the effect of pretreating the electrode surface to alter its surface free energy characteristics. The contact angle, $\theta$, of a microdispensed fluid, and eventually, the thickness of the membrane layer above the electrode, is thus controlled.
Figure 15B:
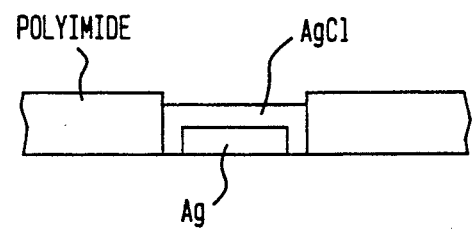
Figure 15C:
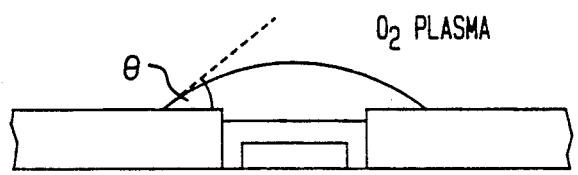
Figure 15D:
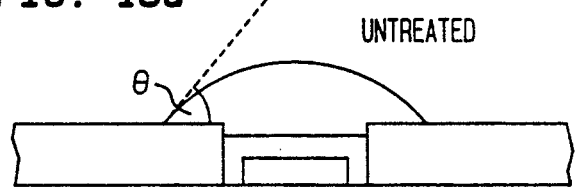
Figure 15E:
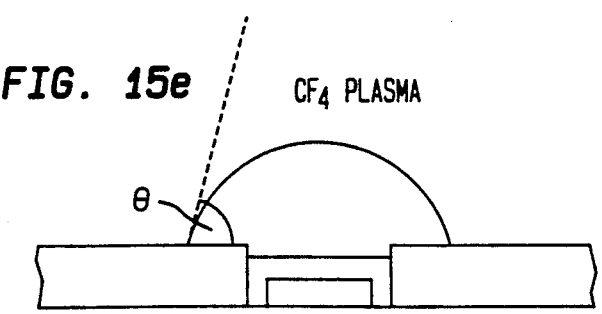

Referring now to the figures, FIG. 15a is a representation of the perimeter of a silver/silver chloride electrode circumscribed by a polyimide layer. FIG. 15b is the corresponding elevational view of the electrode. As depicted in FIGS. 15c, 15d, and 15e, the contact angle $\theta$, is small for a microdispensed hydrophilic fluid resting on a polyimide surface which had been exposed to an $O_2$ plasma. The contact angle is larger if the surface is untreated and increases further if the surface is first treated with a $CF_4$ plasma. Thus, the configuration of the dispensed fluid over a given surface is manageable to a large extent by a careful choice of the conditions to which the given surface is (or is not) subjected.

During plasma treatment two net processes may occur: either the surface is etched, e.g., surface material reacts with the plasma and is removed, or material is deposited from the plasma onto the surface. Therefore, the nature of the surface is as important as that of the plasma. The following table can be constructed summarizing the effect of different plasmas on different surfaces.

| SURFACE | PLASMA GAS | | |
|---|---|---|---|
| | $CF_4$ | $CHF_3$ | $O_2$, $H_2$, $H_2O$, Argon, $N_2$ |
| Silicon Dioxide | etching/ hydrophilic | deposition/ hydrophobic | etching/ hydrophilic |
| Polyimide | deposition/ hydrophobic | deposition/ hydrophobic | etching/ hydrophilic |
| Silver | etching/ hydrophilic | deposition/ hydrophobic | etching/ hydrophilic |

Such processes have the clear advantage of modifying a surface, in a controlled manner, from ore which is highly wettable to one which is non-wettable. The effective contact angle of the control material is determined by the composition of the gas and the power, duration, and pressure of the plasma.

Prior to microdispensing the preferred fluid compositions described above, the silicon wafers with microfabricated base sensors and polyimide passivation layers may be plasma treated under any of the above listed conditions. Hence, the argon plasma has the effect of etching the surface (hydrophilic), whereas the $CF_4$ plasma makes the surface more hydrophobic. Ultimately, a tailored surface energy affords control over the spreading of the material of a microdispensed fluid or membrane material. Control over the spreading affords control over the membrane thickness. Control over the membrane thickness leads, in turn, to highly reproducible membrane response characteristics.

Figure 16A:
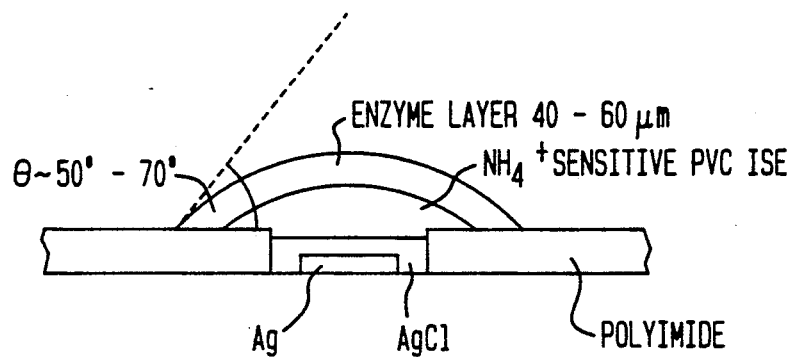
FIGS. 16a–16c show various embodiments of microdispensed biolayers including one which has a large contact angle (FIG. 16a), one with a small contact angle (FIG. 16b), and one which has subsequently been subjected to a photopatterning step (FIG. 16c).

For establishing thick membranes, (e.g., 40-60 $\mu m$ thick), the surface is preferably tailored so that the contact angle which the microdispensed fluid makes with the surface is large. For example, before as aqueous latex membrane is microdispensed, the surface is first plasma treated to yield a contact angle for water (control fluid) in the range 50°-70°. This point is illustrated in FIG. 16a for a potentiometric ammonium ion sensor.

Figure 16B:
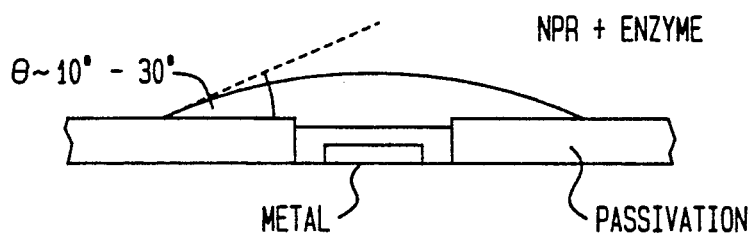

For thin membranes the surface is tailored to have a low contact angle for the dispensed fluid (e.g., for a 1 $\mu m$ NPR enzyme layer microdispensed as an aqueous solution, the contact angle may be 10°-30° (See, FIG. 16b).

Figure 16C:
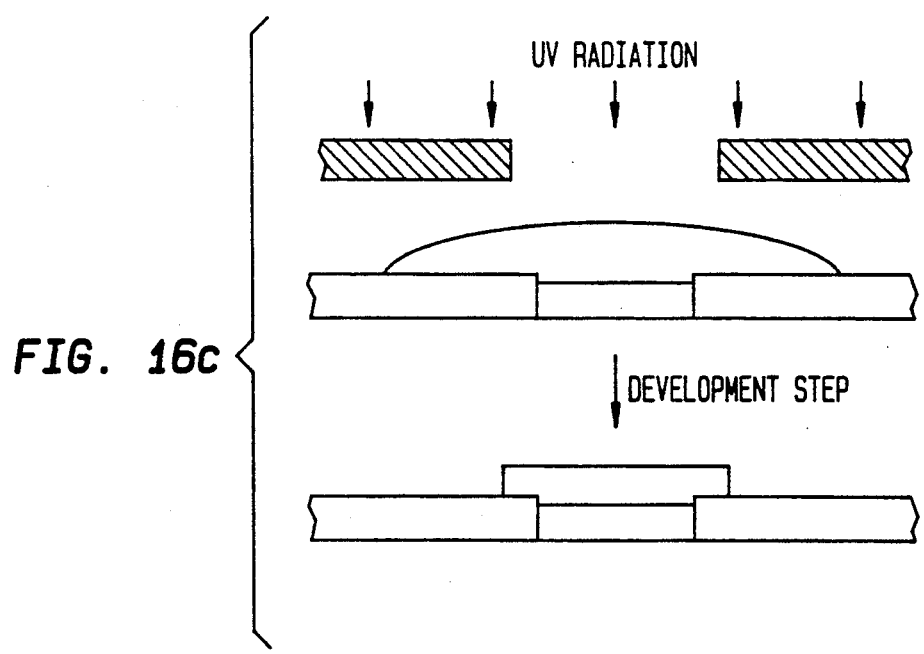

In a specific embodiment of the present invention, the surface energy of the perimeter of an electrode surface is tailored in such a fashion to create conditions under which one obtains the desired membrane thickness upon dispensing of a given volume of a photoformable proteinaceous mixture. The dispensed fluid flows in a controlled manner and produces a film of a controlled thickness. As illustrated in FIG. 16c, subsequent exposure of the resulting film to active radiation, at preselected areas of the photoresist film, renders those exposed areas insoluble to a developing medium. A patterned layer is obtained after the development step. The dimensions of the resulting layer are controlled, therefore, in a manner and degree not unlike that obtained through spin-coating. A major difference, of course, is that by employing the methods of the present process, numerous types of membranes, bearing a variety of bioactive molecules, can be established in a single wafer without compromising the control and reproductibility of an ideal microfabrication process. Hence, a multiple syringe assembly, such as that illustrated in FIG. 13, may be employed to dispense several types of biolayers. All the resulting layers may then be localized further to preselected areas of the electrode by exposure to a single photopatterning step.

5.5. Creatinine and Creatine Sensors

Preferred embodiments for a creatinine sensor and a creatine sensor are also described in the examples section of the disclosure. To attain the maximum activity of the immobilized enzymes for the creatinine assay, creatinine amidohydrolase and sarcosine oxidase are immobilized in a photoformed gelatin layer. The creatinase is then immobilized in a film-forming latex applied as an overlaid structure. The creatine sensor is constructed in a similar manner, with the creatinine amidohydrolase being omitted from the gelatin layer. As these examples show structures and processes which combine the photoformable gelatins with the film-forming latices are readily obtained.

5.6. Other Characteristics

The sensors described herein are designed to be compatible with a disposable sensing device. For a disposable sensing device for use in real time fluid analysis (See, co-pending U.S. application Ser. No. 07/245,102, the entire disclosures of which is incorporated herein by reference). These sensors must therefore have the capability of retaining an excess amount of enzyme to ensure an extended shelf-life when stored dry. The layers must be thin enough and permeable enough, however, such that wet-up, calibration, and a measurement of an analyte in a biological fluid can all be performed in real time, preferably within a total of about one minute. With respect to the amperometric sensor for glucose, electrical pulsing of the electrocatalyst prior to the calibration and measurement steps, is advised to activate the electrocatalyst surface and help ensure the highest possible hydrogen peroxide currents. These sensors are also designed to be compatible with a static-free interrogating (SMART) connector for electrical components (See, co-pending U.S. application Ser. No. 187,665, the complete disclosure of which is incorporated herein by reference). The following examples serve to illustrate the general aspects of the present invention and are not to be construed as limiting, in any way, its scope and utility. Other embodiments may become apparent to those of ordinary skill which do not depart significantly from the scope and spirit of the present invention and may, therefore, be deemed equivalent thereto.

6. EXAMPLES

6.1. Glucose Sensor

6.1.1. BASE SENSOR FABRICATION WITH SIGNAL LINE PASSIVATION

The preferred design for a glucose sensor is a unit cell which comprises two identical iridium catalytic electrodes both surrounded by a single silver-silver chloride combined reference and counter electrode (See, FIGS. 1 and 2). Each of the three electrodes is connected by an over-passivated signal line to one of three contact pads. The unit cell is confined within a rectangular area which is repeated in a square array several hundred times on a single substrate, in this case, a silicon wafer.

A four-inch diameter silicon wafer with a topical layer of silicon dioxide, which had previously been cleaned scrupulously with a concentrated mixture of sulfuric acid and hydrogen peroxide, is placed into a plasma deposition system. Layers of titanium (0.1 $\mu$m) and silver (0.5 $\mu$m) are sputtered consecutively onto the wafer surface. The silver is then processed to localize it to a region which in the final device acts as the combined reference and counter electrode. This step is achieved by a standard lithographic technique in which the wafer is spin-coated with positive resist (Shipley, AZ®1370 SF). After UV exposure of the photoresist through a mask and development (Shipley, AZ 351), the exposed silver is removed by using a 0.9M aqueous solution of ferric nitrate as the etchant. N-methylpyrrolidone solvent is used to remove the remaining photoresist, thus exposing the required silver structure. The underlying titanium layer is then processed to leave material in regions which act as either a contact pad or a signal line. This process is achieved by repeating the same lithographic process, as described above for silver, with the exception that a 3.9M aqueous mixture of nitric acid also containing 0.78M of hydrofluoric acid is used as the etchant.

To passivate the signal lines a photo-definable polyimide (DuPont 2703) is spin-coated onto the wafer. Once the wafer has been exposed to UV light and developed with a solvent mixture of butyrolactone and xylene (6:4 v/v), the polymer is heated and "imidized" in an oven at about 350° C. for about 30 minutes under an inert atmosphere and left to cool to about 150° C. before removal.

To fabricate the iridium catalytic electrode, positive photoresist (AZ®Shipley, 1370 SF) is patterned as described above. A layer of iridium (0.1 $\mu$m) is then sputtered onto the wafer. Excess photoresist and excess metal on the resist are then removed by treatment with N-methylpyrrolidone to leave an octagonal (width 200 $\mu$m) iridium layer. The areas of silver are then chloridized by dipping the entire wafer into a 12 mM aqueous solution of potassium dichromate also containing 60 mM hydrochloric acid.

To sensitize the catalytic electrode specifically to glucose, additional layers are established on the base sensor.

6.1.2. PERMSELECTIVE SILANE LAYER

An alcoholic solution of the silane compound, N-(2-aminoethyl)-3-aminopropyltrimethoxysilare, is prepared as follows: 10 g of a mixture comprising the silane (2 mL), water (9 mL), and ethanol (90 mL) is mixed with 50 g of ethanol. A sufficient amount of this alcoholic silane solution is spin-coated onto a wafer. The wafer is then baked in an oven at about 90°–250° C. for about 5–30 minutes.

Alternatively, the silane layer can be established on preselected areas (i.e., over the catalytic electrode surface) of the silicon wafer having the base sensor in place. Hence, a layer of positive photoresist (Shipley, AZ®1370 SF) is spin-coated across the wafer and soft-baked at about 90° C. for 30 minutes. It is then patterned as described previously to leave the area over the catalytic electrode exposed. A 0.5 g/dL solution of N-(2-axinoethyl)-3-aminopropyltrimethoxysilane in deionized water is then spin-coated onto the wafer and baked at about 90° C. for 15 minutes under an inert atmosphere. Excess polyxerized silane and photoresist is then removed by means of ultrasonication in n-butylacetate for about 15 minutes. After the photoresist is removed the wafer is post-baked at about 160° C. for 15 minutes. This "lift-off" process yields a wafer in which the silane layer is localized over the catalytic electrode.

If one prefers, the silane layer may also be established locally by means of a photoresist cap. A typical procedure is outlined below:

A silicon wafer with a patterned array of amperometric electrochemical sensors, in which the catalytic working electrode is a thin-film of iridium metal and the reference electrode is silver-silver chloride, is spin-coated with a 0.5 g/dL solution of N-(2-aminoethyl)-3-aminopropyl trimethoxysilane in deionized water. The wafer is then heated to about 160° C. for about 15 minutes. The wafer is then spin-coated with positive photoresist (Shipley, AZ®1370 SF), soft-baked at about 100° C. for about 60 seconds, and then patterned by means of exposure to ultraviolet light through a mask. The resist is then developed (AZ ®Shipley, 351) to leave a resist cap over the catalytic iridium working electrode. The wafer is then etched in a 1/500 fold dilution of hydrofluoric acid (10M) in deionized water to remove excess polymerized N-(2-aminoethyl)-3-aminopropyltrimethoxysilane. Other protic solvents, such as lower alkanols, may be used as the solvent for the hydrofluoric acid. Mixtures of protic solvents may also be used. Typically the concentration of hydrofluoric acid in the protic solvent lies in the range of about 0.001 to about 0.01 weight percent. The resist cap is then removed by exposure of the wafer to n-butylacetate followed by ultrasonication for 15 minutes. The above procedure leaves the silane layer only on the catalytic electrodes.

In an alternative method, the wet etch step involving hydrofluoric acid is replaced by a dry etch using an oxygen plasma, achieving similar results.

6.1.3. PHOTOFORMABLE FISH GELATIN AS SUPPORT MATRIX FOR BIOLAYER

Photoformable fish gelatin containing ferric ammonium citrate as photoinitiator may be purchased from Norland Products, Inc., New Brunswick, N.J. These negative photoresists (the commercial materials are referred to as NPR followed by an integer) may also be prepared fresh by mixing aqueous solutions of fish gelatin (cold water fish skin sold as a 45% aqueous solution by Sigma Chemical Company, Cat. No. G 7765), metal complex, and a crosslinking agent.

A sugar alcohol, such as sorbitol or mannitol, may also be included in the formulation to alter the porosity of the photoformed matrix. As noted previously, a commercial formulation known as NPR 6, which contains a chromium-based photoinitiator, may also be used.

The enzyme biocatalyst, glucose oxidase (in the present example), may be mixed into the NPR or freshly prepared fish gel mixture and spin-coated across the base sensor wafer. A typical formulation may comprise about 2 to about 35 g/dL fish gelatin, about 2 to about 100 mM metal complex, about 2 to about 100 mM crosslinking agent, and about 1 to about 25 mg/mL enzyme. The formulation may also contain about 0.1 to about 10 g/dL sugar alcohol and about 0.001 to about 1 g/dL of a detergent. A preferred formulation comprises 10% fish gelatin, 13.3 mM ferric citrate, 13.3 mM N,N'-methylenebisacrylamide, and 6.7 mg/mL glucose oxidase. Another suitable formulation comprises NPR-29 (diluted with deionized water to a final protein content of 10% by weight of the total mixture), glucose oxidase (6.7 mg/mL), sorbitol (2 g/dL), and Triton X-100 (0.03 g/dL). The pH of the fish gelatin or NPR formulations may be adjusted with added carbonate or sodium hydroxide, if desired, to a pH above about 4 before addition of the enzyme. Most preferably, the pH of the formulation should be greater than about 4 but less than about 9 to prevent a significant inactivation of the biocatalyst.

The amount of proteinaceous material applied on the wafer can be varied to adjust the thickness of the final biolayer. Preferably, this thickness is about 0.1 $\mu$m. More economically, the formulations may be microdispensed directly over the indicator electrodes of the base sensors. The wafers are then exposed to UV light (6 mW/cm$^2$, 30 seconds) through an appropriate mask and developed in 1 g/dL aqueous hydrogen peroxide for about 20 seconds.

Alternatively, the protein matrix may be established and patterned on the wafer without the enzyme present. The entire wafer may then be immersed in an aqueous solution of the enzyme glucose oxidase (Sigma type VII: 150 IU/mg) at a concentration of 20 mg/mL for 2 minutes. This procedure is effective to impregnate the gelatin layer with a sufficient amount of enzyme. Excess enzyme can be removed by washing the wafer with water.

6.1.4. GLUCOSE SENSOR WITHOUT SIGNAL LINE PASSIVATION AND USE OF CHROMIUM-BASED NPR MATRIX

An alternative design for a glucose sensor is a unit cell which comprises two identical iridium catalytic electrodes both surrounded by a single silver-silver chloride combined reference and counter electrode (See, FIGS. 1 and 2). Each of the three electrodes is connected by an unpassivated signal line to one of three contact pads. Elimination of the passivation step reduces the number of manufacturing steps. The absence of the passivation layer also reduces the gross topography on the wafer and allows better control of the thickness of materials which are subsequently spin-coated across the wafer. The unit cell is confined within a rectangular area which is repeated in a square array several hundred times on a single substrate, in this case, a silicon wafer.

A four-inch diameter silicon wafer with a topical layer of silicon dioxide, which had previously been cleaned scrupulously with a concentrated mixture of sulfuric acid and hydrogen peroxide, is placed into a plasma deposition system. Layers of titanium (0.1 $\mu$m) and silver (0.5 $\mu$m) are sputtered consecutively onto the wafer surface. The silver is then processed to localize it to a region which in the final device acts as the combined reference and counter electrode and the contact pads. This step is achieved by a standard lithographic technique in which the wafer is spin-coated with positive resist (Shipley, AZ ®1370 SF). After UV exposure of the photoresist through a mask and development (Shipley, AZ ®351), the exposed silver is removed by using a 0.9M aqueous solution of ferric nitrate as the etchant. N-methylpyrrolidone solvent is used to remove the remaining photoresist, thus exposing the required silver structure.

To fabricate the iridium catalytic electrode, positive photoresist (Shipley, AZ ®1370 SF) is patterned as described above on the wafer and then a layer of iridium (0.1 $\mu$m) is sputtered onto the wafer. Excess photoresist is then removed by treatment with N-methylpyrrolidone to leave an octagonal (width 200 $\mu$m) iridium layer. The underlying titanium layer is then processed to leave material in regions which act as either a contact pad or a signal line. This process is achieved by repeating the same lithographic process, as described above for silver, with the exception that a 0.78M aqueous solution of hydrofluoric acid is used as the etchant.

The areas of silver are then chloridized by dipping the entire wafer into a 12 mM aqueous solution of potassium dichromate also containing 60 mM hydrochloric acid. The remaining photoresist is then removed with N-methylpyrrolidone.

The silane layer is then localized over the iridium electrode with the aid of photolithographic techniques described previously in Section 6.1.2, above. After the silane-coated wafer is baked at about 160° C. for about 15 minutes, Norland NPR material, diluted to 7.5 g/dL solids and also containing the enzyme glucose oxidase (Sigma type VII:150 IU/mg) at a concentration of 20 mg/mL. is spin-coated onto the wafer to provide a coating about 0.1 $\mu$m in thickness. After UV exposure through the appropriate mask, the enzyme-containing negative photoresist is developed in water providing a self-aligned biolayer positioned directly over the iridium indicator electrode.

6.1.5. ANALYTE ATTENUATION AA) LAYER

Dimethylsiloxane-bisphenol A carbonate copolymer (3 g/dL solution) dissolved in a solvent mixture of phenetole and dichloromethane (4:1 v/v) is spin-coated onto the wafer. Subsequently, the wafer is etched for 10 seconds in an argon plasma. A layer (0.2 μm) of NPR (diluted to 15 g/dL solids) is then spin-coated over the siloxane copolymer. The gelatin layer is exposed to UV light through a mask and developed in water to provide a protective octagonal cap 450 μm in width, centered over the catalytic iridium electrode and above the underlying siloxane copolymer. The excess unprotected siloxane is then removed by a wet etching agent (a 17 g/dL solution of tetramethylammonium hydroxide in a solvent mixture of methanol and isopropylalcohol (2:1 v/v)). The wafer is then washed and diced into individual sensors and stored essentially dry under a controlled humidity environment.

As noted earlier, numerous enzymes may be immobilized by a process similar to that described above. Persons skilled in the art need only carry out a minimum amount of experimentation to determine the feasibility of immobilizing a given enzyme or mixture of enzymes. In addition to fish gelatin, other materials, such as bovine or human serum albumin (BSA or HSA), gamma-globulin, casein, or other animal gelatins may serve as possible sources of protein provided that a given combination of protein, crosslinking agent, photoinitiator, and other additives is found to have suitable negative photoresist characteristics.

6.2. Preparation of LLR-Based Biosensors and Methods for the Use Thereof

6.2.1. BASE SENSOR FABRICATION

A four inch diameter silicon wafer with a topical layer of silicon dioxide which had previously been unscrupulously cleaned with a concentrated mixture of sulfuric acid and hydrogen peroxide is placed into a plasma deposition system and layers of titanium (about 0.1 μm) and silver (about 0.5 μm) are sputtered onto the wafer surface. The silver is then processed by standard lithographic techniques to localize it to a region which in the final device acts as the combined reference and counter electrode (See, e.g., Level 4, FIG. 17A). The wafer is spin-coated with positive resist (AZ®1370 SF), subjected to UV exposure of the photoresist through a mask, and then developed (AZ®351). The exposed silver is removed by using an aqueous solution of ferric nitrate (0.9M) as the etchant. Removal of the remaining photoresist to expose the required silver structure is done with N-methylpyrrolidone. The underlying titanium layer is then processed to leave material in regions which act as either a contact pad or a signal line. This step is achieved by repeating the same lithographic process, as described previously for silver, with the exceptions that a different mask is used and the etchant is an aqueous mixture comprising nitric acid (3.9M) and hydrofluoric acid (0.78M). To passivate the signal lines a photo-definable polyimide (DuPont 2703) is spin-coated onto the wafer. Once the wafer is UV exposed and developed with a mixture of butyrolactone and xylene (6:4 v/v), the polymer was imidized in an oven at 350° C. for 30 minutes in an inert atmosphere and allowed to cool to 150° C. before removal from the oven.

To fabricate the catalytic electrode, positive photoresist (AZ®1370 SF) is patterned or the wafer and then a layer of the electrocatalyst metal is sputtered onto the wafer. For iridium such deposition is preferably carried out at a rate of about 0.4 nm/sec to a thickness of about 20 nm; for gold, the preferred rate of deposition is about the same but to a thickness of about 100–120 nm. Excess photoresist is removed by treatment with N-methylpyrrolidone to leave an octagonal (width 200 μm) catalytic layer (See, Level 5, FIG. 1).

The areas of silver were then chloridized by dipping the entire wafer into an aqueous solution comprising potassium dichromate (12 mM) and hydrochloric acid (60 mM).

6.2.2. POST-PROCESSING OF BASE SENSOR

After processing, the wafers are scribed. For example, wafers which are about 0.46 mm thick, are scribed (partially diced) along both the X and Y axes defined by the rectangular unit cell of the sensor such that about 0.18 mm of the silicon substrate remains. This technique provides the necessary structural integrity for the steps which follow, (e.g., deposition of the biolayers) but permits the easy separation of the wafer into individual sensors upon completion of the process.

The base sensors, exemplified above are processed further into LLR-based biosensors by establishing additional layers which have an affinity for the desires analyte species. Methods for establishing additional suitable layers are described further.

6.2.3. LAYERS FOR THE DETECTION AND MEASUREMENT OF HUMAN IgG

This particular embodiment comprises two additional layers above the iridium base sensor: a silane layer which permits dioxygen and hydrogen peroxide transport and also serves as an anchor to which the second layer of an immunologically reactive first member is covalently bound.

To establish the silane layer onto the wafer, a 0.05 g/dL solution of N-(2-aminoethyl)-3-aminopropyl-trimethoxysilane in a mixture of isopropanol:water (92:8, v/v) is spin-coated onto the scribed wafer and baked in an oven at 90° C. for 20 minutes. The wafer is allowed to cool to ambient temperature. Subsequently, the layer is patterned in the manner described previously in Section 6.1.2. The wafer is then soaked in a 1 g/dL aqueous solution of glutaraldehyde for 1 hour at ambient temperature and, afterwards, air-dried at ambient temperature.

A solution (100 nL) containing 2.65 mg/mL of goat anti-human IgG antibody (first member) in 0.01 M sodium phosphate buffer with 0.25M NaCl, pH 7.6, is then microdispensed automatically onto individual iridium electrodes on the wafer. During microdispensing, the wafer is placed in a controlled humidity chamber, to prevent drying, at ambient temperature for 20 minutes. Unbound receptor is then removed by washing the wafer with deionized water. The sensor may then be stored dry.

6.2.4. ANALYTE: THEOPHYLLINE

A wafer having base sensors equipped with gold catalytic electrodes is processed in exactly the manner described in Section 6.2.3. with the exception that microdispensing of the first member utilized an antitheophylline antibody.

6.2.5. AN LLR-BASED BIOSENSOR FOR HUMAN IgG EQUIPPED WITH UNDERLYING

ELECTROLYTE AND GAS PERMEABLE LAYERS

A wafer with gold catalytic electrodes as described above is spin-coated with a mixture of negative photoresist NPR 6 (by Norland, New Brunswick, N.J.) to provide a layer having a thickness of about 1 μm. The coated wafer is then introduced to an oxygen plasma for 10 seconds, before a solution of siloxane-nonsiloxane copolymer, dimethylsiloxane bisphenol A carbonate available from Petrarch, Pa. (6 g/dL in chlorobenzene), is spin-coated onto the wafer to provide a layer having a thickness of about 0.7 μm. The wafer is again exposed to an oxygen plasma for 10 seconds. Finally a second layer of negative photoresist, NPR 6, is established on the wafer at a thickness of about 0.7 μm.

The wafer is then exposed to UV radiation through a mask corresponding to the area over the electrode structures. The topmost layer of negative resist is developed in deionized water for 5 seconds to provide a cap for etching the underlying siloxane-nonsiloxane copolymer layer (gas permeable). Etching of the copolymer layer is achieved with a 0.2M solution of potassium hydroxide in a mixture of methanol and isopropanol (1:5 parts by volume). Finally the bottom (first) layer of negative photoresist is developed in deionized water.

After the wafer is washed and scribed, goat anti-human IgG antibody is immobilized onto the sensor surface in the manner described previously in Section 6.2.3., preferably with a glutaraldehyde crosslinker. The resulting structure resembles that shown in FIG. 7A except that the ligand receptor or immunoreactive species is also present over the photoresist layer, 9.

6.2.6. ALTERNATIVE THEOPHYLLINE BIOSENSOR

A set of three layers based on negative photoresist and a siloxane non-siloxane copolymer as described in Section 6.2.5. are fabricated with one change in the process. After spin-coating of the first NPR 6 layer, the wafer is exposed to UV radiation through a mask corresponding to the preselected areas over the electrode and then developed in deionized water. Subsequently, the additional siloxane non-siloxane copolymer and NPR 6 layers are deposited and patterned in a manner corresponding to the enclosed structure of FIG. 7B.

After washing and scribing, the wafer is further processed to establish the immobilized ligand receptor layer, in this case an anti-theophylline antibody layer. The final structure resembles that illustrated in FIG. 8B.

6.2.7. ASSAY PROCEDURE FOR THE ANALYSIS OF HUMAN IgG

Affinity purified goat anti-human IgG is immobilized on a microfabricated LLR-based biosensors as described in Sections 6.2.1 to 6.2.3. An equal volume of a test serum containing human IgG (analyte) and enzyme-labeled antibody (goat anti-human IgG-enzyme) are pre-mixed and 5 μL of the resulting mixture are added to the immunosensor. Samples of Phosphate Buffered Saline (2.5 mM Sodium Phosphate Monobasic, 7 5 mM Sodium Phosphate Dibasic, and 0.145M Sodium Chloride, pH 7.2), or whole blood containing human Immunoglobulin G, mixed with an equal volume of goat anti-human Immunoglobulin G labeled with alkaline phosphatase can be used instead of the serum sample. An LLR-based biosensor, as described in Section 6.2.5, is also suitable, indeed preferable, in the present method.

The immunosensor and the mixture are then incubated for about 15 minutes at about 37° C. to allow for the binding of the human IgG in the test serum to the goat anti-human IgG (capture receptor) immobilized on the immunosensor. The immunosensor is washed briefly to remove any non-specifically bound proteins. The washing can be effected using a first wash with distilled and deionized water containing 0 1% (v/v) Tween 20 (polyoxyethylene sorbitan monolaurate); and a second wash step using only deionized water. This wash step may alternatively be accomplished by the introduction of a solution containing 3.0 mM indoxyl phosphate, a substrate for alkaline phosphatase. This addition results, eventually, in the production of hydrogen peroxide and the consumption of dioxygen. The amount of electroactive species produced or consumed is directly proportional to the amount of human IgG in the serum. In assays consuming dioxygen, the presence of 10 ng/mL immunoglobulin G can be detected. The entire assay is accomplished in less than twenty minutes. However, it will be appreciated that the sensitivity of the assay may be adjusted by varying the concentrations or incubation times.

Standard curves can be stored preferably as a linear function in the electronics memory of the overall device (See, for example, prior co-pending U.S. application Ser. No. 245,102). It is understood that change in hydrogen peroxide may also be detected, using, preferably, an iridium metal electrocatalyst.

6.2.8. ASSAY PROCEDURE FOR THE ANALYSIS OF THEOPHYLLINE

An affinity purified mouse anti-theophylline antibody is immobilized onto an LLR-based biosensor as described in Sections 6.2.4 and 6.2.6, supra. An equal volume of a test serum containing theophylline and enzyme-labeled theophylline are pre-mixed. A portion of the resulting mixture (5 uL) is added to the immunosensor. The mixture is then incubated with the immunosensor for a finite time at a fixed temperature, for example, at 15 minutes at 37° C., to allow for the binding of the theophylline in the sample to the immobilized antibody on the immunosensors. The immunosensor is then washed briefly to remove any non-specifically bound proteins. The washing can be effected using a first wash with distilled and deionized water containing 0.1% (v/v) Tween 20, followed by a second wash step using only deionized water. Alternatively, a solution containing 3.0 mM indoxyl phosphate, a substrate for alkaline phosphatase is then added, serving as the wash solution and resulting in the production of hydrogen peroxide and consumption of dioxygen. The amount of electroactive species produced or consumed gives rise to a change in the concentration of the electroactive species of interest, which change is inversely proportional to the amount of theophylline in the sample. In assays consuming dioxygen, the presence of less than 2.5 ug/mL theophylline can be detected. The entire assay is accomplished in less than about twenty minutes. It will be appreciated that the sensitivity of the assay may be adjusted by varying the concentrations or incubation times.

6.3. Uric Acid Sensor

The preferred embodiment for a uric acid sensor utilizes the base sensor described previously for a glucose sensor. Also, although the design of the biolayers is the same as for the glucose sensor, the fabrication of the biolayers is slightly different.

A 0.3 g/dL solution of N-(2-aminoethyl)-3-aminopropyltrimethoxysilane in a solvent mixture of ethanol and water (92:8 v/v) is spin-coated onto the base sensor wafer and baked in an oven at 17° C. for 15 minutes. Photoformable fish gelatin (Norland NPR) is then mixed (1:4 parts) with a solution of uricase (Toyobo 15 mg/mL: 6.63 IU/mg) and automatically microdispensed directly over the catalytic iridium electrodes of the wafer. Sufficient material (10–100 nL) is deposited in this technique to allow for the coverage of an area about three times the diameter of the catalytic iridium electrode. After drying, the wafer is UV exposed through a mask and developed in a solution of 0.6% hydrogen peroxide to yield a self-aligned cross linked gelatin/uricase layer having a thickness of about 0.6 μm positioned directly over the catalytic iridium electrode.

A 3 g/dL solution of dimethylsiloxane-bisphenol A carbonate polymer dissolved in a solvent mixture of phenetole and dichloromethane (2:1 v/v) is spin-coated onto the wafer. Subsequently the wafer is etched for 10 seconds in an argon plasma. A layer (1.0 μm) of photoformable gelatin (Norland NPR) is then spin-coated over the siloxane copolymer. Once the gelatin layer is UV exposed and developed in water to provide a protective cap self-aligned above the catalytic iridium electrode and over the underlying siloxane copolymer, excess siloxane is removed by a wet etching agent (a 17 g/dL solution of tetramethylammonium hydroxide in a mixture of methanol and isopropylalcohol (2:1 v/v)). The wafer is then washed and diced into individual sensors; these sensors are stored essentially dry in a controlled humidity environment.

6.4. Co-Processed Glucose and Cholesterol Sensor

The preferred embodiment for a dual-analyte combined sensor that is processed with a single development step for the enzyme layers is described for glucose and cholesterol.

A silicon wafer, processed by standard microfabrication techniques described above, in the preferred embodiment for the single glucose sensor, is used. The wafer which is 0.46 mm thick is partially diced or scribed along both the X and Y axes defined by the rectangular unit cell of the sensor, such that only about 0.18 mm of the silicon substrate remains. This procedure provides the necessary structural integrity for the steps which follow, but permits the easy cleavage of the wafer into individual sensors at the end of the process.

The wafer is spin-coated with a solution of 0.3 g/dL N-(2-aminoethyl)-3-aminopropyltrimethoxysilane (ethanol:water, 99:1, v/v) and then heated under an inert atmosphere at about 170° C. for about 15 minutes. A mixture (0.15 mL) containing 0.07M sodium carbonate, 2.0 g/dL sorbitol, 0.033 g/dL Triton X-100 (PEG, Rohm and Haas), 6.7 mg/mL glucose oxidase (Sigma type VII; 150 IU/mg), and 0.05 mL of a fish gelatin (Norland NPR 29) is applied to the center of the catalytic iridium electrode using an automated microdispensing device. The volume is adjusted (10–100 nL) such that the liquid spreads over an area approximately three times the diameter of the catalytic iridium electrode.

A second mixture of the same composition as above but containing 6.7 mg/mL of cholesterol oxidase (Toyobo type A; 261 IU/mg) is then applied by the same technique to the adjacent catalytic iridium electrode on each sensor.

After drying under ambient conditions, the wafer is exposed to UV light through a mask so that only the region above each catalytic iridium electrode receives light. Then the wafer is developed by immersion and gentle agitation for 20 seconds in freshly prepared 0.1 g/dL aqueous hydrogen peroxide to yield crosslinked gelatin/enzyme layers about 0.5 μm in thickness self-aligned over the catalytic iridium electrodes.

Alternatively, a fish gelatin formulation comprising 5 g/dL fish gelatin from Sigma, 4 g/dL, ferric ammonium citrate, 6.7 mM N,N'-methylenebisacrylamide, 2 g/dL sorbitol, 0.033 g/dL Triton X-100, and 6.7 mg/mL enzyme (glucose oxidase or cholesterol oxidase or both) can be microdispensed onto the indicator electrode, exposed for 30 seconds (6 mW/cm$^2$), and developed for about 20 seconds in 0.3 g/dL aqueous hydrogen peroxide.

A solution of dimethylsiloxane-bisphenol A carbonate copolymer (0.1 g), dichloromethane (0.9 g), chlorobenzene (17.0 g), and diphenylether (3.0 g) is then microdispensed directly over the crosslinked gelatin/enzyme layers to cover an area about three times the diameter of the catalytic electrode. Finally, the wafer is cleaved to give combined glucose and cholesterol sensors. These devices are stored, as usual, dry.

6.5. Adenosine-5-Triphosphate Sensor

The preferred embodiment for an adenosine-5-triphosphate (ATP) sensor utilizes the base sensor as described previously for the glucose sensor. However, the wafer is scribed before the biolayers are applied as described previously for the preferred embodiment of the combined glucose and cholesterol sensor.

A 0.3 g/dL solution of N-(2-aminoethyl)-3-aminopropyltrimethoxysilane in a solvent mixture of ethanol and water (92:8 v/v) is spin-coated onto the base sensor wafer and baked in an oven at 170° C. for 15 minutes. Photoformable fish gelatin (Norland NPR 29) is then mixed (1:4 v/v) with an aqueous solution containing glycerol kinase (Toyobo 15 mg/mL; 28 IU/mg) and glycerol-3-phosphate oxidase (Toyobo 15 mg/mL; 84.4 IU/mg). The resulting mixture is then automatically microdispensed directly over the catalytic iridium electrodes on the wafer. Sufficient material (10–100 nL) is deposited by this technique to allow for the coverage of an area approximately three times the diameter of the catalytic iridium electrode. After drying at ambient conditions, the wafer is UV exposed through a mask and developed in a solution of 0.6 g/dL hydrogen peroxide to yield a self-aligned crosslinked gelatin/bienzyme layer of 0 6 μm thickness positioned directly over the catalytic iridium electrode. The wafer is then washed and cleaved into individual sensors. These devices are stored dry.

6.6. Alternative Embodiment of an Adenosine-5-Triphosphate Sensor

Yet another embodiment of the adenosine-5-triphosphate (ATP) sensor utilizes the base sensor as described previously for the glucose sensor. However, the wafer is partially diced before the biolayers are applied as described, supra.

A 0.3 g/dL solution of N-(2-aminoethyl)-3-aminopropyltrimethoxysilane in a solvent mixture of ethanol and water (92:8 v/v) is spin-coated onto the wafer and baked in an oven at 170° C. for 15 minutes. A film forming latex (Elvace 40711-00, Reichhold) is then mixed (1:1 v/v) with an aqueous solution of glycerol kinase (Toyobo 15 mg/mL; 28 IU/mg), glycerol-3-phosphate oxidase (Toyobo 15 mg/mL; 84.4 IU/mg), and glutaraldehyde (2 mM). The resultant mixture is microdispensed directly over the catalytic iridium electrodes on the wafer. Sufficient material (10-100 nL) is deposited by this technique to allow for the coverage of an area about twice the diameter of the catalytic iridium electrode. After drying, the partially diced wafer is then washed and cleaved into individual sensors. These devices are stored dry.

6.7 Creatinine Sensor

The preferred embodiment of a creatinine sensor utilizes the base sensor described previously for the glucose sensor. The fabrication of the biolayers is different, however.

A 0.3 g/dL solution of N-(2-aminoethyl)-3-aminopropyltrimethoxysilane in a solvent mixture of ethanol and water (92:8 v/v) is spin-coated on the wafer and baked in an oven at 170° C. for 15 minutes. Photoformable fish gelatin (Norland NPR 29) is then mixed (1:4 v/v) with an aqueous solution of Creatinine amidohydrolase (Toyobo 15 mg/mL; 2.29 IU/mg) and sarcosine oxidase (Toyobo 15 mg/mL; 4.9 IU/mg). The mixture is microdispensed directly over the catalytic iridium electrodes on the wafer. Sufficient material (10-100 nL) is deposited by this technique to allow for the coverage of an area about three times the diameter of the catalytic iridium electrode. After drying, the wafer is UV exposed through a mask and developed in a solution of 0.6 g/dL hydrogen peroxide to yield a self-aligned crosslinked gelatin/bienzyme layer of 0.6 μm thickness positioned directly over the catalytic iridium electrode.

The film-forming latex (poly(vinyl acetate-co-vinyl alcohol), Reichhold) is mixed (1:1 v/v) with an aqueous solution of creatine amidinohydrolase (Toyobo 15 mg/mL; 12.8 IU/mg). This mixture is automatically microdispensed directly over the patterned gelatin layers already present on the wafer. Sufficient material (10-100 nL) is deposited to ensure complete coverage of an area about twice the diameter of the gelatin layers.

After drying the previously scribed wafer is then washed and cleaved into individual sensors. These devices are stored dry.

6.8. Creatine Sensor

The preferred embodiment of a creatine sensor is exactly the same as that for the creatinine sensor except that the enzyme creatinine amidohydrolase is omitted from the initial gelatin layer.

6.9. Blood Urea Nitrogen (Bun) Sensor

A silicon wafer with a topical layer of silicon dioxide which had previously been cleaned scrupulously with a mixture of concentrated sulfuric acid and hydrogen peroxide is placed into a plasma deposition system and layers of titanium (0.1 μm) and silver (0.5 μm) are sputtered consecutively onto the wafer surface. The silver-titanium bilayer is then processed to localize it to a region which in the final device acts as the ammonium ion sensor. This process is achieved by a standard lithographic technique in which the wafer is spin-coated with positive resist (Shipley AZ ®1370 SF). After UV exposure of the photoresist through a mask and development (AZ ®Shipley 351), the exposed silver is removed by an aqueous solution of ferric nitrate (0.9 mM) as the etchant. The underlying titanium layer is then processed by means of the same photolithographic steps, but using an aqueous mixture of nitric acid (3.9M) and hydrofluoric acid (0.78M) is used as the etchant. N-methylpyrrolidone solvent is then used to remove the remaining photoresist to expose the required octagonal silver structures (width about 150 μm).

To passivate the signal lines a photo-definable polyimide (DuPont 2703) is spin-coated onto the wafer. Once the wafer is UV exposed and developed with a solvent mixture of butyrolactone and xylene (6:4 v/v), the polymer is baked in an oven at 350° C. for 30 minutes under an inert atmosphere and left to cool to 150° C. before removal.

The silver is then chloridized by dipping the entire wafer into an aqueous solution of potassium dichromate (12 mM) and hydrochloric acid (60 mM). Over these patterned silver chloride electrodes is placed an ammonium ion sensitive membrane. The membrane material is made by dissolving low molecular weight PVC (Sigma) and high molecular weight carboxylated PVC (Type Geon, Goodrich) (1:1 w/w) in a solvent system of cyclohexanone, propiophenone, and N-methylpyrrolidone (1:1:1 v/v/v) to a total solids content of 10 g/dL of solution. Dissolution is accomplished by heating the mixture at 70° C. for 30 minutes. To this mixture the plasticizer tris(2-ethylhexyl)phosphate (Fluka) is added, to provide a total solids content of 35 g/dL. The resulting mixture is then allowed to cool to 45° C. and nonactine (Fluka) is added in the amount equivalent to 2 percent of the total solids in the mixture. At room temperature, 10-100 nL of this final material is microdispensed onto each of the silver chloride indicator electrodes on the wafer, overlapping on all sides by at least about 30 μm. Curing is accomplished by placing the wafer on a 60° C. hotplate for 30 minutes. This process yields a stable, rugged structure having a thickness of about 15 μm. The wafer is then washed and partially dices, as described previously above for the preferred embodiment of a combined glucose and cholesterol sensor.

Urease (30 mg; 90 IU/mg Sigma) is dissolved in deionized water (60 mg). To this solution is added 1.0 mg of sorbitol and 150 mg of poly(vinyl acetate-co-ethylene) latex (type ELVACE 40711-00, Reichhold). After mixing, 30 mg of a 1% aqueous glutaraldehyde solution is added, and the resulting mixture is stirred. This mixture is then microdispensed (10-100 nL) over each of the ammonium ion sensitive membranes ensuring that the latex mixture overlapped on all sides by at least 30 μm. The final membrane has a thickness of about 50 μm. The wafer is then cleaved to yield individual sensors and stored dry.

6.10. Microdispensable Membrane Formulations

The following formulations can be loaded into a microsyringe assembly for the purpose of establishing ionsensitive layers in a controllable manner. The microsyringe assembly is preferably equipped with 25 to 30 gauge needles (EFD Inc.) having an internal diameter of 150 μm and an external diameter of 300 μm. Typically, the microsyringe needle, which includes an elongated member and a needle tip, is made of a metallic material, like stainless steel. As mentioned elsewhere in this specification, additional layers may be coated onto the needle to change its surface properties. Additionally, other materials such as synthetic polymers may also be employed in manufacturing the main body of the needle, itself. The inventors have found that, depending on the pretreatment of the electrode surface and the volume amount of fluid applied, membrane layers of a thickness ranging from about 1 to about 200 μm can be obtained consistently.

6.10.1. POTASSIUM ION MEMBRANE

Weigh:
3.55 g NMP (N-Methylpyrrolidcne)
2.67 g Propiophenone
2.67 g Cyclohexanone
4.00 g Bis(2-ethylhexyl) sebacate
Combine these ingredients in a pyrex beaker and mix thoroughly, preferably with the aid of a magnetic stirrer. Add 1.33 g PVC. Heat solution to 100° C. and leave 1 hour. Add 159 mg valinomycin and stir 15 minutes. Allow to cool to 40° C. and transfer to storage vessel.

6.10.2. CHLORIDE ION MEMBRANE
Weigh:
0.95 g Cyclohexanone
1.77 g Propiophenone
0.47 g 5-Phenyl-1-pentanone
Combine these ingredients in a pyrex beaker and mix thoroughly, preferably with the aid of a magnetic stirrer. Add 0.47 g PVC Sigma P-9401 and stir slowly. Heat solution to 100.C and leave for 30 min. Add 0.20 g Triodecylmethyl ammonium chloride and 0.20 g Kemamine BQ-9702C fatty amine. Stir for 15 mins with heating. Allow to cool to 40° C. and transfer to storage vessel.

6.10.3. SODIUM MEMBRANE
Weigh:
3.81 g NMP
2.86 g Propiophenone
2.86 g Cyclohexanone
4.00 g Tris (2-ethylhexyl) phosphate
Combine these ingredients in a pyrex beaker and mix thoroughly, preferably with the aid of a magnetic stirrer. Add 1.71 g of PVP (Geon 137). Heat Solution to 100° C. Add 100 mg Methyl Monensin, dissolved in 1.0 g cyclohexanone. Allow to cool to 40° C. and transfer to storage vessel.

6.10.4. AMMONIUM MEMBRANE
Weigh:
1.38 g NMP
1.04 g Cyclohexanone
1.04 g Propiophenone
1.65 g Tris (2-ethylhexyl) phosphate
Combine these ingredients in a pyrex beaker and mix thoroughly, preferably with the aid of a magnetic stirrer. Add 0.281 g PVC Geon 137 and 0.545 g of PVC Sigma P-9401. Heat solution to 100° C. and leave 1 hour. Add 50 mg of nonactin and stir 15 mins. Allow to cool to 40° C. and transfer to storage vessel.

6.10.5. UREASE MEMBRANE
A urease solution is prepared by combining:
0.29 g of 10% ambergum solution
0.30 g of 10% BSA solution
0.11 g of urease.

The ingredients are mixed in a glass vial and swirled gently for 15 mins. The solution is allowed to stand for 24 h. After this period, the solution is centrifuged. The supernatant urease solution is decanted and saved.

The urease membrane formulation is then obtained by combining:
0.028 g of the urease solution prepared above.
0.2851 g Elvace
0.0384 g deionized water.

The ingredients are mixed and swirled gently in a glass vial for several minutes. Then, ambergum solution (0.03 g) is added, followed by 1% glutaraldehyde solution (0.011 g). The resulting mixture is swirled for 5 mins. The formulation is allowed to stand for about 0.5 h before use. The urease membrane is then established on top of an ammonium ion sensitive membrane.

6.10.6. pH Membrane
A formulation suitable for establishing a pH sensitive membrane is prepared by combining equal volumes of cyclohexanone and propiophenone. To 1.5 g of this solvent mixture is added, with stirring and gently warming: sodium tetraphenylborate (5 mg), tridodecyl amine (75 mg), dibutyl sebacate (620 mg), and, lastly, 300 mg of high-molecular weight HMW PVC. Also, o-nitrophenyloctylether (620 mg) may be used in place of the dibutyl sebacate. The resulting composition is mixed thoroughly before use.

6.10.7. Calcium Ion Membrane
To 2.75 g of a 50/50 cyclohexanone/propiophenone solvent mixture is added p-tetraoctylphenylphosphate diester, calcium salt (110 mg). The mixture is stirred and warmed gently to help dissolve the calcium salt. The mixture is then filtered through a 0.45 μm PTFE filter. To the warm filtrate is then added, with stirring, 580 mg of HMW PVC (or, alternatively, 200 mg COO carboxylated PVC and 380 mg HMW PVC). After a solution is obtained, n-dioctylphenylphosphonate (1300 mg) is added. The mixture is stirred and warmed gently, as needed, until a solution is obtained.

6.11. Pretreatment of Wafer Surface and Deposition of Selected Membranes

The following conditions are used to pretreat a wafer containing several hundred base sensors with a patterned polyimide passivation layer. The wafer is first etched with an argon plasma, followed by a $CF_4$ plasma. As described previously, the degree of hydrophobicity or hydrophilicity may be varied by adjusting the power and gas flow, or by changing the time of exposure. In this particular example, the treated surface is quite hydrophobic.

| Equipment: | Tegal plasma etcher |
|---|---|
| Temperature: | 16° C. |
| Argon Plasma | |
| Flow: | 14.4 sccm |
| Process pressure: | 100 mT |
| Forward power: | 200 W |
| Reflected power: | less than 10 W |
| Time: | 30 secs |
| $CF_4$ plasma | |
| $CF_4$ supply at 17 PSIG | |
| Flow: | 66 sccm |
| Process pressure: | 800 mT |
| Forward power: | 30 W |
| Reflected power: | less than 10 W |
| Time: | 30 secs. |

After treatment, the wafer is washed with deionized water and is baked over a hot plate to ensure sufficient surface dehydration. The wafer is then mounted on a film frame with dicing tape backing and diced as described previously to provide properly aligned individual sensors.

The microdispensing system is then used to deposit membranes, with 1 or more drops being deposited to form each membrane. The urea layer is dispensed over the previously dispensed $NH_4^+$ membrane. Preferably, the microdispensing process is carried out under a controlled low humidity environment.

| Membrane | Preferred Thickness | Minimum Thickness |
|---|---|---|
| $K^+$ | 40 ± 20 μm | 20 μm |
| $Na^+$ | 30 ± 10 μm | 20 μm |

-continued

| Membrane | Preferred Thickness | Minimum Thickness |
|---|---|---|
| $NH_4^+$ | 15 ± 5 μm | 10 μm |
| Cl | 40 ± 20 μm | 20 μm |
| pH | 40 ± 20 μm | 20 μm |
| $Ca^{++}$ | 40 ± 20 μm | 20 μm |
| Urease enzyme | 45 ± 15 μm | 30 μm |

It should be noted that other methods, known to those skilled in the art, exist for changing the surface free energy of a planar struture (See, for example, Wolf, S. and Tauber, R.N. in *Processing Technology*, Vol. 1, Lattice Press (1986) or Moss, S.J. and Ledwith, A. in *The Chemistry of the Semiconductor Industry*, Blackie (1987)). These methods include, but are not limited to, wet etching, dry (plasma) etching, plasma polymerization and deposition, particle beam bombardment, reactive ion etching, corona treatment, microwave, ultraviolet, Langmuir-Blodgett film coating, and covalent chemical modifiction. Also, any suitable combination of these techniques may be utilized to obtain the desired surface free energy.

Generally, the information gained from measuring the contact angle is used to assess the quality of the surface treatment. The membrane thickness measurements provide an indication of the expected performance of the finished sensor (i.e., wet-up behavior and Nernstian response).

It is apparent to those skilled in the art that variations and modifications in the microfabrication processes disclosed herein and in the biosensors, themselves, can be readily conceived in view of the present invention. Accordingly, while a number of preferred embodiments of the invention have been described, the invention is not limited thereby but only by the following claims.

What is claimed is:

1. A method for forming a permselective layer on preselected areas of a substantially planar sensing device which comprises:
   (a) establishing a photoresist layer on a substantially planar sensing device;
   (b) processing said photoresist layer using photolithographic techniques to expose preselected areas of said sensing device;
   (c) establishing at least one film comprising a silane compound mixed with a suitable solvent on the sensing device of step (b), said compound having the formula $R'_nSi(OR)_{4-n}$, in which n is an integer selected from the group consisting of 0, 1, and 2; R' is a hydrocarbon radical comprising 3-12 carbon atoms; and R is a hydrogen radical or a lower alkyl radical comprising 1-4 carbon atoms; and
   (d) heating said film to a temperature of at least about 100° C. for a period of time effective to form a permselective layer having a thickness of about 1 to about 1000 nm sufficient to provide said permselective layer with the desired semipermeable properties in which molecules having about a first preselected molecular weight or above are substantially precluded from permeating through said permselective layer, while molecules having about a second preselected molecular weight or below may effectively permeate therethrough; and
   (e) removing the underlying photoresist layer and the permselective layer overlaid thereover from all except the preselected areas of said sensing device.

2. The method of claim 1 which further comprises heating said device of step (e) to a temperature in excess of about 150° C. to about 250° C. to maximize the indicator electrode response toward the oxidation of hydrogen peroxide.

3. The method of claim 1 which further comprises heating said device of step (e) to a temperature in the range of about 150° C. to about 250° to maximize the indicator electrode response toward the oxidation of hydrogen peroxide.

4. The method of claim 1 in which said film is heated in step (d) to a temperature or about 160° C. to maximize the indicator electrode response toward the oxidation of hydrogen peroxide.

5. A method of forming a permselective layer on preselected areas of a substantially planar sensing device which comprises:
   (a) establishing at least one film comprising a silane compound mixed with a suitable solvent on a substantially planar sensing device, said compound having the formula $R'_nSi(OR)_{4-n}$, in which n is an integer selected from the group consisting of 0, 1 and 2; R' is a hydrocarbon radical comprising 3-12 carbon atoms; and R is a hydrogen radical or a lower alkyl radical comprising 1-4 carbon atoms; and
   (b) heating said film to a temperature of at least about 100° C. for a period of time effective to form a permselective layer having a thickness of about 1 to about 1,000 nm sufficient to provide said permselective layer with the desired semipermeable properties in which molecules having about a first preselected molecular weight or above are substantially precluded from permeating through said permselective layer, while molecules having about a second preselected molecular weight or below may effectively permeate therethrough;
   (c) establishing a photoresist layer on said permselective layer;
   (d) processing said photoresist layer using photolithographic techniques such that a proportion of the underlying permselective layer becomes exposed and subject to further processing, while those preselected areas of the device retain a protective cap of photoresist material;
   (e) removing said exposed permselective layer; and
   (f) removing said protective photoresist layer to leave a permselective layer over preselected areas of said device.

6. The method of claim 5 in which step (e) comprises contacting said permselective layer with an etchant selected from the group consisting of dry agents, wet agents, and combinations thereof.

7. The method of claim 5 in which step (e) comprises contacting said permselective layer with an etchant selected from the group consisting of an oxygen plasma, a 0.0001-0.01 weight percent solution of hydrofluoric acid in a protic solvent and combinations thereof.

8. The method of claim 5 which further comprises heating said device of step (f) to a temperature in excess of about 150° C. to about 250° C. to maximize the indicator electrode response toward the oxidation of hydrogen peroxide.

9. The method of claim 5 which further comprises heating said device of step (f) to a temperature in the range of about 150° C. to about 250° C. to maximize the indicator electrode response toward the oxidation of hydrogen peroxide.

10. The method of claim 5 in which said film is heated in step (b) to a temperature of about 160° C. to maximize the indicator electrode response toward the oxidation of hydrogen peroxide.

11. The method of claim 1 or 5 in which the thickness of said permselective layer is such that said permselective layer is permeable to molecules having a molecular weight of about 50 or less, yet substantially impermeable to molecules having a molecular weight of about 120 or more.

12. The method of claim 1 or 5 in which the thickness of said permselective layer is in the range of about 20 to about 500 Å.

13. The method of claim 1 or 5 in which said permselective layer is further characterized as: (i) having a thickness in the range of about 50 to about 100 Å; (ii) being permeable to molecules selected from the group consisting of dioxygen and hydrogen peroxide; and (iii) being substantially impermeable to molecules selected from the group consisting of uric acid, ascorbic acid, salicylic acid, 2-(p-isobutylphenyl)propionic acid, cysteine, 4-acetamidophenol, and physiological salts thereof.

14. The method of claim 1 or 5 in which said sensing device is an amperometric electrochemical sensor.

15. The method of claim 1 or 5 in which said solvent is comprised of an aqueous solution of a nonionic surfactant present in a concentration of about 0.005 to about 0.2 percent by weight of said aqueous solution.

16. The method of claim 1 or 5 in which said solvent is a water-immiscible organic solvent.

17. The method of claim 1 or 5 in which said solvent is a chlorinated organic solvent selected from the group consisting of methylene chloride, trichloroethane, tetrachloroethane, chlorobenzene, dichlorobenzene, and mixtures thereof.

18. The method of claim 1 or 5 in which said film is established by a means selected from the group consisting of spin-coating, dip-coating, spray-coating, and microdispensing.

19. The method of claim 1 or 5 in which said film is heated to a temperature in the range of about 100° C. and about 250° C. for a period of at least about 5 minutes.

20. The method of claim 1 or 5 in which said silane compound is N-(2-aminoethyl)-3-aminopropyltrimethoxysilane.

21. The method of claim 1 or 5 in which said film is established by a microdispensing system.

22. The method of claim 1 or 5 in which different silane films are established.

23. The method of claim 1 or 5 in which said preselected areas encompass the indicator electrode of an amperometric electrochemical sensor.

24. The method of claim 1 or 5 in which said photoresist layer is comprised of a positive photoresist and said processing step comprises (i) irradiating said photoresist layer through a mask, and (ii) developing the irradiated photoresist layer to expose preselected areas of said sensing device.

25. The method of claim 24 in which said developing step comprises contacting said irradiated photoresist layer with a lower alkyl acetate ester solvent.

26. The method of claim 1 or 5 in which step (e) or step (f), respectively, comprises exposing said device to a solvent capable of dislodging or dissolving said photoresist layer.

27. The method of claim 1 or 5 in which said hydrocarbon radical further comprises at least one heteroatom selected from the group consisting of oxygen, nitrogen, phosphorus, sulfur and stable combinations thereof.

28. The method of claim 1 or 5 in which n is equal to 1.

29. A method for forming a patterned semipermeable solid film onto a planar sensing device which comprises:
(a) establishing a layer of a resist material over a planar sensing device;
(b) subjecting the layer of step (a) to radiant energy through a photolithographic mask and developing the resultant irradiated layer such that preselected area of said device become exposed and subject to further processing;
(c) establishing a liquid film over the patterned layer of step (b), which liquid film comprises an organosilicon compound mixed with a suitable solvent, said compound having the formula $R'Si(OR)_3$ in which R' is a hydrocarbon radical comprising 3-12 carbon atoms and R is a lower alkyl radical comprising 1-4 carbon atoms;
(d) heating the liquid film of step (c) to a temperature of at least about 100° C. for a period of time effective to form a solid film having a thickness of about 20 to about 500 Å sufficient to provide said solid film with the desired semipermeable properties in which molecules having molecular weights above a given threshold can be effectively excluded from entering and diffusing through said solid film, while allowing the free passage and diffusion of lower molecular weight electroactive species; and
(e) exposing the solid film of step (d) to a solvent capable of dislodging the underlying layer of resist material and allowing said solid film to separate from said device, leaving a patterned semipermeable solid film over the preselected areas of said device.

30. The method of claim 29 which further comprises heating said device of step (e) to a temperature in the range of about 150° to about 250° C. to maximize the indicator electrode response toward the oxidation of hydrogen peroxide.

31. The method of claim 29 in which said film is heated in step (d) to a temperature of 170° C. to maximize the indicator electrode response toward the oxidation of hydrogen peroxide.

32. A method of forming a patterned semipermeable solid film onto a planar sensing device which comprises:
(a) establishing a liquid film over a planar sensing device, which liquid film comprises an organosilicon compound mixed with a suitable solvent, said compound having the formula $R'Si(OR)_3$ in which R' is a hydrocarbon radical comprising 3-12 carbon atoms and R is a lower alkyl radical comprising 1-4 carbon atoms;
(b) heating the liquid film of step (a) to a temperature of at least about 100° C. for a period of time effective to form a solid film having a thickness of about 20 to about 500 Å sufficient to provide said solid form with the desired semipermeable properties in which molecules having molecular weights above a given threshold can be effectively excluded from entering and diffusing through said solid film, while allowing the free passage and diffusion of lower molecular weight electroactive species;

(c) establishing a layer of a resist material over the solid film of step (b);

(d) subjecting the layer of step (c) to radiant energy through a photolithographic mask and developing the resultant irradiated layer such that a substantial proportion of the underlying solid film becomes exposed and subject to further processing, while those preselected areas of the device retain a protective cap of resist material;

(e) subjecting the exposed solid film of step (d) to an etchant for a length of time sufficient to remove substantially all of said exposed solid film; and semipermeable solid film over the preselected areas of said device.

33. The method of claim 32 in which said etchant is selected from the group consisting of dry and wet agents.

34. The method of claim 32 in which said etchant is selected from the group consisting of an oxygen plasma and a 0.0001–0.01 weight percent solution of hydrofluoric acid in a protic solvent.

35. The method of claim 32 which further comprises heating said device of step (f) to a temperature in the range of about 150° C. to about 250° C. to maximize the indicator electrode response toward the oxidation of hydrogen peroxide.

36. The method of claim 32 in which said film is heated in step (b) to a temperature of 170° C. to maximize the indicator electrode response toward the oxidation of hydrogen peroxide.

37. The method of claim 29 or 32 in which the thickness of said solid film is such that molecules having a molecular weight of about 120 or more are substantially precluded from permeating through said solid film, while molecules having a molecular weight of about 50 or less may diffuse through effectively.

38. The method of claim 29 or 32 in which the thickness of said solid film is in the range of about 20 to about 500 Å.

39. The method of claim 21 or 32 in which said solid film is further characterized as: (i) having a thickness in the range of about 50 to about 100 Å; (ii) being permeable to molecules selected from the group consisting of dioxygen and hydrogen peroxide; and (iii) being substantially impermeable to molecules selected from the group consisting of uric acid, ascorbic acid, salicylic acid, 2-(p-isobutylphenyl)proprionic acid, cysteine, 4-acetamidophenol, and physiological salts thereof.

40. The method of claim 29 or 32 in which said planar sensing device is an amperometric electrochemical sensor manufactured by thin film technology.

41. The method of claim 29 or 32 in which said solvent is comprised of an aqueous solution of a nonionic surfactant present in a concentration of about 0.005 to about 0.2 percent by weight of said aqueous solution.

42. The method of claim 29 or 32 in which said solvent is a water-immiscible organic solvent.

43. The method of claim 29 or 32 in which said liquid film is established on said planar sensing device by a means selected from the group consisting of spin-coating, dip-coating, spray-coating, and microdispensing.

44. The method of claim 29 or 32 in which said liquid is heated to a temperature in the range of about 100° C. to about 250° C. for a period of at least about 5 minutes.

45. The method of claim 29 or 32 in which said hydrocarbon radical further comprises at least one heteroatom selected from the group consisting of oxygen, nitrogen, phosphorus, sulfur, and stable combinations thereof.

46. The method of claim 29 or 32 in which said organosilicon compound is N-)2-aminoethyl)-3-aminopropyltrimethoxysilane.

47. The method of claim 1, 5, 29 or 32 in which the thickness of said permselective layer is in the range of about 20 to about 200 Å.

48. The method of claim 1, 5, 29 or 32 in which the thickness of said permselective layer is in the range of about 50 to about 100 Å.

* * * * *